(12) United States Patent
Toner et al.

(10) Patent No.: US 8,807,879 B2
(45) Date of Patent: Aug. 19, 2014

(54) SYSTEMS AND METHODS FOR PARTICLE FOCUSING IN MICROCHANNELS

(75) Inventors: Mehmet Toner, Wellesley, MA (US); Dino Dicarlo, Los Angeles, CA (US); Jon F. Edd, Franklin, TN (US); Daniel Irimia, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/619,309

(22) Filed: Sep. 14, 2012

(65) Prior Publication Data

US 2013/0011210 A1 Jan. 10, 2013

Related U.S. Application Data

(62) Division of application No. 13/480,862, filed on May 25, 2012, which is a division of application No. 12/103,885, filed on Apr. 16, 2008, now Pat. No. 8,186,913.

(60) Provisional application No. 60/923,609, filed on Apr. 16, 2007, provisional application No. 60/923,837, filed on Apr. 17, 2007, provisional application No. 60/999,131, filed on Oct. 16, 2007.

(51) Int. Cl.
*B65G 53/00* (2006.01)

(52) U.S. Cl.
USPC ............. 406/197; 406/92; 406/195; 435/174; 435/325; 356/246; 356/441; 436/52; 436/180; 422/502; 422/503; 73/61.71

(58) Field of Classification Search
USPC ............ 406/92, 195, 198, 197; 435/174, 325; 356/246, 441; 436/52, 180; 422/502, 422/503; 73/61.71

See application file for complete search history.

(56) References Cited

U.S. PATENT DOCUMENTS

| | | | |
|---|---|---|---|
| 3,693,792 A | 9/1972 | Lang | |
| 4,446,015 A | 5/1984 | Kirkland | |
| 5,412,466 A | 5/1995 | Ogino | |

(Continued)

FOREIGN PATENT DOCUMENTS

| | | |
|---|---|---|
| JP | H10-500912 | 1/1998 |
| JP | 2002-503334 | 1/2002 |

(Continued)

OTHER PUBLICATIONS

International Search Report and Written Opinion issued Jan. 1, 2009 in International Application No. PCT/US2008/060440, 6 pgs.

(Continued)

*Primary Examiner* — Joseph A Dillon, Jr.
(74) *Attorney, Agent, or Firm* — Fish & Richardson P.C.

(57) ABSTRACT

Various systems, methods, and devices are provided for focusing particles suspended within a moving fluid into one or more localized stream lines. The system can include a substrate and at least one channel provided on the substrate having an inlet and an outlet. The system can further include a fluid moving along the channel in a laminar flow having suspended particles and a pumping element driving the laminar flow of the fluid. The fluid, the channel, and the pumping element can be configured to cause inertial forces to act on the particles and to focus the particles into one or more stream lines.

17 Claims, 47 Drawing Sheets

(56) References Cited

U.S. PATENT DOCUMENTS

| | | | |
|---|---|---|---|
| 5,819,948 | A | 10/1998 | Van den Engh |
| 5,968,820 | A | 10/1999 | Zborowski et al. |
| 5,972,710 | A | 10/1999 | Weigl et al. |
| 6,003,678 | A | 12/1999 | Van den Engh |
| 6,169,394 | B1 | 1/2001 | Frazier et al. |
| 6,454,945 | B1 | 9/2002 | Weigl et al. |
| 6,506,609 | B1 | 1/2003 | Wada et al. |
| 6,540,896 | B1 | 4/2003 | Manz et al. |
| 6,767,706 | B2 | 7/2004 | Quake et al. |
| 6,808,075 | B2 | 10/2004 | Bohm et al. |
| 6,964,736 | B2 | 11/2005 | Quake et al. |
| 7,079,244 | B2 | 7/2006 | Gold et al. |
| 7,104,405 | B2 | 9/2006 | Bohm et al. |
| 7,129,091 | B2 | 10/2006 | Ismagilov et al. |
| 7,157,274 | B2 | 1/2007 | Bohm et al. |
| 7,161,674 | B2 | 1/2007 | Gold et al. |
| 7,182,552 | B2 | 2/2007 | Takagi et al. |
| 7,182,553 | B2 | 2/2007 | Takagi et al. |
| 7,276,170 | B2 | 10/2007 | Oakey et al. |
| 7,311,476 | B2 | 12/2007 | Gilbert et al. |
| 7,312,085 | B2 | 12/2007 | Chou et al. |
| 7,318,902 | B2 | 1/2008 | Oakey et al. |
| 7,452,726 | B2 | 11/2008 | Chou et al. |
| 7,611,309 | B2 | 11/2009 | Gilbert et al. |
| 7,670,471 | B2 | 3/2010 | Quake et al. |
| 7,682,838 | B2 | 3/2010 | Wang et al. |
| 7,691,636 | B2 | 4/2010 | Frazier et al. |
| 7,735,652 | B2 | 6/2010 | Inglis et al. |
| 7,745,221 | B2 | 6/2010 | Butler et al. |
| 7,770,738 | B2 | 8/2010 | Tabata et al. |
| 7,802,686 | B2 | 9/2010 | Takagi et al. |
| 7,807,454 | B2 * | 10/2010 | Oh et al. .............. 435/308.1 |
| 7,858,372 | B2 | 12/2010 | Whalen |
| 8,120,770 | B2 * | 2/2012 | Huang et al. ............ 356/246 |
| 8,162,149 | B1 | 4/2012 | Perroud et al. |
| 8,208,138 | B2 * | 6/2012 | Papautsky et al. ........ 356/335 |
| 8,318,439 | B2 * | 11/2012 | Battrell et al. ............ 435/7.1 |
| 2002/0053532 | A1 | 5/2002 | Quake et al. |
| 2003/0027225 | A1 | 2/2003 | Wada et al. |
| 2003/0044832 | A1 | 3/2003 | Blankenstein |
| 2006/0040596 | A1 | 2/2006 | Robinson |
| 2006/0134599 | A1 | 6/2006 | Toner et al. |
| 2006/0169642 | A1 | 8/2006 | Oakey et al. |
| 2006/0246575 | A1 | 11/2006 | Lancaster et al. |
| 2007/0196820 | A1 | 8/2007 | Kapur et al. |
| 2007/0264675 | A1 | 11/2007 | Toner et al. |
| 2008/0041475 | A1 | 2/2008 | Fourkas et al. |
| 2008/0128331 | A1 | 6/2008 | Lean et al. |
| 2009/0029870 | A1 | 1/2009 | Ward et al. |
| 2009/0221073 | A1 | 9/2009 | Toner et al. |
| 2011/0028351 | A1 | 2/2011 | Perroud et al. |
| 2011/0167932 | A1 | 7/2011 | Thornburg et al. |
| 2011/0208113 | A1 | 8/2011 | Toma et al. |
| 2012/0081709 | A1 | 4/2012 | Durack |
| 2012/0138152 | A1 | 6/2012 | Villarruel et al. |
| 2012/0140205 | A1 | 6/2012 | Kaduchak et al. |
| 2012/0231391 | A1 | 9/2012 | Nakajima et al. |

FOREIGN PATENT DOCUMENTS

| | | |
|---|---|---|
| JP | 2003-527948 | 9/2003 |
| JP | 2004-330008 | 11/2004 |
| JP | 2006-504512 | 2/2006 |
| WO | WO2006/056219 | 6/2006 |

OTHER PUBLICATIONS

International Preliminary Report on Patentability issued Oct. 29, 2009 in International Application No. PCT/US2008/060440, 12 pgs.

Yamaguchi et al., "A Method for DNA detection in a microchannel: Fluid dynamics phenomena and optimization of microchannel structure," Talanta 68:700-707 (2006).

Ookawara et al., "Applicability of a miniaturized micro-separator/classifier to oil-water separation," Chem. Eng. Technol. 30(3): 316-321 (2007).

Ookawara et al., "Feasibility study on concentration of slurry and classification of contained particles by microchannel," Chem. Eng. J. 101:171-178 (2004).

Davis, "Secondary flow and three-dimensional separation in curved circular ducts," Ph.D. Thesis, Purdue University, (Dec. 1990) XP002496652, retrieved from the internet: URL:http://proquest.um,i.com/pqdweb?did=747583351&sid=1&Fmt=2&clientId=70702&RQT=309&Vname=PQD>.

Yamaguchi et al., "Interface configuration of the two-layered laminar flow in a curved microchannel," Chem. Eng. J. 101:367-372 (2004).

Ookawara et al., "Numerical study on development of particle concentration profiles in a curved microchannel," Chem. Eng. Sci. 61(11) 3714-3724 (2006).

EPO Communication pursuant to Article 94(3) EPC dated Feb. 26, 2010 issued in European application No. 08745947.5, 2 pgs.

Examination report dated Dec. 17, 2009 from corresponding U.S. Appl. No. 12/103,885.

Examination report dated Jun. 11, 2010 from corresponding U.S. Appl. No. 12/103,885.

Examination report dated Feb. 18, 2011 from corresponding U.S. Appl. No. 12/103,885.

Examination report dated Oct. 20, 2011from corresponding U.S. Appl. No. 12/103,885.

Summons to attend oral proceedings received for corresponding application EP 08745947.5 dated May 3, 2013.

B. Chun et al: "Inertial migration of neutrally buoyant particles in a square duct: an Investigation of multiple equilibrium positions", Physics of Fluids, vol. 18, No. 3, Jan. 1, 2006, p. 031704, ISSN: 1070-6631, DOI: 10.1063/1.2176587.

Search Report for corresponding application EP 12156921.4 dated Feb. 6, 2013.

Examination Report for corresponding application EP 12156921.4 dated Mar. 28, 2013.

Examination report dated Oct. 1, 2013 for corresponding application EP 12157192.1, 14 pages.

* cited by examiner $F_{WALL}$  $F_{SHEAR}$

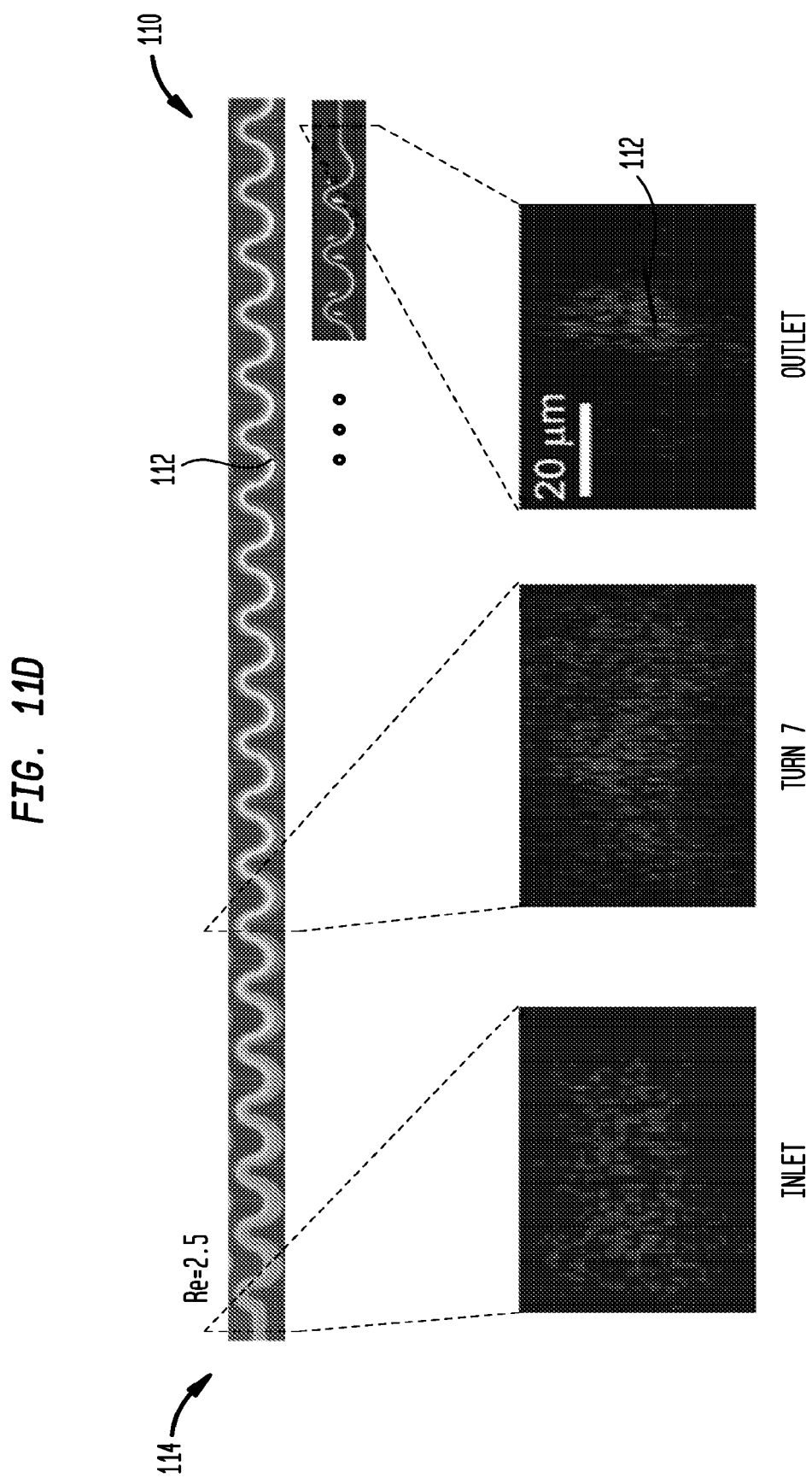

FIG. 22
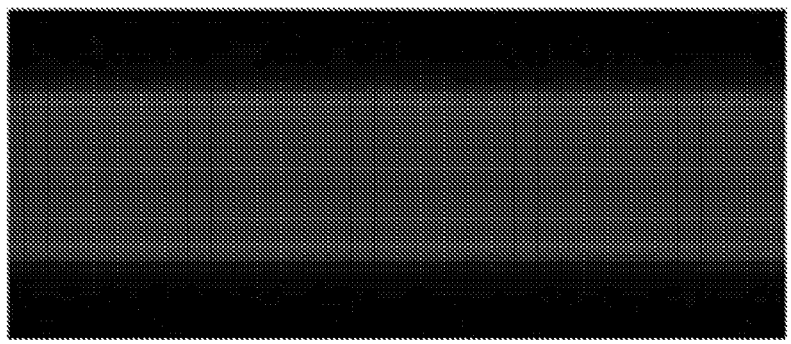
d/D=0.04
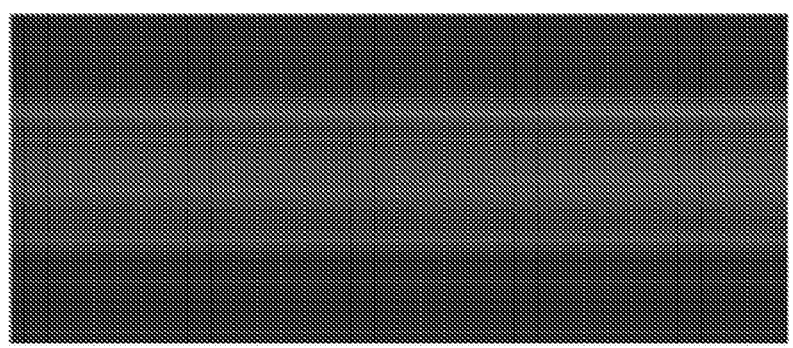
0.08
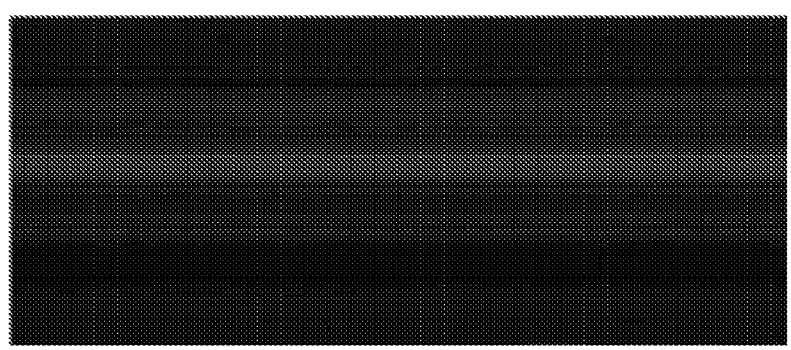
0.14
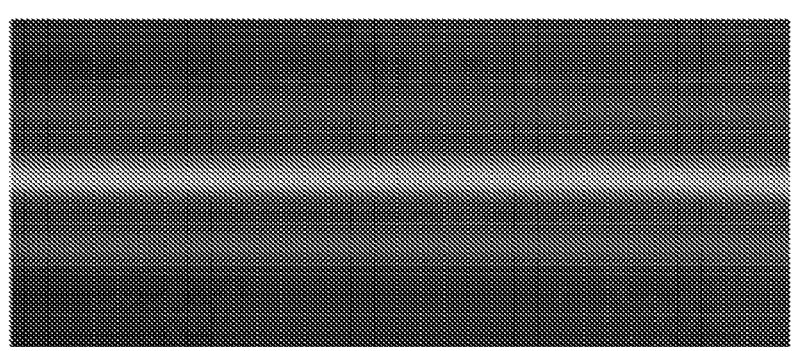
0.18

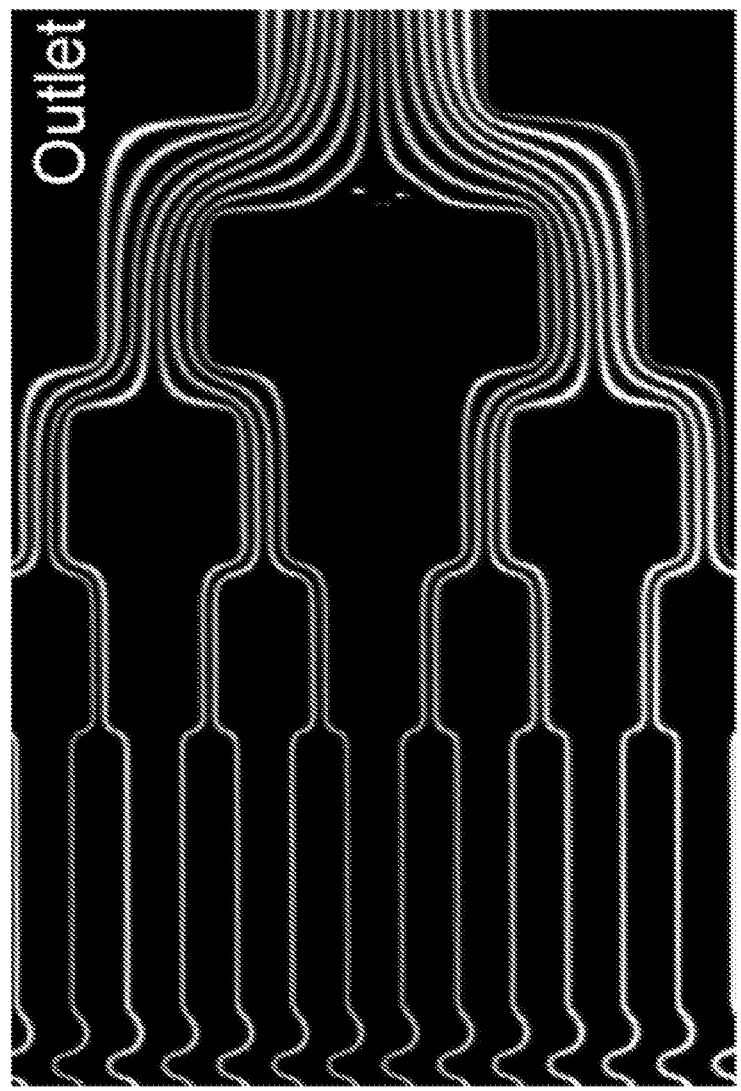
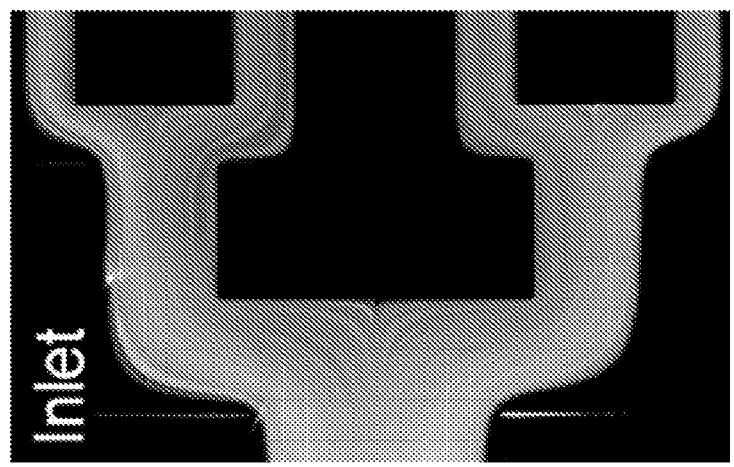
FIG. 23C

FIG. 27

PURITY AND YIELD

|  | YIELD (3.1μm) % | PURITY % |
|---|---|---|
| FRACTION 1 | 5% | 100% |
| FRACTION 1-2 | 10.8% | 99.9% |
| FRACTION 1-3 | 35.7% | 99.8% |
| FRACTION 1-4 | 60.6% | 99.1% |
| FRACTION 1-5 | 100% | 94.4% |

FIG. 28

SEPARATIONS IN SERIES FOR INCREASED ENRICHMENT

| TIER 0 | STARTING SOLUTION | | | |
|---|---|---|---|---|
| NUMBER OF 3.1 μm BEADS | $8.9 \times 10^8$ | | | |
| NUMBER OF 9.0 μm BEADS | $5.3 \times 10^7$ | | | |
| RATIO (3/9) | 17 | | | |
| VOLUME PROCESSED (mL) | 20 | | | |
| TIER 1 | FRACTION 1-4 | FRACTION 5 | | |
| NUMBER OF 3.1 μm BEADS | $5.0 \times 10^8$ | $2.4 \times 10^8$ | | |
| NUMBER OF 9.0 μm BEADS | $3.6 \times 10^6$ | $4.7 \times 10^7$ | | |
| RATIO (3/9) | 140 | 5.0 | | |
| ENRICHMENT RATIO | 8.0 | 0.30 | | |
| VOLUME (mL) | 16 | 4 | | |
| TIER 2 | FRACTION 1-4(1-4) | FRACTION 1-4(5) | FRACTION 5(1-3) | FRACTION 5(4-5) |
| NUMBER OF 3.1 μm BEADS | $4.9 \times 10^8$ | $1.6 \times 10^8$ | $1.2 \times 10^8$ | $1.3 \times 10^8$ |
| NUMBER OF 9.0 μm BEADS | $6.5 \times 10^4$ | $5.0 \times 10^6$ | $1.4 \times 10^5$ | $4.4 \times 10^7$ |
| RATIO (3/9) | 7600 | 31 | 860 | 3.0 |
| ENRICHMENT RATIO | 450 | 2.0 | 51 | 0.18 |
| VOLUME (mL) | 12.8 | 3.2 | 2.4 | 1.6 |

Re=2.5, 50 MICRON CHANNELS

FIG. 36
Re=0.5
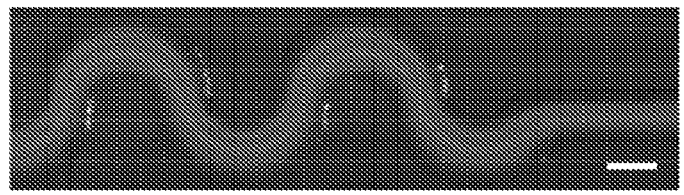
Re=2
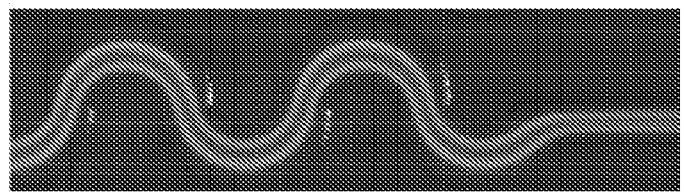
Re=5
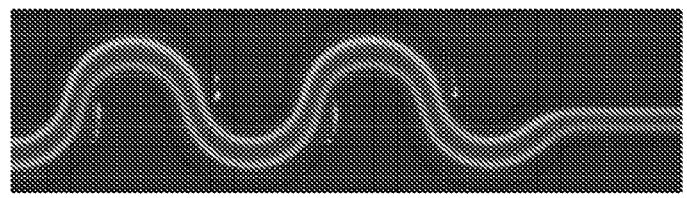
Re=10
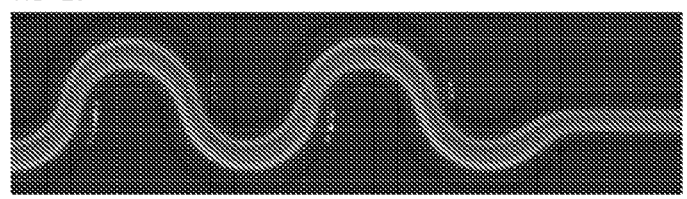
Re=20
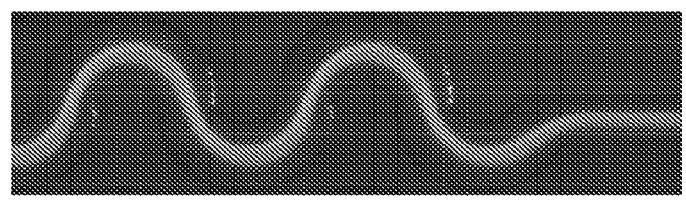
Re=30
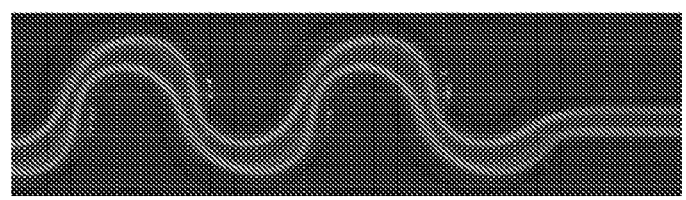
Re=50
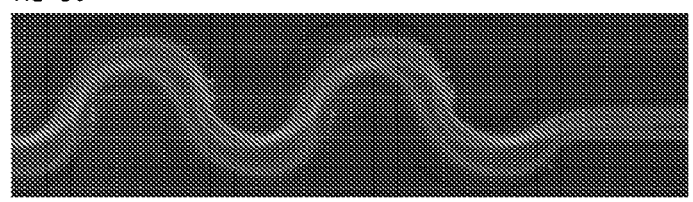

FIG. 39
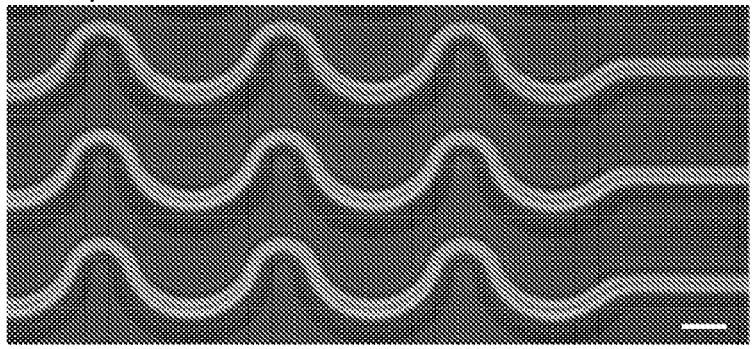
35/65μm-Re=1
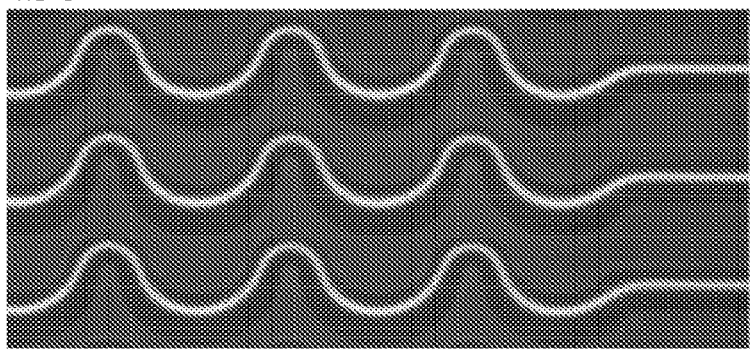
Re=5
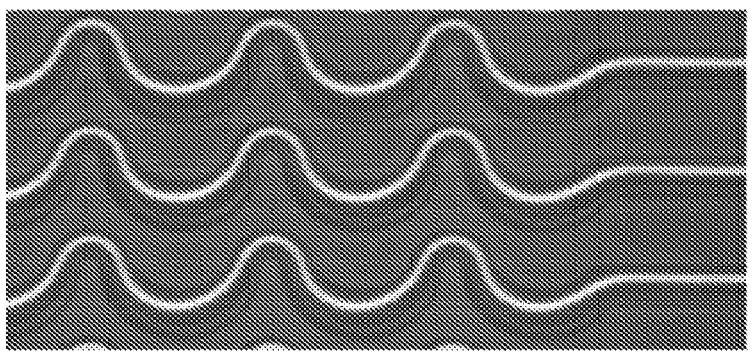
Re=10
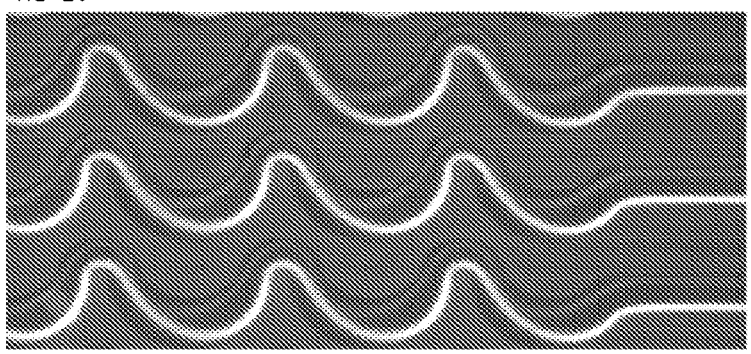
Re=20

FIG. 40
50/80μm-Re=0.05
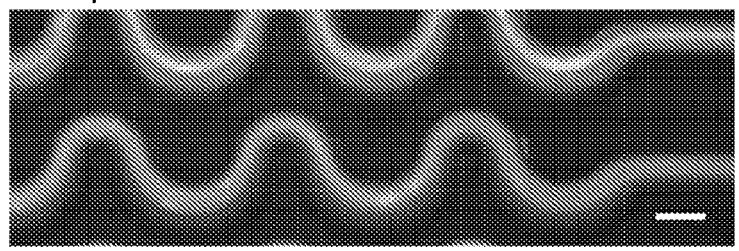
Re=2.5
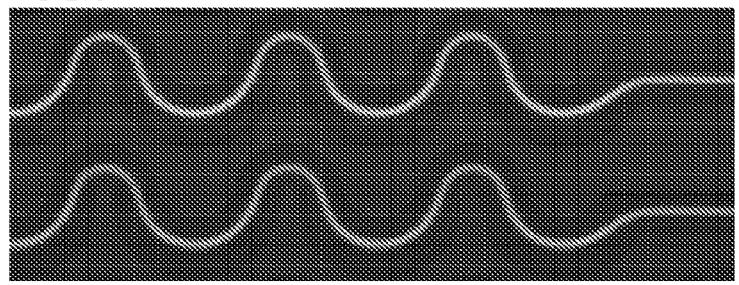
Re=5
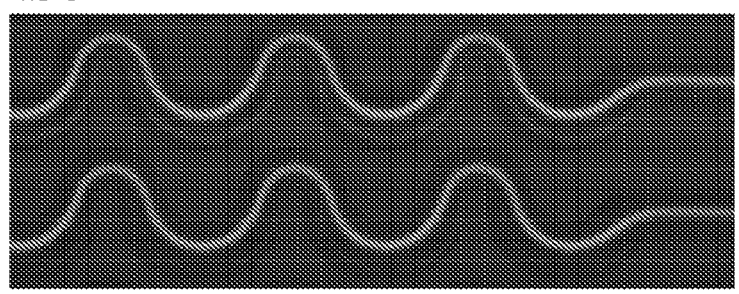
Re=15
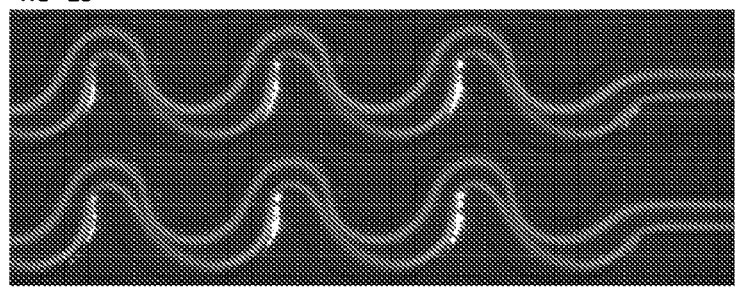
Re=25
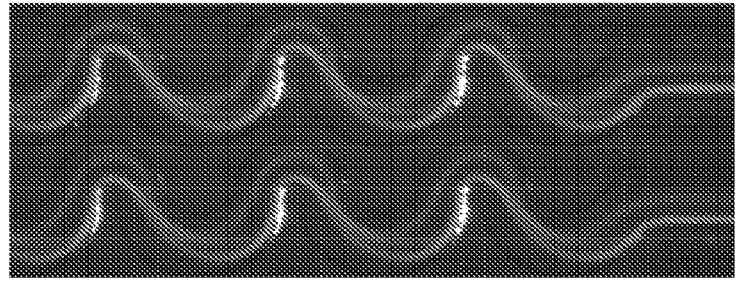

FIG. 41
100/160μm-Re=1
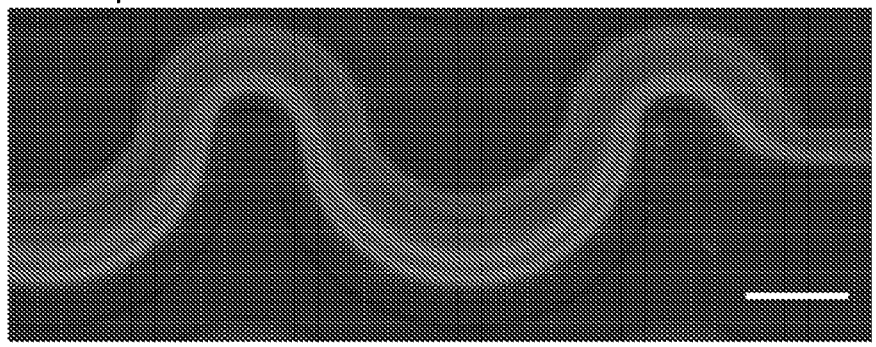
Re=6
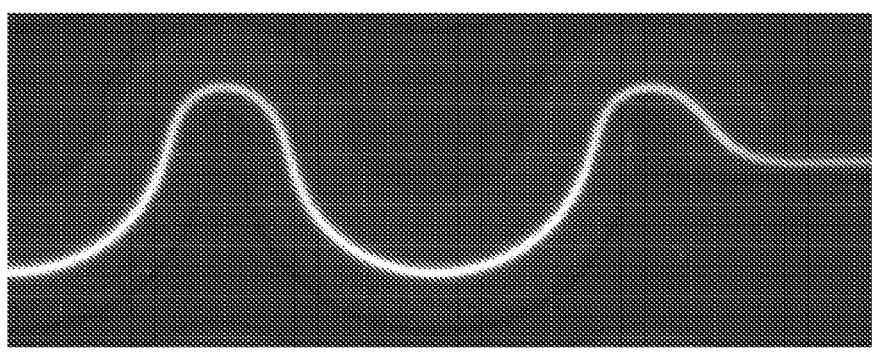
Re=12
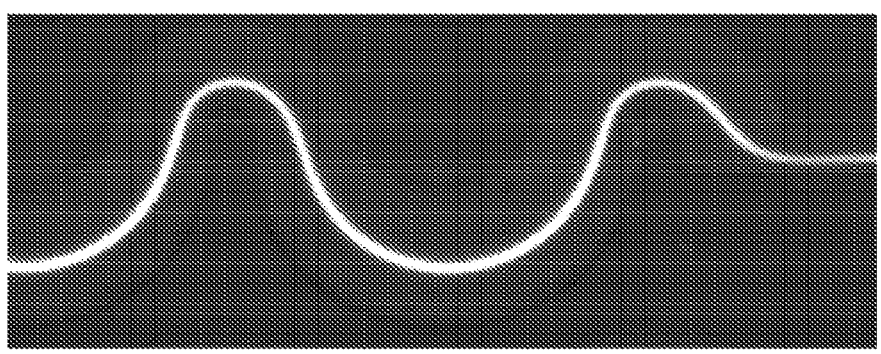
Re=36
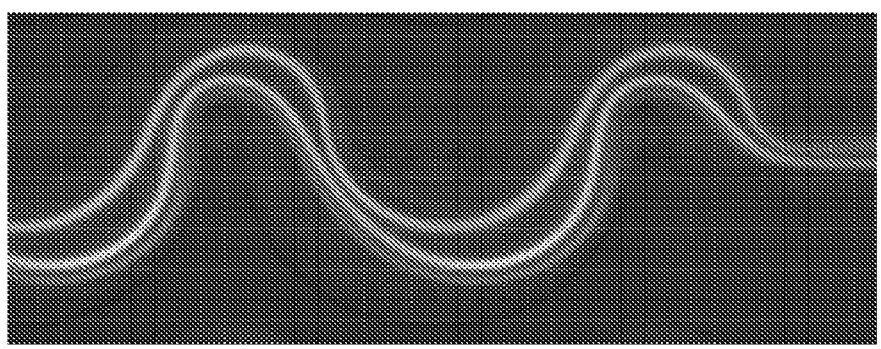

FIG. 42
350/650 m-Re=1.5
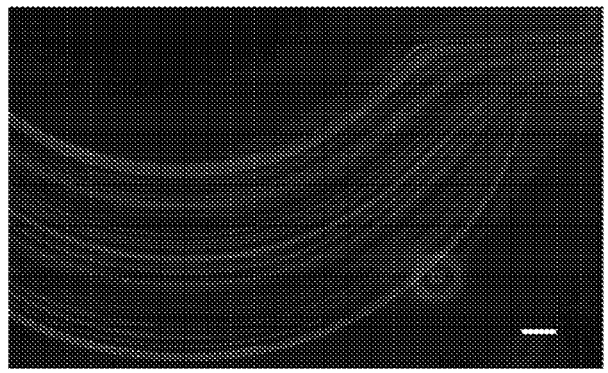
Re=30
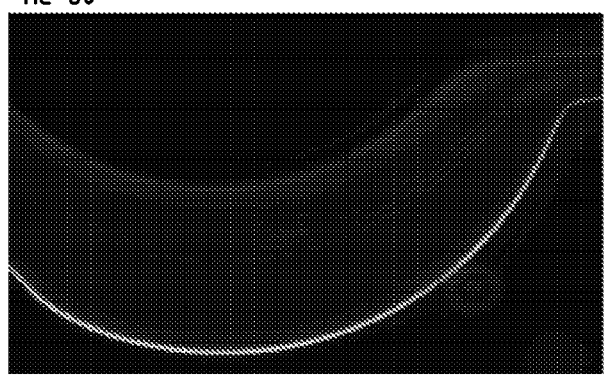
Re=90
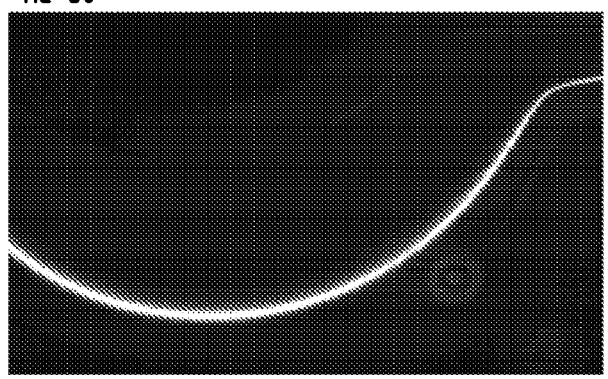
Re=150
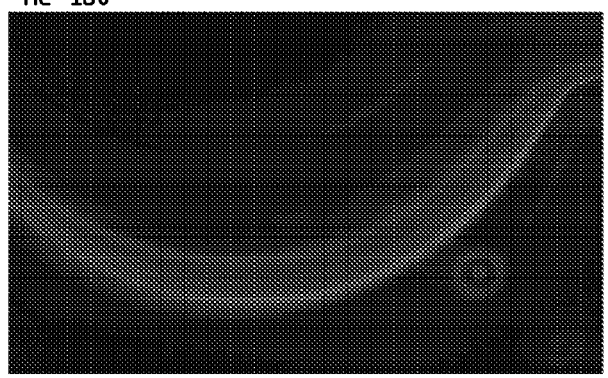

FIG. 44
Re=20 5% WHOLE BLOOD
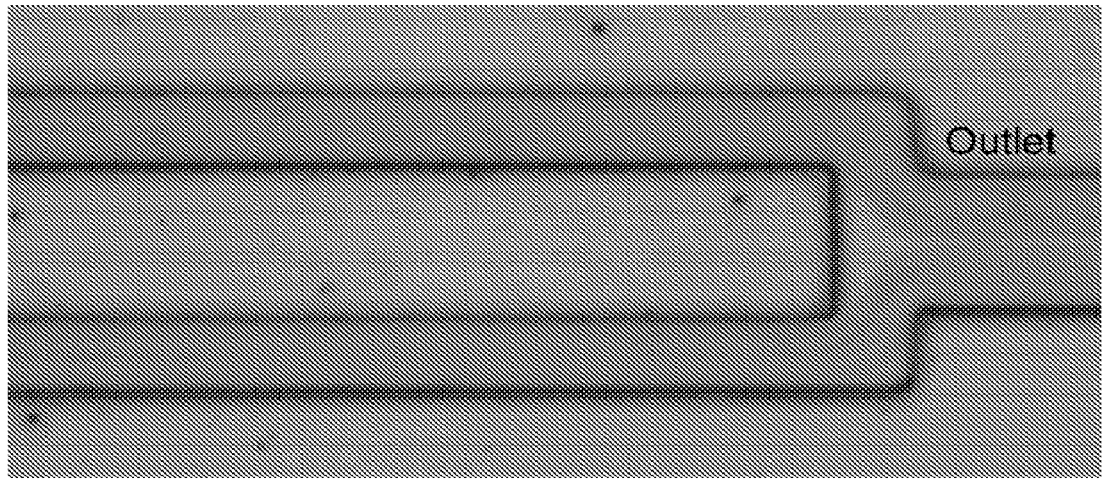
Re=100
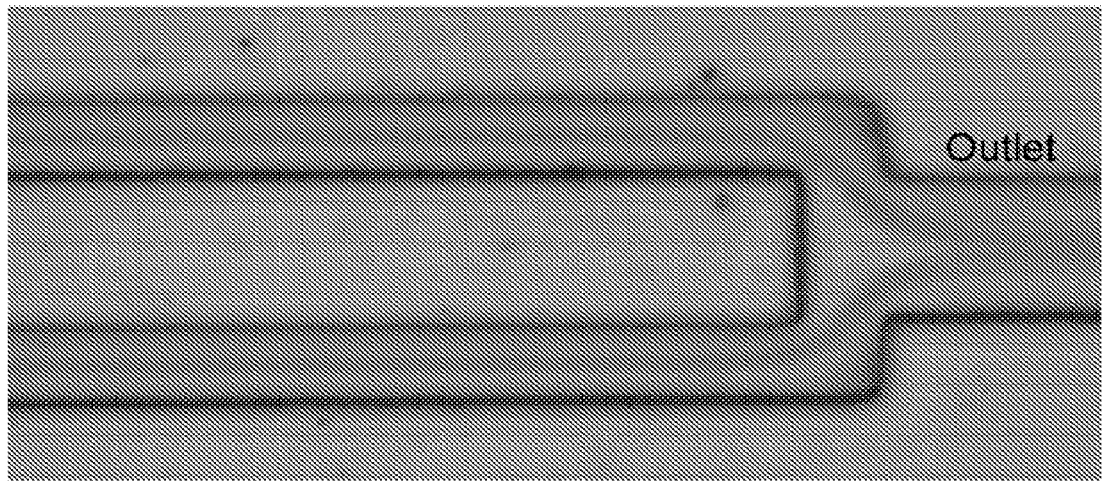

SYSTEMS AND METHODS FOR PARTICLE FOCUSING IN MICROCHANNELS

RELATED APPLICATIONS

This application is a divisional (and claims the benefit of priority under 35 USC 120) of U.S. application Ser. No. 13/480,862, filed on May 25, 2012, which is a divisional of U.S. application Ser. No. 12/103,885, filed on Apr. 16, 2008 now U.S. Pat. No. 8,186,913, claims priority to U.S. Provisional Application No. 60/923,609, filed on Apr. 16, 2007, and entitled "Methods and Devices for Separating and Focusing Particles," U.S. Provisional Application No. 60/923,837, filed on Apr. 17, 2007, and entitled "Methods and Devices for Separating and Focusing Particles," and U.S. Provisional Application No. 60/999,131, filed on Oct. 16, 2007, and entitled "Methods and Devices for Separating and Focusing Particles," all three of which are expressly incorporated herein by reference in their entireties.

BACKGROUND OF THE INVENTION

Particle separation and filtration has been applied for numerous technological solutions in industry, medicine, and research. Industrial applications include chemical process and fermentation filtration, water purification for the microelectronics industry, and wastewater treatment. Biomedical applications focus around counting, sorting and filtering various components of blood and preparing safely sized microbubble ultrasound contrast agents. Applications in basic and applied research include concentrating colloid solutions, purifying colloidal reaction products, and purifying and concentrating environmental samples.

Various macroscale techniques have been developed for particle separation to address these applications. Centrifugation and filter-based techniques are most common in current industrial applications because of the large scale of material that can be processed, but these systems are bulky, expensive, and may contain complex moving components. More recently, techniques based on the concept of field-flow fractionation (FFF) have been developed for a variety of applications. In these techniques, particle separation is due to either varied equilibrium positions within a channel in an applied force field or different transport rates. Various external fields have been implemented including gravitational, electrical, magnetic, and centrifugal, allowing successful separation of blood components, emulsions, and various colloids. A closely related technique, hydrodynamic chromatography, is also widely used in analytical separations and depends on size-dependent variation in the ability of particles to access low-drag regions of the flow. In most cases, the maximum flow through these systems is limited since sufficient time for forces to interact with particles or particles to sample the flow field is required. Flow cytometers are often used in sorting applications and allow sorting based on different parameters than other techniques (e.g., protein content, granularity); however, they have higher complexity than most sorting systems.

Microscale techniques offer advantages, in that scaling down allows the use of unique hydrodynamic effects and intensifies electromagnetic separation forces. Dielectrophoretic forces have been used to discriminate particles based on size or some dielectric tag. Other techniques for continuous separation rely on the laminar flow profile and different intersected cross sections of the flow for particles of varied sizes aligned at a wall. Further microscale techniques involve precisely designed filters or post arrays that create a bifurcation in particle direction based on size. These techniques can produce very accurate separations based on size or the dielectric properties of particles. For example, for deterministic displacement by asymmetrically aligned obstacles, a resolution of less than 20 nm is reported for particles of ~1 µm in diameter. Additionally, complexity can be low in these systems.

A disadvantage of current microscale separations is that scaling usually limits the throughput of these techniques. In most cases, particle volume fractions are maintained well below 1%, since particle-particle interactions can drastically affect performance. Additionally, small volumetric flow rates can lead to large average fluid velocities in microchannels leading to insufficient time for separation forces to act on particles. Flow rates usually range from 1 to 50 µL/min for these systems, insufficient for many preparative applications (e.g., concentration of rare cells in large volumes of blood, filtration of ultrasound contrast agents, or preparation of large amounts of colloids/emulsions). In these applications, it would be beneficial to process volumes of 3-20 mL within several minutes. For example, 2-6 mL of micro-bubble contrast agent is often injected for ultrasound imaging.

Accordingly, there is a need for a continuous particle sorting, separation, enumerating, or separation system that can take advantage of microscale physics but with throughput comparable to macroscale systems.

SUMMARY OF THE INVENTION

The invention described herein includes a number of systems, devices, apparatus, and methods that result in and use the self-ordering of particles suspended in a fluid traveling through a microfluidic channel. In a first aspect, a system is provided for focusing particles suspended within a moving fluid into one or more localized stream lines. The system includes a substrate and at least one channel provided on the substrate having an inlet and an outlet. The system further includes a fluid moving along the channel in a laminar flow having suspended particles and a pumping element driving the laminar flow of the fluid. The fluid, the channel, and the pumping element are configured to cause inertial forces to act on the particles and to focus the particles into one or more stream lines.

In another aspect, a method is provided for focusing particles in a moving fluid and includes providing particles suspended in a moving fluid into a channel and flowing the fluid through the channel under conditions such that inertial forces acting on the particles result in the localization of a flux of particles in the channel.

In a further aspect, an apparatus is provided for focusing particles of a predetermined size suspended within a moving fluid into one or more localized stream lines. The apparatus includes a substrate and at least one channel provided on the substrate having an inlet and an outlet wherein moving a fluid suspension having particles of a predetermined size from the inlet to the outlet in a laminar flow focuses the particles of a predetermined size into one or more localized stream lines.

In a still further aspect, a system is provided for sorting particles from a group of particles suspended in a fluid and includes a tagging system for tagging particles that are to be selectively sorted from a group of particles. The system further includes a substrate having at least one channel provided on the substrate having an inlet and an outlet. Moving the fluid suspension having particles, at least some of which have been tagged, from the inlet to the outlet in a laminar flow focuses the particles into one or more localized stream lines. The outlet can have at least two output branches, the first of the two output branches for separating the particles to be sorted, and the second of the two output branches for outputting the remainder of the particles that have not been segregated. The system can also include a sorting system operatively connected to the channel for selectively diverting particles to the first output branch.

In a final aspect, a method is provided for separating target particles from a population of particles and can include providing a population of particles, including target particles, in a fluid suspension and flowing the fluid suspension through at least one channel under conditions that cause at least some of the particles to form a localized flux of particles in the channel. The method can further include dividing an output from the channel into first and second output branches in which the output branches are configured so that the second output branch receives a flow that is enriched in target particles while the first output branch receives a flow reduced in target particles.

Specific embodiments of any of these aspects can include moving the fluid suspension can focus the particles into four localized streams, two localized streams, and/or a single localized stream. The channel can have a hydraulic diameter and a ratio of a size of the particles focused to the hydraulic diameter that is greater than or equal to about 0.07. The ratio of particle size to hydraulic diameter can be less than or equal to about 0.5. In some embodiments, a Reynolds Number of the fluid flow during focusing can be greater than or equal to about 1 and less than or equal to about 250. In some embodiments, a particle Reynolds number for the fluid suspension moving through the channel is greater than or equal to about 0.2. The one or more focused stream lines can have a width that is less than or equal to about five times, four times, three times, two times, and/or 1.05 times a size of the focused particles. Embodiments of the system can increase the concentration of particles in solution.

In the enumerated aspects or in any of their embodiments, at least first and second outlet branches can be formed at an outlet portion of the channel and at least one of the first and second outlet branches can be located on the substrate so as to receive the particles from a focused stream line and/or from the single localized stream. In some embodiments, the channel can have a rectangular cross-section. In other embodiments, the rectangular channel can have a width of less than or equal to about 1000 micrometers, 650 micrometers, 100 micrometers, 80 micrometers, 65 micrometers, 50 micrometers, 20 micrometers, and/or 10 micrometers.

In any of the aspects, embodiments can include those in which particles are cells, including mammalian cells, blood cells, tumor cells, and/or bacteria cells. In addition, the aspect ratio of the rectangular cross-section can result in the focusing of particles into two streams. Focusing of particles into one or more localized stream lines can space the particles approximately evenly longitudinally. In some embodiments, the aspect ratio of a first rectangle dimension to a second rectangle dimension can be between approximately 0.3 and 0.8. In other embodiments, the aspect ratio can be approximately 1 to 2.

In the enumerated aspects or in any of their embodiments, the system can include at least one channel that curves and is symmetric and sigmoidal. In other embodiments, the channel can be asymmetric and sigmoidal. The location of the focused stream within the channel can depend upon inertial forces and Dean drag forces acting on the particles. The location can further depend upon centrifugal forces acting on the particles. A Dean number for flow through the channel can be less than or equal to about 20. In some embodiments of the system, the radius of curvature can vary and/or can change after each inflection of the curve. A cross sectional dimension of the channel can vary and can change after each inflection of the curve. In one embodiment, the channel can form a spiral.

In other embodiments, a plurality of channels can be provided on the substrate and at least some of the channels can be configured to allow serial flow. A plurality of channels can be provided on the substrate and a first channel can have first and second output branches leading to second and third channels respectively. At least two of the channels can be configured to focus particles of different predetermined diameters. The system can include a detector for detecting and enumerating particles in the one or more focused stream lines and for detecting and enumerating particles in the single localized stream. The system can further include a tagging system for tagging selected particles with a tag that can be detected by the detector, the detector thereby detecting and enumerating the selected particles. In any and all aspects, embodiments can include systems in which the focusing can result exclusively from the inertial forces. Other embodiments can include systems in which the focusing can result from inertial and other forces.

In any of the aspects, further embodiments can include methods for focusing particles in which the fluid flow through the channel is laminar and wherein the Reynolds Number of the fluid flow is between about 1 and 250. Focusing can produce a localized flux of particles enriched in a first particle based on particle size. A first particle diameter divided by a hydraulic diameter of the channel can be greater than or equal to about 0.07 and the first particle diameter divided by the hydraulic diameter of the channel can be less than or equal to about 0.5. In some embodiments, the channel has a rectangular cross-section, a height, a width, and a hydraulic diameter equal to 2*height*width/(width+height) and the rectangular cross-section has an aspect ratio of between approximately 0.3 and 0.8 and/or approximately 1 to 2.

In the enumerated aspects or in any of their embodiments, methods for focusing particles can include applying an asymmetric force to the particles to produce one to three localized fluxes of particles. The asymmetric force can include, but is not limited to, centrifugal, hydrodynamic drag, electrical, magnetic, thermal, sonic, optical, or dielectrophoretic forces. In some embodiments, the asymmetric force can include a Dean drag force that is equal to or greater than about 0.5 nN. Particles can include, but are not limited to, cells, beads, viruses, organelles, nanoparticles, and molecular complexes. Cells can include, but are not limited to, bacterial cells, blood cells, cancer cells, tumor cells, mammalian cells, protists, plant cells, and fungal cells.

In any of the aspects, embodiments can also include methods for focusing particles in which the channel is curved and wherein a Dean number of the moving fluid is less than or equal to about 20. The curved channel can be sigmoidal and/or spiral. In other embodiments, the curved channel can be sigmoidal and asymmetric and the radius of curvature can vary from one inflection point in the sigmoidal curve to a next inflection point in the sigmoidal curve. In some embodiments, a first radius curve can be followed by a larger radius curve. The first radius curve can apply a Dean drag that is about eight times greater than a Dean drag applied in the larger radius curve. In other embodiments, the channel can have a rectangular cross-sectional shape and at least one dimension of the rectangular cross-sectional shape can vary from inflection point to inflection point in the sigmoidal curve.

In the enumerated aspects or in any of their embodiments, methods for focusing particles can include passing the moving fluid from the channel into at least two output branches wherein one of the output branches is located so as to receive the localized flux of particles enriched in first particles of a given size. Receiving the localized flux can thereby increase the concentration of first particles in solution. In some embodiments, the method can include passing the moving fluid from the channel into at least two output branches wherein one of the output branches is located so as to receive the localized flux of particles enriched in first particles of a given size. A detector can be applied to enumerate particles traveling in the localized flux of particles in the channel. Methods can further include a tagging system for tagging selected particles with a tag that can be detected by the detector, the detector thereby detecting and enumerating the selected particles. In any and all aspects, methods can include systems in which the focusing can result exclusively from the inertial forces. Other method embodiments can include systems in which the focusing can result from inertial and other forces.

In any of the aspects, embodiments can include an apparatus wherein the cross sectional shape and area of the channel can be consistent from the inlet to the outlet. In other embodiments, the cross sectional shape and area of the channel can vary from the inlet to the outlet. The one or more localized stream lines can have a width that is less than or equal to about five times, four times, three times, two times, and/or 1.05 times the predetermined particle size. Moving the fluid suspension having particles of a predetermined size from the inlet to the outlet focuses the particles of a predetermined size into four localized streams, two localized streams, and/or a single localized stream.

In the enumerated aspects or in any of their embodiments, the apparatus can further include at least first and second outlet branches formed at an outlet portion of the channel, at least one of the first and second outlet branches being located on the substrate so as to receive the particles of a predetermined size from the single localized stream. In some embodiments, the aspect ratio of the rectangular cross-section results in the focusing of particles into two streams. Further, the focusing of particles into one or more localized stream lines can space the particles approximately evenly longitudinally. In other embodiments, the location of the focused stream depends upon inertial forces and Dean drag forces acting on the particles. The location can further depend upon centrifugal forces acting on the particles.

In any of the aspects, embodiments can include an apparatus wherein a cross sectional dimension of the channel varies. In some embodiments, the cross sectional dimension of the channel changes after each inflection of the curve. A plurality of channels can be provided on the substrate and can be configured to allow parallel flow. In other embodiments, a plurality of channels can be provided on the substrate, and at least some of the channels can be configured to allow serial flow. A plurality of channels can be provided on the substrate and a first channel can have first and second output branches leading to second and third channels respectively. At least two of the channels can be configured to focus particles of different predetermined diameters.

In the enumerated aspects or in any of their embodiments, the system can further include a tagging system that can be a passive sorting system. The tagging system can apply to the particles to be segregated a tag having a property that can be forced out of the focused particle stream by the sorting system. The tag can increase the particle size and the sorting system can include a channel geometry that segregates particles into the first and second output branches based upon size. In some embodiments, the tag can include a magnetic property and the sorting system can include a magnetic biasing element that applies a force to the tagged particles that diverts the tagged particles from the second to the first output branch. In other embodiments, the tag can include an electric property and the sorting system can include an electrophoretic force to the tagged particles that diverts the tagged particles from the second to the first output branch. The sorting system can include an affinity column that diverts the tagged particles from the second to the first output branch.

In any of the aspects, embodiments can include a sorting system which is an active sorting system and can further include a controller for selectively diverting tagged particles from the second to the first output branch. The sorting system can further include a detector for detecting tagged particles, the detector being operatively connected to the controller to signal to the controller the presence of a tagged particle for diversion. The detector can be a fluorescence detector and the tags can be fluorescent tags.

In any of the aspects, certain embodiments of the sorting system can further include a channel resistance actuator, the channel resistance actuator being selectively actuated by the controller to divert tagged particles from the second to the first output branch. The channel resistance actuator can be coupled to the first output branch to lower the fluid resistance of the first output branch to divert a tagged particle from the second to the first output branch. In some embodiments, the channel resistance actuator can be coupled to the second output branch to increase the fluid resistance of the first output branch to divert a tagged particle from the second to the first output branch. The channel resistance actuator can be a microvalve that partially opens or closes to change the fluid resistance of an output branch. In other embodiments, the channel resistance actuator can stretch or squeeze a dimension of the channel to change the fluid resistance of an output branch. In any of the aspects, the particles can be cells and the cells can be sorted based upon a property of the cell. In some embodiments, the property of the cell for which it is sorted is the presence of at least one indicator of cancer.

In the enumerated aspects or in any of their embodiments, methods for separating target particles from a population of particles can be provided wherein the dividing is done passively. The target particles can have a different size than other particles in the population and the target particles can form a localized flux in a predetermined location within the channel. In some embodiments, an entrance to the first output branch can be located so as to encompass the predetermined location within the channel of the localized flux of target particles. Embodiments of the method can also include selectively tagging particles with a tag that is used by a dividing system operatively connected to the channel. The tag can increase the size of the selectively tagged particles and the tag can be a magnetic tag.

In any of the aspects, embodiments can further include methods wherein the dividing system employs a magnetic field to direct target particles to the first output branch and other particles to the second output branch. The method can include detecting tags or tagged particles by the dividing system, and diverting by the dividing system of tagged particles into a selected one of the first and second output branches. The dividing system can include a detector operatively connected with the channel, a fluid resistance varying element operatively connected to at least one of the first and second output branches, and a controller in communication with the detector and the fluid resistance varying element. In some embodiments, dividing an output from the channel can include detecting tagged particles by the detector, communicating information regarding the detection from the detector to the controller, and signaling by the controller to the fluid resistance varying element to vary the fluid resistance in at least one of the first and second output branches so as to cause the tagged particle to flow into a selected one of the output branches.

In the enumerated aspects or in any of their embodiments, the population of particles can include, but is not limited to, cells, beads, viruses, organelles, nanoparticles, and molecular complexes. In some embodiments, the target particles can be cells and the channel can be curved. In other embodiments, the first radius curve of the channel can apply a Dean drag that is about eight times greater than a Dean drag applied in the larger radius curve. The channel can have a rectangular cross-sectional shape and at least one dimension of the rectangular cross-sectional shape can vary from inflection point to inflection point in the sigmoidal curve.

BRIEF DESCRIPTION OF THE DRAWINGS

The invention will be more fully understood from the following detailed description taken in conjunction with the accompanying drawings, in which:

FIG. 11D is a side view of the channel of FIG. 11A showing particle focusing at various locations along a length of the channel;

FIG. 22 is a side view of exemplary channels illustrating focusing for various $a/D_h$;

FIG. 23C is a top view of a tree configuration for a multi-channel exemplary focusing system;

FIG. 27 illustrates purity and yield data for filtration of large particles from 3.1-µm particles;

FIG. 28 illustrates data for an exemplary focusing system having cascaded separations with two tiers;

FIG. 36 is a side view illustrating particle focusing behavior for various $R_e$ within an exemplary focusing system;

FIG. 39 is side view illustrating focusing behavior for exemplary channels of various widths within an exemplary focusing system;

FIG. 40 is a side view illustrating focusing behavior for exemplary channels of various widths within an exemplary focusing system;

FIG. 41 is a representation of focusing behavior for exemplary channels of various widths within an exemplary focusing system;

FIG. 42 is a representation of focusing behavior for exemplary channels of various widths within an exemplary focusing system;

FIG. 44 is a top view illustrating the focusing of blood cells within an exemplary focusing system;

DETAILED DESCRIPTION OF THE INVENTION

Figure 1A:
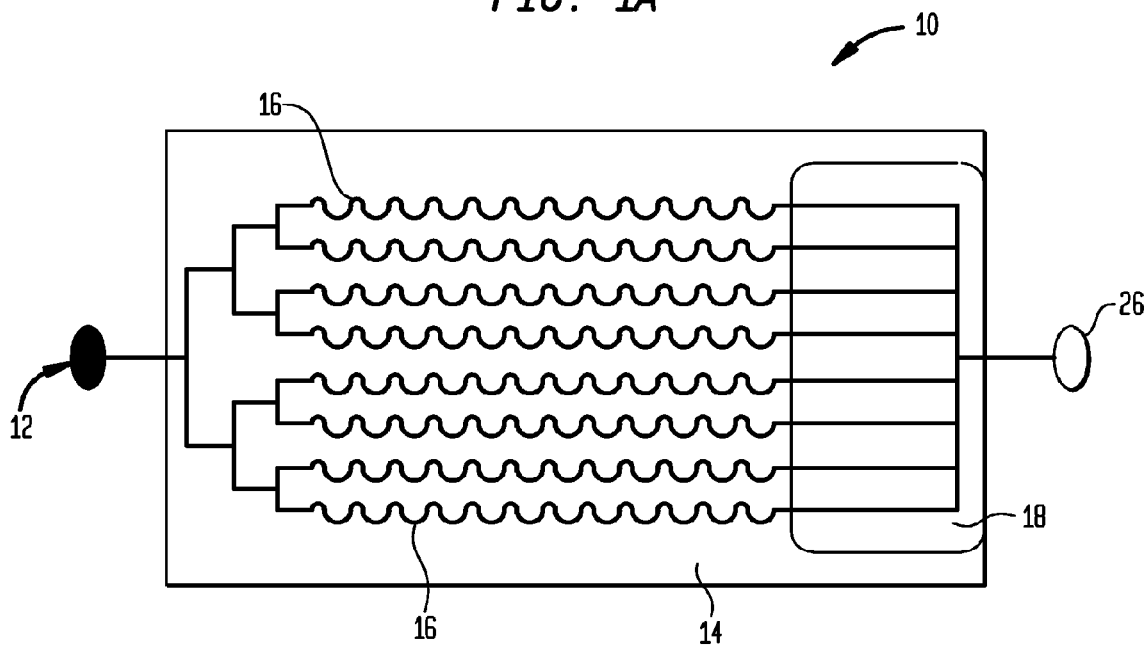
FIG. 1A illustrates one embodiment of a system for the separation, ordering, and focusing of particles within microchannels.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The invention relates to the fields of microfluidics and analyte separation. Various embodiments of the invention described below are based upon the notion that laminar flow of a fluid through microfluidic channels can result in the continuous and accurate self-ordering of particles suspended within the fluid. A variety of specific channel geometries are illustrated that take advantage of this effect to create continuous streams of ordered particles constrained in three spatial dimensions. Particles order laterally within the x-y plane (or cross-sectional plane) of the channel and can also order longitudinally along the direction of flow. An additional dimension of rotational ordering can occur for asymmetrically shaped particles.

In general, the invention features methods and devices that separate and focus streams of particles to equilibrium positions within a channel flow field based, at least in part, on inertial lift forces. In rectangular channels, this can lead, for example, to four streams of focused particles spaced a distance apart from a center of each of the four rectangular faces. For certain rectangular geometries, this four-fold symmetry can be reduced to a two-fold symmetry, with streams of particles spaced apart from each of two opposed faces of the channel.

The invention can also include methods and structures that decrease the symmetry of the system using a variety of forces, including, for example, electromagnetic, magnetic, centrifugal, hydrodynamic, thermal, sonic, optical, and/or dielectrophoretic forces or combinations thereof. Although any force may be used to bias a particular potential minimum within the channel flow field, utilizing centrifugal forces with a curved channel structure has certain advantages. In this case, the force will increase with the square of the flow rate based only on a minor geometric change with no additional mechanical or electrical parts required. For example, the symmetry may be reduced by using inertial forces inherent in the flow through an S-shaped rectangular channel to result in a two-fold symmetry (down from four-fold) with a majority of the particles aligned with the flow in a periodic manner not corresponding to the period of the underlying channel. The geometry of the channel may also be used to change symmetry either by changing the radius of curvature or the width of the channel in a periodic manner (the channels thus curving asymmetrically) to create a single focused particle stream.

Embodiments of the invention may be advantageous in that they may employ a single stream input and require no moving parts or separate pressure control. Embodiments of the invention can also provide methods that are low cost and employ devices requiring simple, fault tolerant manufacture that may also be miniaturized. Embodiments of the invention may be operated continuously and at high volumetric flow rates with cascading outputs. The invention also requires no interactions with mechanical filters or obstacles and requires very low maintenance.

The principles relating to suspended particles are also applicable to a variety of biological materials, particularly to cells. The ability to rapidly analyze and extract information from whole blood, for example, and its component cells is of great importance for medical diagnostics and applications in basic science. Blood cells themselves contain an abundance of information relevant to disease, infection, malignancy, or allergy diagnosis. Systems and principles are presented herein related to inertial microfluidic technology as a solution for high-throughput and precise microscale control of cell and particle motion. Systems of the invention are ideally suited for applications in blood cell subtype or rare cell enumeration, sorting, and analysis. Identification and analysis of rare cells, in particular, requires large sample sizes and high-throughput. Rapid and simple microfluidic techniques presented herein can surpass the limitations of conventional sorting techniques that limit the size of samples that can be analyzed. The ability to sort, order, enumerate, and analyze particles continuously, differentially, and at high rates in a simple channel will be broadly applicable in a range of applications in continuous bio-particle separation, high-throughput cytometry, and large scale filtration systems.

Figure 1B:
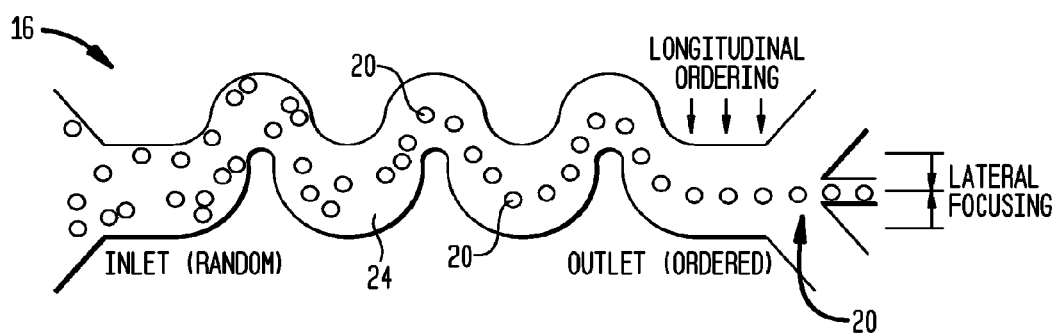
FIG. 1B illustrates an example of one microchannel of FIG. 1A.

While there are many configurations possible in a system for the self-ordering of particles within microfluidic channels, one embodiment of such a system 10 is illustrated in FIGS. 1A and 1B. As shown, the system 10 generally includes an inlet 12 that can be configured for introducing a sample 24 having suspended particles 22 into the system. A microfabricated chip 14 can be provided and can have at least one microfluidic channel 16 formed therein for receiving the sample 24 and for ordering and focusing the particles 22 suspended in the sample 24, as shown in FIG. 1B. A plurality of such channels 16 situated in parallel are formed in the exemplary chip 14 illustrated in FIG. 1A.

The plurality of channels 16 formed in the chip 14 can have numerous configurations which will be described in detail below. In general, however, the plurality of channels 16 can have a specified geometry configured to separate, order, and focus particles of a predetermined size suspended within the sample 24 such that one or more focused streams of particles 22 per channel 16 are provided at an output 26 of the chip 14. An analysis region 18 can be provided in proximity to the output 26 of the channels 16 to monitor, sort, count, image, or otherwise analyze the localized and focused streams of particles 22.

In one embodiment, chip 14 can be, or be part of, a particle enumerating system. In particular, analysis region 18, in which the particles have been focused and ordered, could be subject to interrogation by a detector for the purpose of counting the particles. A variety of detectors are discussed below, as are systems for tagging particles for detection, and these elements can also be used for enumeration.

As used herein, a "sample" must be capable of flowing through the microfluidic channels of the system embodiments described. Thus, any sample consisting of a fluid suspension, or any sample that be put into the form of a fluid suspension, that can be driven through microfluidic channels can be used in the systems and methods described herein. For example, a sample can be obtained from an animal, water source, food, soil, air, etc. If a solid sample is obtained, such as a tissue sample or soil sample, the solid sample can be liquefied or solubilized prior to subsequent introduction into the system. If a gas sample is obtained, it may be liquefied or solubilized as well. The sample may also include a liquid as the particle. For example, the sample may consist of bubbles of oil or other kinds of liquids as the particles suspended in an aqueous solution.

Any number of samples can be introduced into the system for particle focusing and should not be limited to those samples described herein. A sample can generally include any suspensions, liquids, and/or fluids having at least one type of particle, cellular, droplet, or otherwise, disposed therein. Further, focusing can produce a flux of particles enriched in a first particle based on size. In some embodiments, a sample can be derived from an animal such as a mammal. In a preferred embodiment, the mammal can be a human. Exemplary fluid samples derived from an animal can include, but are not limited to, whole blood, sweat, tears, ear flow, sputum, bone marrow suspension, lymph, urine, brain fluid, cerebrospinal fluid, saliva, mucous, vaginal fluid, ascites, milk, secretions of the respiratory, intestinal and genitourinary tracts, and amniotic fluid. In other embodiments, exemplary samples can include fluids that are introduced into a human body and then removed again for analysis, including all forms of lavage such as antiseptic, bronchoalveolar, gastric, peritoneal, cervical, athroscopic, ductal, nasal, and ear lavages. Exemplary particles can include any particles contained within the fluids noted herein and can be both rigid and deformable. In particular, particles can include, but are not limited to, cells, alive or fixed, such as adult red blood cells, fetal red blood cells, trophoblasts, fetal fibroblasts, white blood cells, epithelial cells, tumor cells, cancer cells, hematopoeitic stem cells, bacterial cells, mammalian cells, protists, plant cells, neutrophils, T lymphocytes, CD4+, B lymphocytes, monocytes, eosinophils, natural killers, basophils, dendritic cells, circulating endothelial, antigen specific T-cells, and fungal cells; beads; viruses; organelles; droplets; liposomes; nanoparticles; and/or molecular complexes. In some embodiments, one or more particles such as cells, may stick, group, or clump together within a sample. In such a configuration, a grouping or clumping of particles can be considered to be "a particle" for the purposes of systems of the invention. More particularly, a grouping or clumping of particles may act and be treated as a single particle within channels of the invention described herein and can thus be sorted, ordered, separated, and focused in the same way as a single particle.

Non-biological samples can include, for example, any number of various industrial and commercial samples suitable for particle separating, ordering, and focusing. Exemplary industrial samples that can be introduced into the system can include, but are not limited to, emulsions, two-phase chemical solutions (for example, solid-liquid, liquid-liquid, and gas-liquid chemical process samples), waste water, bioprocess particulates, and food industry samples such as juices, pulps, seeds, etc. Similarly, exemplary commercial samples can include, but are not limited to, bacteria/parasite contaminated water, water with particulates such as coffee grounds and tea particles, cosmetics, lubricants, and pigments.

In some embodiments, a fluid sample obtained from an animal is directly applied to the system described herein, while in other embodiments, the sample is pretreated or processed prior to being delivered to a system of the invention. For example, a fluid drawn from an animal can be treated with one or more reagents prior to delivery to the system or it can be collected into a container that is preloaded with such a reagent. Exemplary reagents can include, but are not limited to, a stabilizing reagent, a preservative, a fixant, a lysing reagent, a diluent, an anti-apoptotic reagent, an anti-coagulation reagent, an anti-thrombotic reagent, magnetic or electric property regulating reagents, a size altering reagent, a buffering reagent, an osmolality regulating reagent, a pH regulating reagent, and/or a cross-linking agent. Examples of methods for processing fluid samples for delivery to an analytical device are described in U.S. Publication No. 2007/0196820 entitled, "System For Delivering a Diluted Solution" filed Mar. 3, 2004 and incorporated herein by reference in its entirety.

Particles suspended within a sample can have any size which allows them to be ordered and focused within the microfluidic channels described herein. For example, particles can have a hydrodynamic size that is in the range of about 40 microns to about 0.01 microns. More preferably, particles can have a hydrodynamic size that is in the range of about 20 microns to about 0.1 microns. More preferably, particles can have a hydrodynamic size that is in the range of about 10 microns to about 1 micron. It will be appreciated that particle size is only limited by channel geometry, and particles both larger and smaller than the above-described ranges can be ordered and focused within predetermined channel geometries having laminar flow conditions.

In another aspect of the system, a particle to volume ratio of the sample can optionally be manipulated or adjusted for conservation of mass within the channels. In general, sorting, ordering, and focusing of particles is in-part dependent on interparticle spacing within channels as well as the ratio of particle size to hydrodynamic size of the channel. Various channel geometries described herein may require a predetermined particle to volume ratio of the particle to be focused in order to achieve a required interparticle spacing and thereby maintain ordering and focusing of that particle. In particular, the particle to volume ratio of a particle suspended within a fluid can be calculated and adjusted as needed to achieve focusing within certain channel geometries. In general, a maximum particle to volume ratio for a specified particle size and channel geometry can be determined using the formula:

$$\text{MaxVolumeFraction} = \frac{2N\pi a^2}{3hw},$$

where N is the number of focusing positions in a channel, a is the focused particle diameter, h is the channel height, and w is the channel width. Thus, samples can be diluted or concentrated to attain a predetermined ratio before and/or during introduction of the sample into the system. Additionally, certain exemplary systems may require the ratio to be adjusted after the sample is introduced into the channels.

Particle to volume ratios of a sample within the channels described herein can have any value sufficient to enable ordering and focusing of particles. In general, the particle to volume ratio can be less than about 50%. In other embodiments, particle to volume ratios can be less than about 40%, 30%, 20%, 10%, 8%, or 6%. More particularly, in some embodiments, particle to volume ratios can be in a range of about 0.001% to about 5%, and can preferably be in a range of about 0.01% to about 4%. More preferably the ratio can be in the range of about 0.1% to about 3%, and most preferably in the range of about 0.5% to about 2%. As will be appreciated by those skilled in the art, the particle to volume ratio of additional or extraneous particles within the sample, apart from the particle to be focused, need not necessarily be considered or adjusted. As will be further appreciated by those skilled in the art, any number of samples may not require any adjustment to the particle to volume ratio of the particle to be focused before, during, and/or after introduction into the system.

Various commonly used techniques for diluting or concentrating samples for adjusting a particle to volume ratio can be used in the embodiments disclosed herein. For example, a sample can be diluted or concentrated in batches before introduction into the system such that the sample ultimately introduced into the system has the required ratio before being introduced through the inlet. In other embodiments, the system can include two or more inlets for introducing the sample simultaneously with a diluent or concentrate to effect dilution or concentration. In this way, the particle to volume ratio can be adjusted within the system, whether adjustment occurs within a chamber before the sample and diluent or concentrate enter the channels or whether adjustment occurs through mixing of the sample and the diluent or concentrate within the channels. In another embodiment, the diluent or concentrate can be introduced into a center portion, fork, or branch of a channel as may be required by various applications after the unadjusted sample has traveled within the channel for some distance. A person skilled in the art will appreciate the variations possible for adjusting the particle to volume ratio of a sample within the embodiments described herein.

Referring again to FIGS. 1A and 1B, one or more microfluidic channels 16 can be formed in the microfabricated chip 14 and can be configured for receiving the sample 24 via one or more inlets 12 in communication with the channels 16. The channels 16 can be further configured for ordering and focusing particles of a predetermined size suspended within the sample into one or more localized streams or fluxes of particles 22 that is directed into one or more outlets 26. In this way, particles in a dilute solution can be concentrated as illustrated in the figure. As illustrated in FIG. 1B, the localized flux 22 can include three or more particles 20 disposed longitudinally adjacent to one another and can be separated by a substantially constant longitudinal distance. Particles 20 within the flux 22 can also align rotationally relative to the channel 16.

In general, "localization" refers to a reduction in the area of a cross-section of a channel through which a flux of particles passes. In some preferred embodiments, particles can be localized within an area having a width of, at most, 1.05, 2, 3, 4, or 5 times the width of the particles. Localization can occur at any location within the channel, but preferably occurs within an unobstructed portion of the channel. For example, localization can occur in a portion of the channel having less than 50%, 40%, 30%, 20%, 10%, 5%, 2%, 1%, or 0.1% reduction in cross-sectional area. In certain embodiments, localization can occur in a channel having a substantially constant cross-sectional area.

Any number of microfluidic channels can be formed in the chip in any number of ways, described in detail below. In one exemplary embodiment, a single channel is formed on the chip for focusing particles therein. In other exemplary embodiments, a plurality of channels can be formed in the chip in various configurations of networks for focusing particles. For example, 2, 4, 6, 8, 10, 12, and more channels can be formed in the chip. As shown in FIG. 1A, a tree configuration is particularly convenient for a multiple channel system. Any number of layers can also be included within a microfabricated chip of the system, each layer having multiple channels formed therein.

Various channel geometries can be included on a single chip. As shown in FIG. 1A, straight sections of channels are formed in the chip near the inlet for transporting and dividing flow lines as the sample is introduced into the system. The straight sections of channel can transition to any number of symmetric and/or asymmetric curved channels for focusing particles of a predetermined size as needed. As further shown in FIG. 1A, the chip can also include straight sections of channels at an output region for analysis of focused particles, collection of focused particles, and/or for recombining stream lines. As will be appreciated by those skilled in the art, any number of curves or straight sections can be included as needed within the chip. Additional curved sections of channels can serve as "off-ramps" for focused particle streams to facilitate additional separation based on labels or tags associated with the particles. Channel forks or splits can be included at any positions within the channels to further facilitate manipulation of focused particles as needed for various applications.

Various channel dimensions can also be included within a single chip. Channel dimensions can decrease over the length of the chip to facilitate filtering of the sample, or for other reasons specific to an application. Channel dimensions can be larger at the input area or at the output area to enable forks or valve systems to be positioned within the channels, or to enable multiple stream lines to be separated and directed to different locations for analysis or collection. In a similar way, cross-sections of various channels can also be changed as needed within a single chip to manipulate stream lines of focused particles for particular applications. In general, any combination of channel geometries, channel cross-sections, and channel dimensions can be included on a single chip as needed to sort, separate, order, and focus particles of a predetermined size or particles of multiple predetermined sizes.

The channels used in the systems described herein can have various geometries and cross-sections for focusing particles of a predetermined size suspended within a fluid. For example, in one embodiment illustrated in FIGS. 2A and 2B, a straight channel 30 is provided having a rectangular cross-section with an aspect ratio of substantially 1 to 1. As will be described in more detail below, particles of a predetermined size flowing within such a channel geometry will be separated, ordered, and focused into four streamlines $32a$, $32b$, $32c$, $32d$ corresponding to four equilibrium points or potential minimums at a distance from each face of the four channel walls. In another embodiment, a straight channel 36 is provided having a rectangular cross-section with an aspect ratio of substantially 2 to 1. Particles of a predetermined size flowing within such a channel geometry can be separated, ordered, and focused into two focused streamlines $38a$, $38b$ corresponding to two equilibrium points or potential minimums along top and bottom walls across the width of the channel. In one embodiment, an aspect ratio of 1 to 2 can also be used.

Figure 3A:
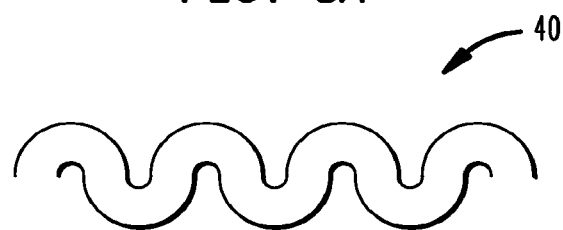
FIG. 3A is a side-view of one embodiment of a symmetrically curved channel for the separation, ordering, and focusing of particles.
Figure 3B:
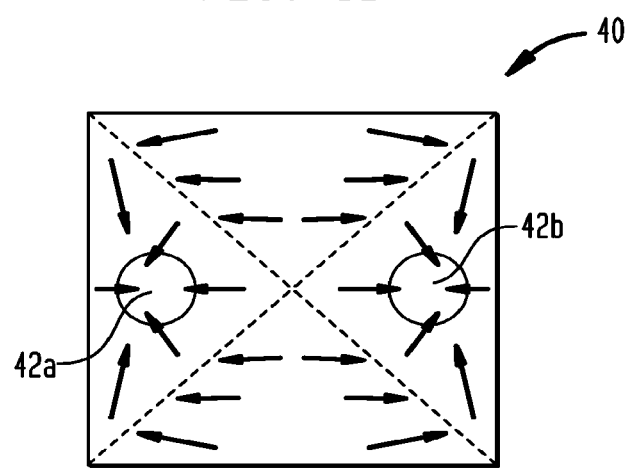
FIG. 3B is a cross-sectional view of the symmetric channel of FIG. 3A showing two equilibrium positions for focused streams of particles.

The channels may also be curved as shown in FIGS. 3A and 3B. For example, symmetrically curved channels can be provided such as S-shaped, sinusoidal, or sigmoidal shaped channel 40 having a rectangular cross-section. Particles of a predetermined size flowing within such a channel geometry will be generally focused into two streamlines $42a$, $42b$ corresponding to two equilibrium points or potential minimums at a distance from left and right side faces of the channel. An aspect ratio of a sigmoidal channel 40 can be substantially 1 to 1 and/or can vary along a length thereof. For example, the aspect ratio of a sigmoidal channel can vary over the length of the channel between 1 to 1 and 2 to 1 depending on the configuration chosen.

Figure 4A:
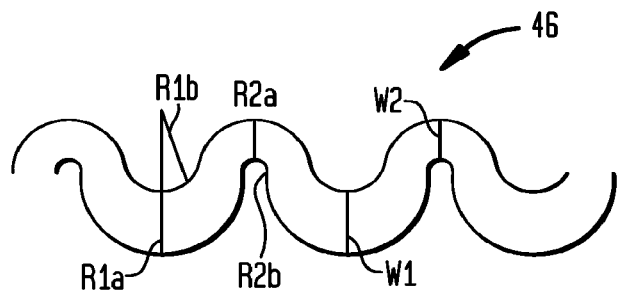
FIG. 4A is a side-view of one embodiment of an asymmetrically curved channel for the separation, ordering, and focusing of particles.
Figure 4B:
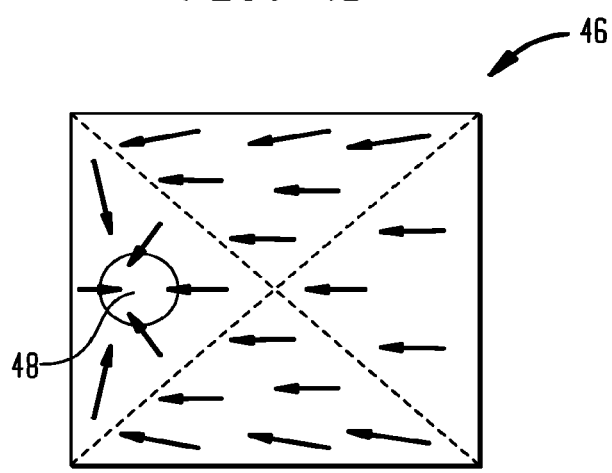
FIG. 4B is a cross-sectional view of the asymmetric channel of FIG. 4A showing one equilibrium position for focused streams of particles.
Figure 4C:
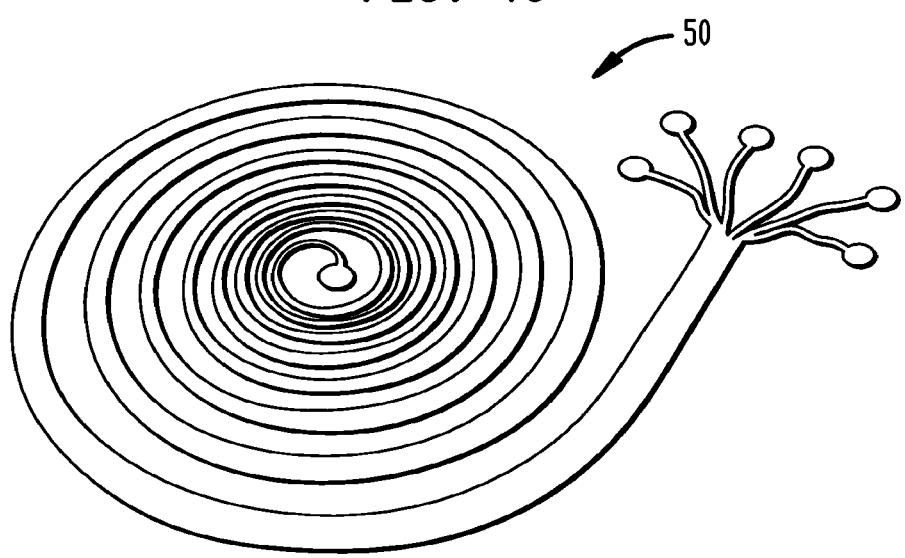
FIG. 4C is a perspective view of another embodiment of an asymmetrically curved channel in the form of an expanding spiral channel.

In another embodiment, asymmetrically curved channels are provided as shown in FIGS. 4A and 4B. While asymmetrically curved channels can have various shapes and configurations as needed for a particular application, in one embodiment an asymmetric channel 46 can generally have the shape of a wave having large and small turns, where a radius of curvature can change after each inflection point of the wave. Each large and small turn can have a specified width of the channel associated with the turn. In particular as shown in FIG. 4A, one-half of a wavelength of the wave can have a large curve with a radius $R_{1a}$, $R_{1b}$ defining a width $W_1$. A second half of the wavelength can have a curve with a radius $R_{2a}$, $R_{2b}$ defining a width $W_2$, where $R_{1a}$ and $R_{1b}$ can be greater than $R_{2a}$ and $R_{2b}$, and vice versa (and where $R_{1a}=R_{2a}$ and $R_{1b}=R_{2b}$ would be a sinusoidal, symmetric shaped channel as indicated above). In addition, $W_1$ can be greater than $W_2$, and vice versa. The wavelength having a first half with the radius $R_{1a}$, $R_{1b}$ and the second half with the radius $R_{2a}$, $R_{2b}$ can then be repeated as many times as needed, varying after each inflection point, to provide a specified length of channel with an asymmetric curve. The asymmetrically curved channel 46 can also have a rectangular cross-section with an aspect ratio that can vary as needed over the channel length depending on the nature of the asymmetry in the curves. In one embodiment, the aspect ratio can vary between 1 to 1 and 2 to 1. In this case, a single focused stream 48 of particles is created corresponding to a single equilibrium point or potential minimum within the channel 46. In other embodiments, asymmetric curving channels, in particular an expanding spiral shaped channel 50 can be provided as shown in FIG. 4C, having a rectangular cross-section with an aspect ratio of substantially 2 to 1, although the aspect ratio can vary. In this case, particles are focused into a single stream line a distance away from an inner wall of the channel corresponding to a single equilibrium point or potential minimum within the channel.

Aspect ratios of all channels described above and herein, including straight, symmetric, and asymmetric, can vary as needed from one application to another and/or as many times as needed over the course of a channel. In embodiments illustrated in FIG. 4, aspect ratios are shown as 1 to 1 and 2 to 1, however, a person of ordinary skill will recognize that a variety of aspect ratios could be employed. In addition, the choice of width to height as the standard for determining the aspect ratio is somewhat arbitrary in that the aspect ratio can be taken to be the ratio of a first cross-sectional channel dimension to a second cross-sectional channel dimension, and for rectangular channels this would be either width to height or height to width. By way of further example, the aspect ratio of the channel of FIG. 4C could be expressed as either 2 to 1 or 1 to 2, as could the aspect ratio of the channel illustrated in FIG. 9A in which the height is twice the width.

Other channel cross-sections can also be included in each of the geometries noted above. Channel cross-sections can include, but are not limited to, circular, triangular, diamond, and hemispherical. Particles of a predetermined size can be focused in each of these exemplary cross-sections, and the equilibrium positions will be dependent on the geometry of the channel. For example, in a straight channel having a circular or hemispherical cross-section, an annulus or arc of focused particles can be formed within the channel. In a straight channel having a triangular or diamond cross-section, particles can be focused into streamlines corresponding to equilibrium positions at a distance from the flat faces of each wall in the geometry. As symmetric and asymmetric curving channels are included having each of the exemplary cross-sections noted above, focusing streams and equilibrium positions can generally correspond to that described above with respect to the channels having a rectangular cross-section.

In general, there are certain parameters within straight, symmetric, and asymmetric microfluidic channels which lead to optimal ordering and focusing conditions for particles suspended within a sample. These parameters can include, for example, channel geometries, particle size with respect to channel geometries, properties of fluid flow through microfluidic channels, and forces associated with particles flowing within microfluidic channels under laminar flow conditions. It is presently believed that the forces acting on the particles can be referred to as inertial forces, however, it is possible that other forces contribute to the focusing and ordering behaviors. Exemplary inertial forces can include, but are not limited to, inertial lift down shear gradients and away from channel walls, Dean drag (viscous drag), pressure drag from Dean flow, and centrifugal forces acting on individual particles. FIGS. 5A-7 will be used to illustrate concepts associated with these parameters in the theory described below, with FIGS. 5A-5B generally referring to parameters associated with straight channels and FIGS. 6A-7 referring to parameters associated with curving channels. The theory discussed below is meant to be solely descriptive and exemplary and, while the behavior of systems designed using these principles can be predicted using this theory, the theory presented should not be considered as limiting the invention to any of the parameters associated with any of the system embodiments disclosed herein or any particular theory of operation.

In general, inertial lift forces in laminar microfluidic systems, such as those described in the embodiments herein, can act to focus randomly distributed particles continuously and at high rates into a single streamline. Particle geometry dependence can be used to develop systems for high-throughput separations. Channel geometry can be changed to reduce focusing particles from an annulus to four points, to two points, and then to a single point within the channel. Two additional levels of particle ordering can be observed, in particular, longitudinally along the channel length and rotationally (for asymmetric particles). In general, separation, ordering, and focusing is primarily controlled by a ratio of particle size to channel size and the flow characteristics of the system. Advantageously, the focusing is independent of particle density.

Lateral migration of particles in shear flow arises from the presence of inertial lift, attributed mainly to the shear-gradient-induced inertia (lift in an unbounded parabolic flow) that is directed down the shear gradient toward the wall, and the wall induced inertia which pushes particles away from the wall. Particles suspended in fluids are subjected to drag and lift forces that scale independently with the fluid dynamic parameters of the system. Two dimensionless Reynolds numbers can be defined to describe the flow of particles in closed channel systems: the channel Reynolds number ($R_c$), which describes the unperturbed channel flow, and the particle Reynolds number ($R_p$), which includes parameters describing both the particle and the channel through which it is translating.

$$R_c = \frac{U_m D_h}{\nu}$$

and $$R_p = R_c \frac{a^2}{D_h^2} = \frac{U_m a^2}{\nu D}$$

Both dimensionless groups depend on the maximum channel velocity, $U_m$, the kinematic viscosity of the fluid, and $\nu = \mu/\rho$ ($\mu$ and $\rho$ being the dynamic viscosity and density of the fluid, respectively), and $D_h$, the hydraulic diameter, defined as $2wh/(w+h)$ (w and h being the width and height of the channel). The particle Reynolds number has an additional dependence on the particle diameter, a. The definition of Reynolds number based on the mean channel velocity can be related to $R_c$ by $R_e = 2/3\ R_c$.

Figure 5A:
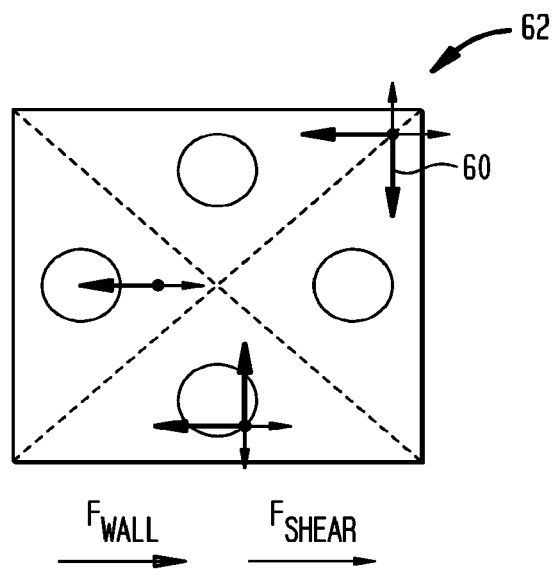
FIG. 5A is a cross-sectional view of one embodiment of a straight channel having a rectangular cross-section showing forces acting on particles within the channel.
Figure 5B:
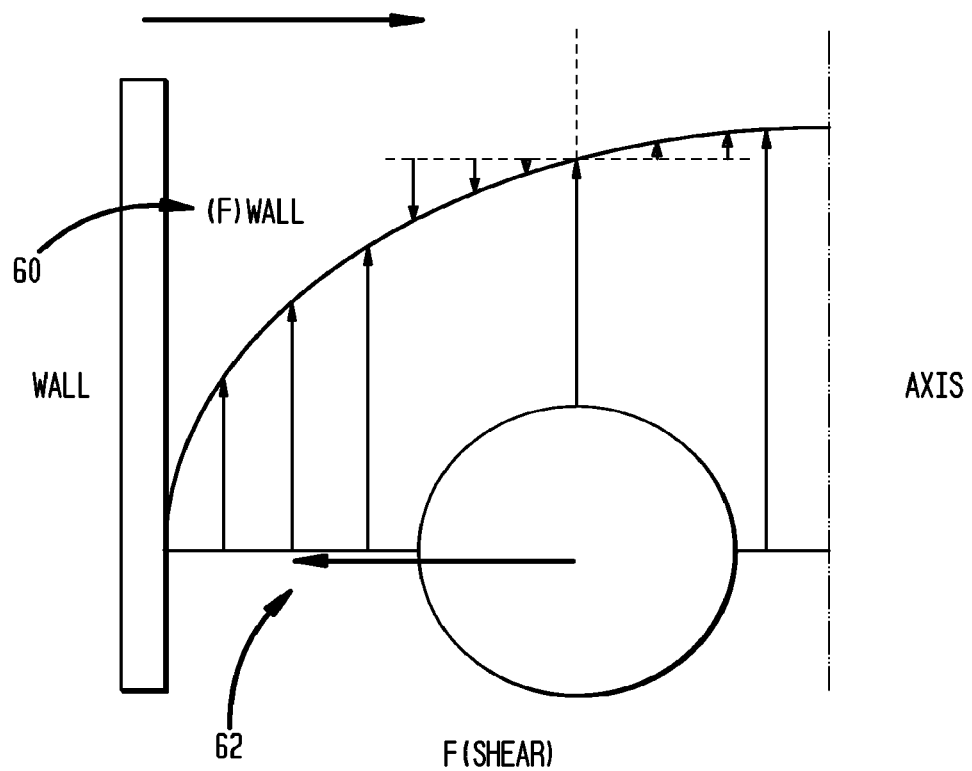
FIG. 5B is a representation of the forces acting on a particle within the straight channel of FIG. 5A.

Inertial lift forces dominate particle behavior when the particle Reynolds number is of order 1. Typically, particle flow in microscale channels is dominated by viscous interactions with $R_p \ll 1$. In these systems, particles are accelerated to the local fluid velocity because of viscous drag of the fluid over the particle surface. Dilute suspensions of neutrally buoyant particles are not observed to migrate across streamlines, resulting in the same distribution seen at the inlet, along the length, and at the outlet of a channel. As $R_p$ increases, migration across streamlines occurs in macroscale systems. In a cylindrical tube, particles were observed to migrate away from the tube center and walls to form a focused annulus. The theoretical basis for this "tubular pinch" effect is a combination of inertial lift forces acting on particles at high particle Reynolds numbers. The dominant forces on rigid particles are the "wall effect," where an asymmetric wake of a particle near the wall leads to a lift force 60 away from the wall, and the shear-gradient-induced lift force 62 that is directed down the shear gradient and toward the wall, as shown in FIGS. 5A and 5B. A relation describing the magnitude of these lift forces ($F_z$) in a parabolic flow between two infinite plates is useful in understanding how the intensity of inertial migration depends on system parameters with the caveat that the derivation assumes $R_p$<1.

$$F_z = \frac{\rho U_m^2 a^4}{D_h^2} f_c(R_c, x_c) = \frac{\mu^2}{\rho} R_p^2 f_c(R_c, x_c)$$

Here $f_c(R_c, x_c)$ can be considered a lift coefficient and is a function that is dependent on both the position of the particle within the cross-section of the channel $x_c$ and the channel Reynolds number, but independent of particle geometry. At the equilibrium position, where the wall effect and shear-gradient lift balance, $f_c$=0.

Inertial lift acting on a particle leads to migration away from the channel center. From the equation for $F_{lift}$, an expression for the particle migration velocity, $U_p$, can be developed assuming Stokes drag, $F_s$=$3\pi\mu a U_p$, balances this lift force:

$$U_p = \frac{\rho U_m^2 a^3}{3\pi\mu D_h^2} f_c(R_c, x_c)$$

An estimate of the transverse migration velocity out from the channel center line can be made by using an average value of $f_c$~0.5 for flow through parallel plates. This calculation yields a value of 3.5 cm/s for 10-μm particles in a flow with $U_m$=1.8 m/s. Traveling a lateral distance of 40 μm requires traveling ~2 mm downstream in the main flow. The previous equation for $U_p$ also indicates that the lateral distance traveled will depend heavily on particle diameter, indicating the possibility of separations based on differential migration.

Figure 6A:
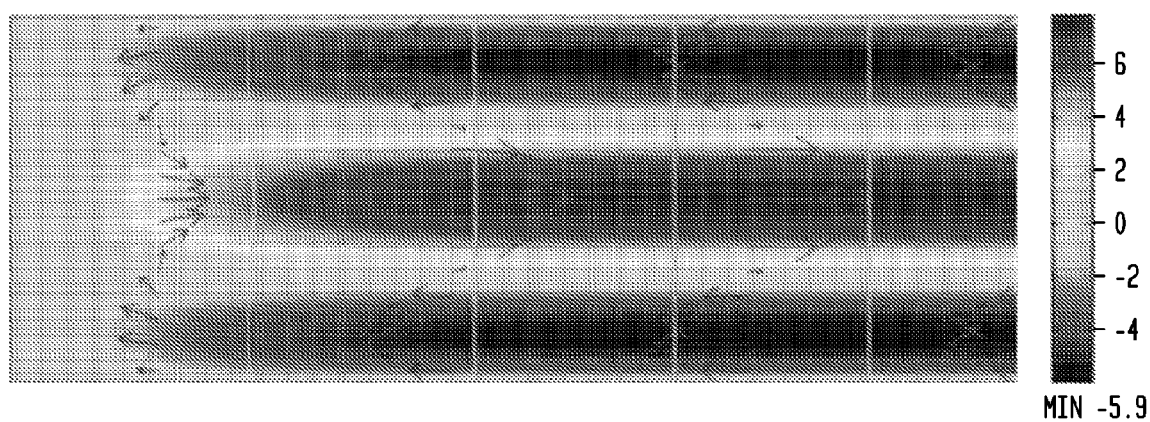
FIG. 6A is a parabolic velocity profile of Dean drag forces acting within a curved microchannel.
Figure 6B:
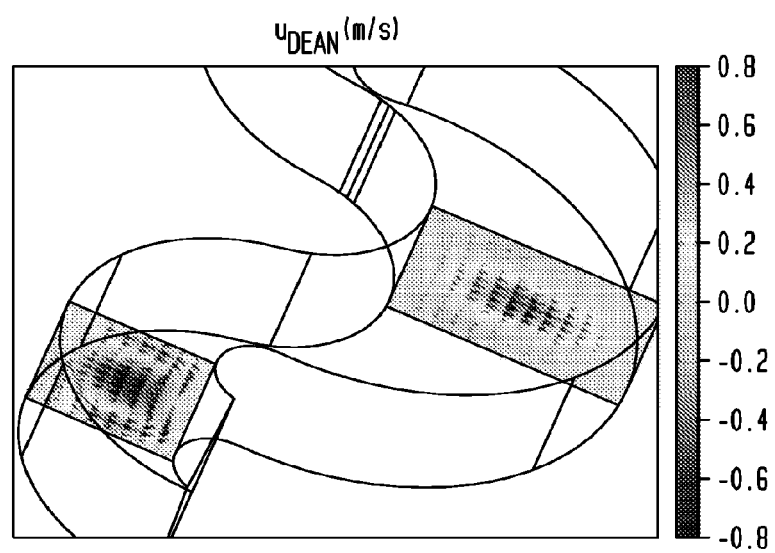
FIG. 6B illustrates Dean flow velocity dependence on Dean number within curving microchannels.
Figure 6C:
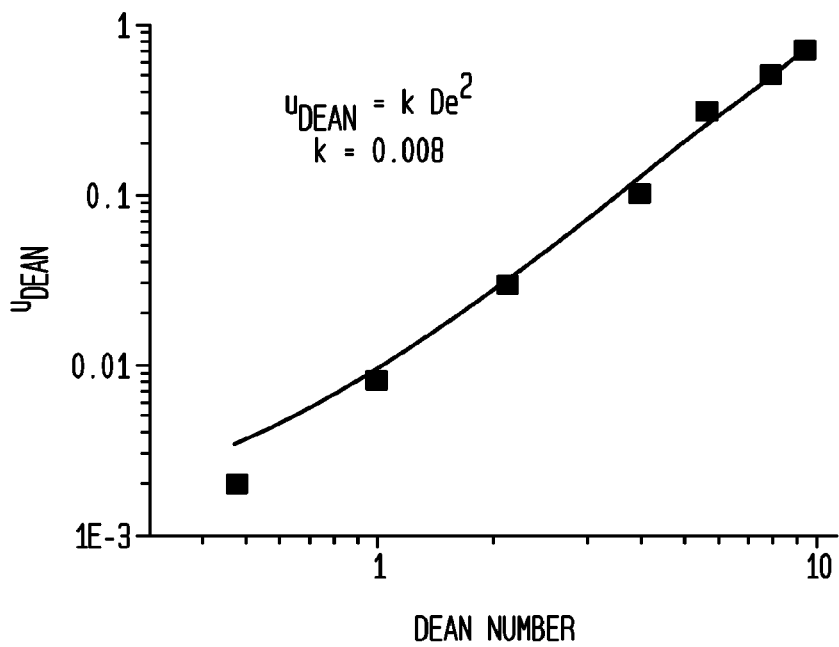
FIG. 6C is a graph illustrating average secondary flow velocity magnitude as a function of changing Dean number for a single channel geometry.

Channels with curvature create additional drag forces on particles. When introducing curvature into rectangular channels, secondary flows develop perpendicular to the streamwise direction due to the nonuniform inertia of the fluid. In a parabolic velocity profile, one example of which is shown in FIG. 6A, faster moving fluid elements within the center of a curving channel can develop a larger inertia than elements near the channel edges. These elements can move toward the channel outer edge, and in order to conserve mass at all points $$\left(\nabla \cdot \rho \vec{V} + \frac{\partial \rho}{\partial t} = 0\right),$$

the fluid is recirculated along the top and bottom of the channel. Two dimensionless numbers can be written to characterize this flow, the Dean number ($D_e$) based on the maximum velocity in the channel, and the curvature ratio (δ). The Dean number, $D_e = R_c (D_h/2r)^{1/2}$ and the curvature ratio, $\delta=D_h/2r$, where r is the average radius of curvature of the channel. For moderate $D_e$<75 observed in the microfluidic systems described herein, the secondary rotational flow, or Dean flow, consists of only two vortices. The velocity magnitude of the Dean flow scales as $U_D \sim \rho D_e^2/(\mu D_h)$ and therefore, Stokes drag on suspended particles due to this secondary flow becomes significant for large $D_e$. In particular, the Dean flow velocity dependence on Dean number can be seen in FIG. 6B. FIG. 6B illustrates a simulation of Dean flow at an average streamwise velocity of 1 m/s, corresponding to a Dean number of ~10. The geometry in FIG. 6B is 50-μm in width at the smaller turn and 80-μm at the larger turn. The main flow is coming out of the page. FIG. 6C is a graph further illustrating average secondary flow (vortex) velocity magnitude as a function of changing Dean number for a single geometry. A quadratic relationship between $D_e$ and average vortex velocity is observed for a constant geometry and agrees with theory.

In general, the drag due to Dean flow, or Dean drag ($F_D$) scales as $$F_D \sim \frac{\rho U_m^2 a D_h^2}{r}.$$

Figure 7:
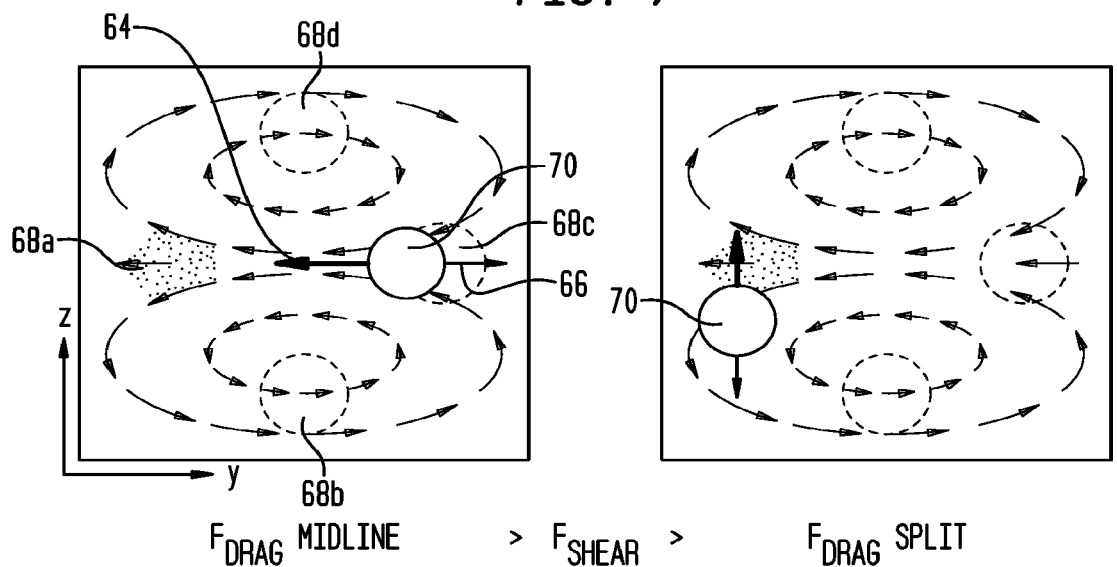
FIG. 7 is a cross-sectional view of one embodiment of an asymmetrically curved channel depicting the superposition of the four stable positions due to inertial lift forces with the Dean flow.

Equilibrium separations can be conducted considering the balance of these two forces, Dean drag 64 and inertial lift 66, as shown in FIG. 7. In particular, FIG. 7 illustrates the cross-section of any asymmetric curved channel depicting the superposition of the four stable positions 68a, 68b, 68c, 68d due to inertial lift forces with the Dean flow. A possible mechanism for biasing a single minimum is also presented. The dominant viscous drag due to the Dean flow acts strongly at the channel mid-line, directing particles to one side of the channel over the other (for the opposite turn this force is of less magnitude in the opposite direction, and does not surpass the inertial force). Once a particle 70 is trapped in this minimum, it can remain because the viscous drag 64 at the split point of the two vortices is less in magnitude than the shear gradient-induced lift 66. Particles at the top and bottom minimum may not remain trapped because the viscous drag acts strongly here as well, and in the direction of a weaker shear gradient.

The ratio of lift to drag forces, $R_f$ scales as $R_f \sim \delta^{-1}(a/D_h)^3$ for a constant $R_c$. Separations are ideal when $R_f \geq 1$ within the channel cross section for a particle of a given size and less than 1 for a particle of another size. For $R_f$, lift forces that push particles to an equilibrium position dominate, while for $R_f$<1, dominant Dean drag overwhelms these equilibrium positions and leads to mixing of particles. The dependence on particle diameter cubed suggests effective separation of particles with small size differences. The $R_f$ relation also suggests that the separation can be tuned to separate particles over a range of diameters by modification of the geometry $D_h$ and curvature ratio (δ).

Theory predicts a limit to the speed of equilibrium separations. Previously, the dependence of the lift/drag ratio, $R_f$, on $R_c$ was neglected. When this dependence is taken into account, velocities higher than optimum are predicted to lead to defocusing. This is because the inertial lift force scales with the channel velocity squared ($U_m^2$) and the lift coefficient ($f_c$), where the lift coefficient decreases with increasing $U_m$. Therefore, the inertial lift force increases at a rate less than $U_m^2$. This can be compared to the drag force due to Dean flow which scales with $U_m^2$. This leads to the ratio of these forces, $R_f$, decreasing with increasing $U_m^2$.

Therefore, three flow regimes can be considered: (1) At low fluid velocities, $R_f$ may be larger than 1 over the majority of the channel cross section; however, the magnitudes of $F_z$ and $F_D$ are too low to create focused streams within the length of channel. (2) At intermediate fluid velocities, $R_f$ may be greater or equal to 1 over a limited region of the channel cross section, and the magnitude of forces is large enough to create focusing to one or more streams. (3) For high fluid velocities, $R_f$ is less than 1 over the entire channel cross section, and Dean drag is dominant, leading to particle mixing.

Using $R_f$ one can predict the particle size cutoff below which focusing does not occur. $R_f$ varies in magnitude across the channel cross section due to variation in $F_D$ and $F_z$ over this region. The functional form of this variation, however, is not currently known and thus it is difficult to predict a priori a particle size cutoff for a given geometry (i.e., for what particle size does $R_f$ initially become <1 throughout the channel cross section). Thus, empirically determined cutoffs can give unknown parameters in $R_f$. The known geometry and cutoff can then be inserted into the equation $R_f=1$ to find the scaling of unknown positional dependent factors. This is because the particle diameter below which the ratio, $R_f$ first becomes less than 1 over the entire channel cross section corresponds to the size cutoff in that channel geometry. In other words, with decreasing particle diameter, $R_f$ decreases to less than 1, resulting in particle mixing due to Dean drag forces dominating.

A semi-empirical relationship is provided quantitatively as follows: First, the condition $R_f(x_{c1})=k(ra_c^3/D_h^4)=1$ is produced, where $x_{c1}$ are the coordinates of the final position to become less than 1 within the channel cross section and k is a scaling factor. The empirical parameters are the channel radius of curvature (r), the cutoff size ($a_c$), and the channel hydraulic diameter. Solving for k for one or more experimental systems allows the development of a relationship that can be applied to an unknown system and size cutoff:

$$r_2 \frac{a_{c2}^3}{D_{h2}^4} = r_1 \frac{a_{c1}^3}{D_{h1}^4}$$

This treatment assumes that both systems are operated at a constant $R_c$ and that particle sizes are small compared to the flow field, since $x_{c1}$ is assumed to remain independent of particle size.

A simplified expression that dictates the geometry of a new channel to separate at a new cutoff can then be developed. If the same radius of curvature is maintained, then an empirical relation for $D_h$ as a function of the cutoff diameter can be written as:

$$D_{h2} = D_{h1}\left(\frac{a_{c2}}{a_{c1}}\right)^{3/4}$$

If height is the dominant factor in determining the inertial lift force and channels with large widths are considered, such that h is the dominant dimension for Dean flow, the equation for $D_{h1}$ above can be rewritten as $h_2=h_1(a_{c2}/a_{c1})^{3/4}$. In general, particles close to the center and outer wall will move toward the channel outer edge, and recirculate along the top and bottom of the channel until they reach an equilibrium position. In other words, the lift forces contribute to focusing the particles in two positions, above and below the plane of symmetry of the channel, along the height while the dean forces affect the lateral position. In accordance with $R_f$, the lateral equilibrium position can be manipulated simply by changing particle diameter (a), geometry ($D_h$), and curvature ratio ($\delta$).

In accordance with the above-described theory, which is generally applicable to all channel geometries, various combinations of parameters will result in localization of a flux of particles in a channel with a given geometry. In general, in certain embodiments, the Reynolds number of the flowing sample can be between about 1 and about 250, the Dean number of the flowing sample can be less than about 20, and/or the ratio of particle diameter to hydraulic diameter can be less than about 0.5. Properties more particularly related to certain channel geometries in view of the above described theory will be discussed below.

Figure 2A:
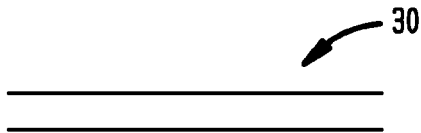
FIG. 2A is a side-view of one embodiment of a straight channel for the separation, ordering, and focusing of particles.
Figure 2B:
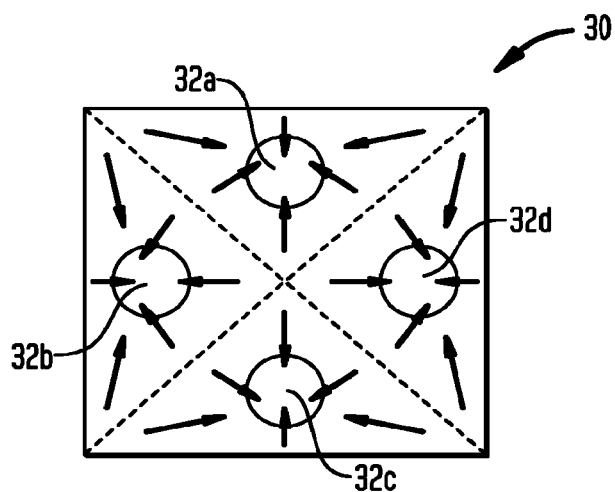
FIG. 2B is a cross-sectional view of the straight channel of FIG. 2A showing four equilibrium positions for focused streams of particles.
Figure 2C:
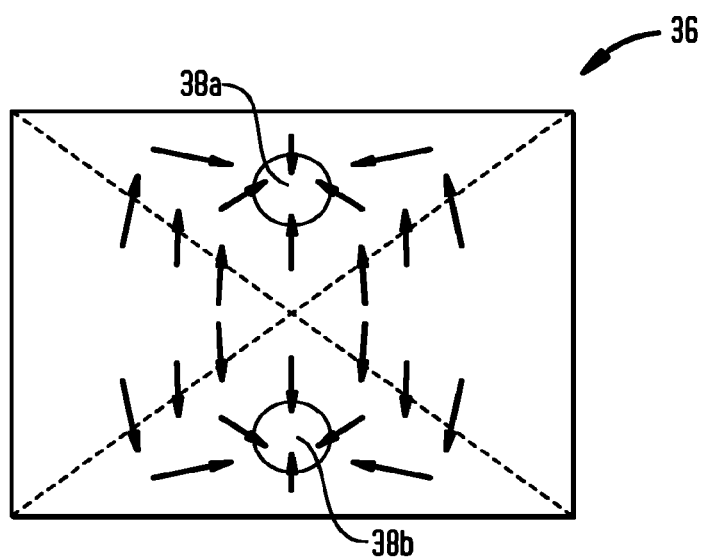
FIG. 2C is a cross-sectional view of an exemplary high-aspect ratio straight channel showing two equilibrium positions for focused streams of particles.
Figure 8A:
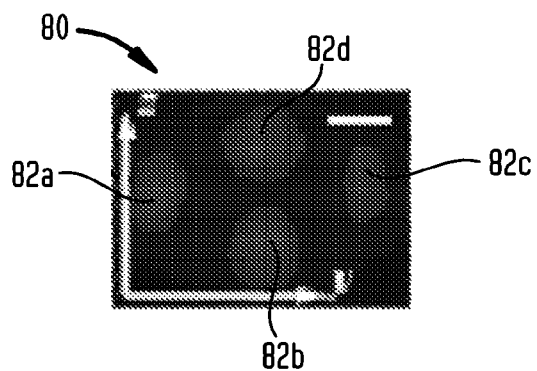
FIG. 8A is a cross-sectional view of one embodiment of a straight channel showing particles focused into four lateral positions.
Figure 8B:
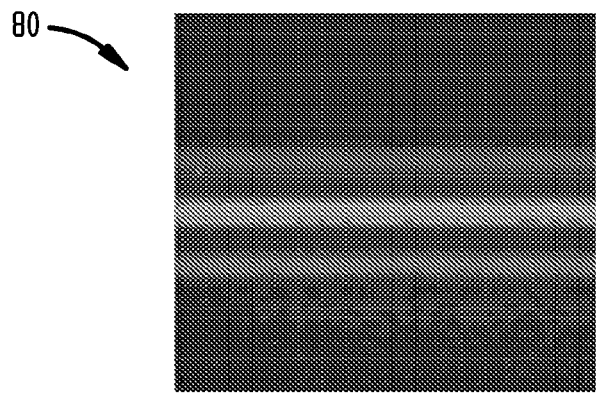
FIG. 8B is a side view of the straight channel of FIG. 8A showing the particles focused into four streams.
Figure 8C:
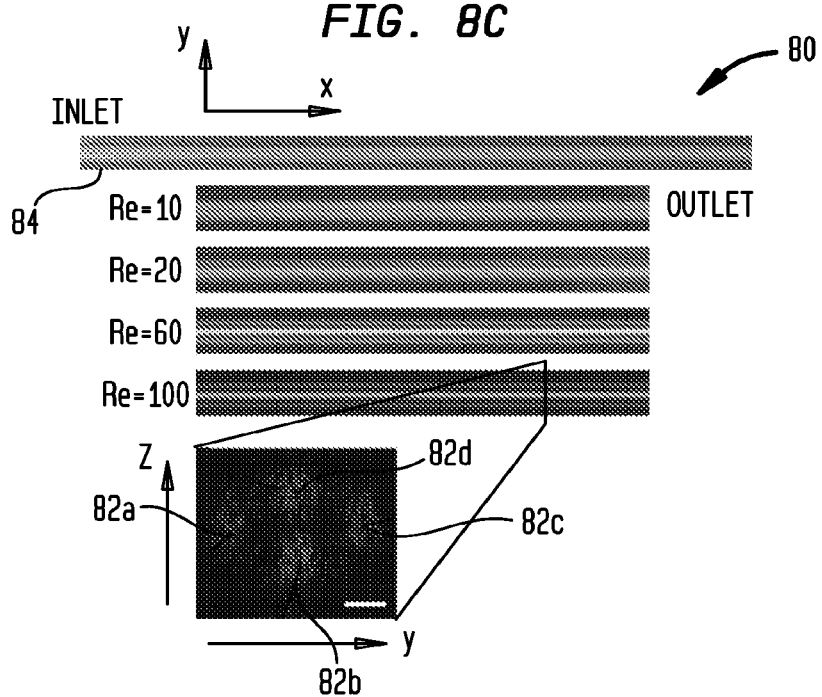
FIG. 8C is a side view and cross-sectional view of the straight channel of FIG. 8A showing that the degree of focusing increases with $R_e$.

As previously noted, FIGS. 2A and 2B illustrate one embodiment of a straight channel having a rectangular cross-section showing force vectors acting on particles therein. Referring now to FIGS. 8A-8C, the separation, ordering, and focusing of particles within these exemplary straight channels will be discussed in more detail. In general, at low flow rates, particles flowing within these exemplary channels distribute uniformly across the cross-section of the channel. As $R_p$ is increased with increasing fluid velocity, patterns of particle segregation in laminar flow become observable that depend significantly on channel scale and symmetry. In general, uniformly distributed particles in rectangular channels migrate across streamlines to four symmetric equilibrium positions 82a, 82b, 82c, 82d at the centers of the faces of the channel and toward the channel edge of a rectangular channel 80 having an aspect ratio of 1:1, as shown in FIGS. 8A-8C. In the illustrated embodiment, particles 9 µm in diameter suspended in water were observed in 50 µm-wide square channels, providing a particle diameter to channel diameter of 0.18. An inlet region 84 is shown where the particles are initially uniformly distributed within the fluid but start to focus shortly thereafter to the four channel faces, as shown in FIG. 8B. FIG. 8C illustrates that the degree of focusing increases with $R_p$ at a given distance along the channel and also increases with the distance traveled along the channel. For $R_p=2.9$ ($R_c=90$), complete focusing is observed after a distance of ~1 cm.

In general, for a given particle size, focusing occurs at a specific distance to the channel wall. The equilibrium position for particles is ~9 µm from the channel edge for $R_c=90$ and agrees with theoretical predictions of ~8 µm in an infinite plane system ($R_c=100$). This distance is also predicted to move closer to the wall for a given particle size as $R_c$ increases. Focusing occurs at channel faces as opposed to corners despite the symmetric features of corners. Presumably, the dominant wall effect acts from two directions on a particle within a corner, and creates an unstable equilibrium point, as shown in FIGS. 8A and 8B. Inertial lift forces alone allow two-dimensional focusing to four precise positions within the lateral face of a rectangular channel.

Figure 9A:
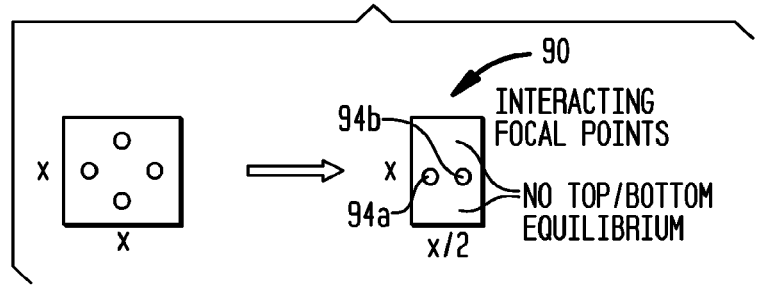
FIG. 9A is a representation of focusing within one embodiment of a high-aspect ratio straight channel, showing focusing to two streams.

Referring now to FIGS. 9A-9D, an alternative rectangular geometry for straight channels is provided. In one embodiment, the rectangular cross-section of a straight channel 90 can be adjusted to produced specific and/or optimized focusing results. In particular, the aspect ratio of the channel 90 cross-section can be changed from about 1 to 1 to about 2 to 1 as shown in FIG. 9A. In addition, particle diameter to channel diameter ratios greater than 0.3 can be employed. When the aspect ratio and the particle diameter to channel diameter are adjusted in this way, particle focusing and ordering can become much more robust (i.e. less deviation in position). In addition, ordering positions reduce from four in the 1 to 1 rectangular channels described above to two in the optimized channels, as shown in FIG. 9A, and particles in the two ordering sites 94a, 94b are observed to interact and order across the channel 90. Ordering occurs for low to high particle concentrations, where only the particle-particle distance is affected by concentration. Importantly, particles become evenly spaced in the direction of flow even to high particle concentration (~50×10$^6$/ml).

Figure 9B:
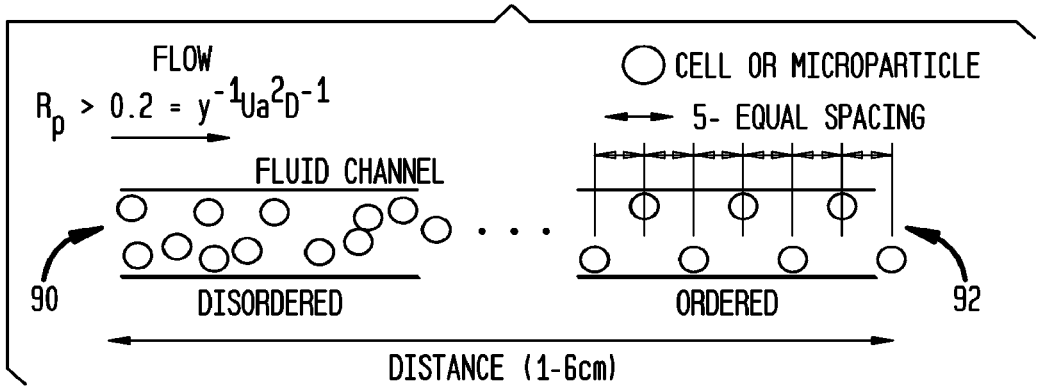
FIG. 9B is a representation of particle ordering and spacing within the straight channel of FIG. 9A.
Figure 9C:
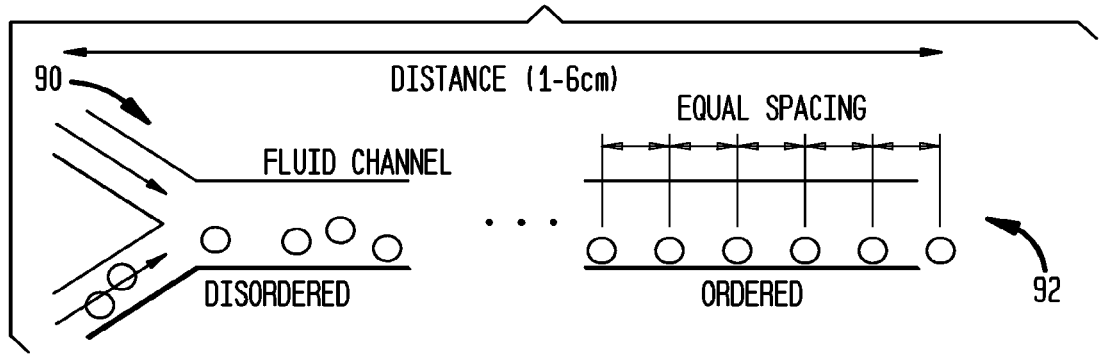
FIG. 9C is a representation of particle ordering and spacing within the straight channel of FIG. 9A.

The new ordering provides a tighter distribution in particle lateral position in the flow as well as improved particle-particle interactions leading to long regular chains 92 of particles with uniform spacing in the direction of flow, as shown in FIGS. 9B and 9C. Precision ordering of cells and particles of 5-15 μm in size can be demonstrated for a variety of particle/cell densities (<5%) at continuous flow, most clearly illustrated in FIG. 9B. As noted above, the geometry change reduces the four ordering positions observed within square or 1 to 1 ratio channels almost entirely to the two ordering positions 94*a*, 94*b*. Further, particles ordered in positions across the channel 90 also interact to create a uniform fluid buffer between them.

In one exemplary system having a 2:1 rectangular geometry, particles all travel with a speed of 13.2-13.8 cm/s (mean fluid velocity being 11.9 cm/s) and exhibit a center-center spacing of 42-45 μm between adjacent particles when they are focused to the same side of the channel 90, but are separated by only 23-25 μm in the direction of flow when the alternating pattern is present. These two patterns can also be found in combination, the particular ratio of one to the other depending most on the local concentration of particles; if the concentration is low, the particle-particle spacing present within the linear array is allowed, as shown in FIG. 9C. As the local concentration increases, however, particles are found more frequently in the interstitial sites on the other side of the channel 90, as illustrated in FIG. 9B. Equilibrium particle spacing at the end of a 6 cm channel is generally linearly dependent on the particle diameter and channel diameter.

Figure 9D:
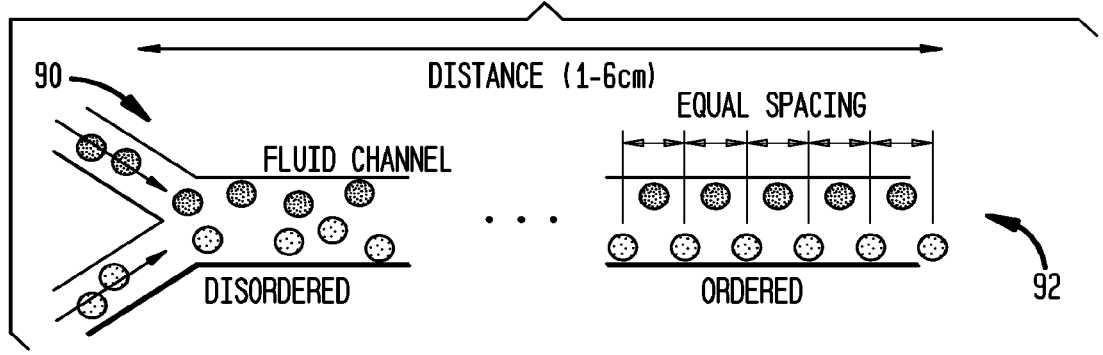
FIG. 9D is a representation of particle ordering and spacing of two different particle types within the straight channel of FIG. 9A.

In another embodiment shown in FIG. 9D, the conditions described with respect to FIGS. 9A-C are applied to particles of two different predetermined types. The particles 92 of a first type (illustrated as open circles) can be introduced into the channel through a first input branch (the lower branch in the figure as illustrated), while a second particle type (illustrated as closed circles) can be introduced into the channel through a second separate channel branch, the upper input branch as shown in the figure. As shown, the two types of particles move from separate input branches into a single channel and are ordered and focused into two streams corresponding to two equilibrium positions on opposite sides of the channel. Where the first and second particles are differing cell types, particles having differing chemistries, or some combination thereof, having the particles focused and ordered such that the particles generally alternate between particles of the first type and particles of the second type as they travel down the channel allows for greater opportunities to observe and manipulate interactions between particles of the first and second types.

While the illustrated geometry for achieving the effects described with respect to FIG. 9 has an aspect ratio of 2 to 1, there is a range of substantially non-1-to-1 aspect ratios for which these effects may be observed. First, as noted above, the effects may be seen regardless of whether it is the width or the height that is twice the other dimension. Of course, the reduction in symmetry for rectangular channels for focusing into two stream lines rather than four will occur so that two longer sides will have focused stream lines of particles that are centered along and spaced apart from the walls. In addition to ratios of about 1 to 2, this reduction in symmetry can be observed in rectangular channels having dimensional ratios of approximately 15 to 50, 3 to 5, and 4 to 5. Accordingly, the effects can be seen for a dimensional aspect ratio of approximately 0.3 (15/50) to a dimensional aspect ratio of approximately 0.8 (4/5), and that the effects can be seen regardless of whether the longer dimension is the width or the height.

Figure 10A:
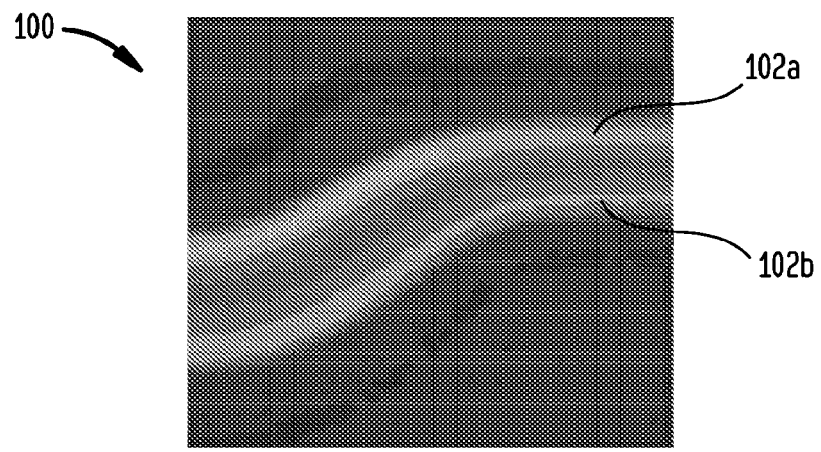
FIG. 10A is a side view of one embodiment of a symmetrically shaped channel showing focusing of particles into two streams.
Figure 10B:
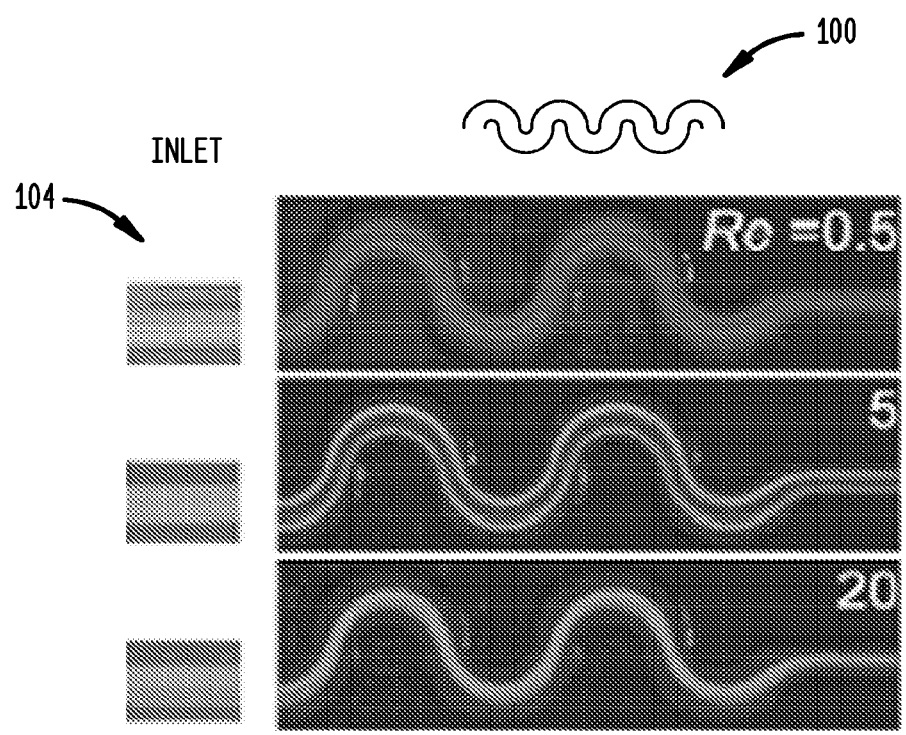
FIG. 10B is a side view of the channel of FIG. 10A illustrating particle focusing increasing with $R_e$.

Curving channels having a sigmoidal shape are also provided, and as previously noted, FIGS. 3A and 3B illustrate one embodiment of such a curving channel. Referring now to FIGS. 10A-10C, the separation, ordering, and focusing of particles within these exemplary sigmoidal channels will be discussed in more detail. Within curving channel systems, symmetry can be reduced by additional inertial forces arising from the particles and fluid. These forces can act in superposition with the lift forces to change equilibrium positions of particles flowing within the fluid. The additional inertial forces generally act in the plus and minus y directions in microfluidic channels with a curving symmetric or sigmoidal geometry, as previously illustrated in FIG. 3B. This geometry can bias the two stable positions on the sides of a channel 100 and can reduce the number of particles collected at the top and bottom focusing points. When the force is sufficient to bias the direction, only two lines of focused particles 102*a*, 102*b* occur, as shown in FIGS. 10A and 10B. As shown in FIG. 10B, particles are randomly distributed in the channel 100 at an inlet 104. As $R_c$ increases between 0.5 and 5, focusing into two streams 102*a*, 102*b* can occur. As $R_c$ increases, mixed streams are again observed, in agreement with an increased contribution from Dean drag.

Figure 11A:
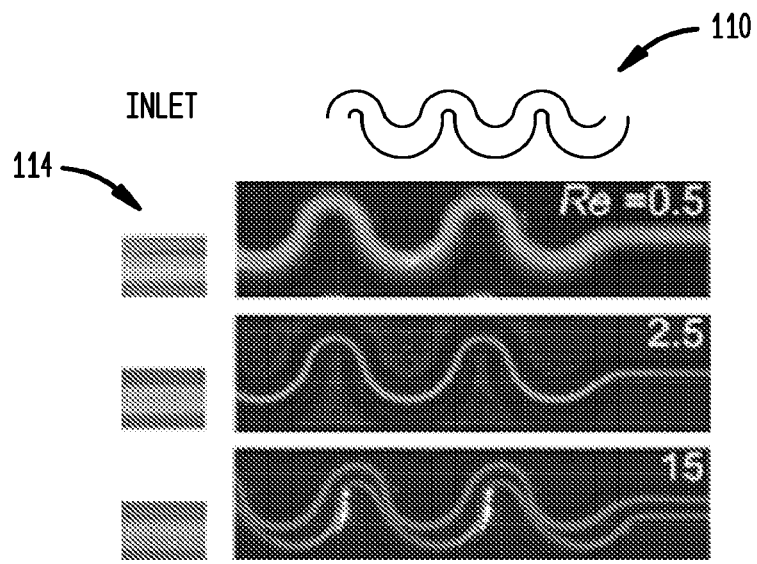
FIG. 11A is a side view of one embodiment of an asymmetrically shaped channel illustrating particle focusing increasing with $R_e$.
Figure 11B:
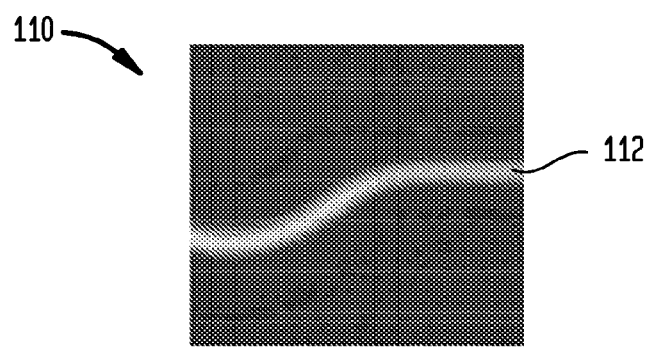
FIG. 11B is a side view of the channel of FIG. 11A, showing a single stream of focused particles.
Figure 11C:
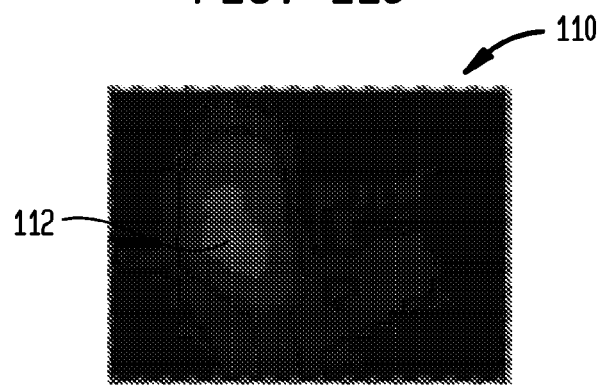
FIG. 11C is a cross-sectional view of the channel of FIG. 11A, showing particles focused to a single equilibrium position within the channel.

An asymmetric curving geometry, such as that previously illustrated in FIG. 4A, can lead to a further reduction in symmetry of particle focusing. Referring now to FIGS. 11A-11D, an exemplary channel 110 having an asymmetric configuration will be discussed. In an asymmetrically shaped channel, the net force generally acts in one direction, biasing a single stable position of the initial distribution, and creating a single focused stream of particles 112, as shown in FIGS. 11A-11D. FIGS. 11A and 11B illustrate that a time-averaged unidirectional centrifugal and/or drag force favors focusing down to a single stream between $R_e$=1–15. As shown, focusing becomes more complex as $D_e$ increases. FIG. 11C further illustrates that particles are focused to one position of minimum potential with the addition of centrifugal forces or drag forces in the −x direction. Complete focusing can also occur for much smaller $R_p$~0.15 and for shorter traveled distances (~3 mm), as shown in FIG. 11D, than in the case of straight rectangular channels. This may partly be due to the mixing action of the Dean flow allowing particles to sample the stable regions of the flow more quickly. FIG. 11D also illustrates the state of the particles in a random distribution near an inlet 114 of the asymmetrically curved channel 110, a second distribution near turn 7 of the channel, and finally the tightly focused stream of particles 112 near the outlet of the channel.

Figure 12:
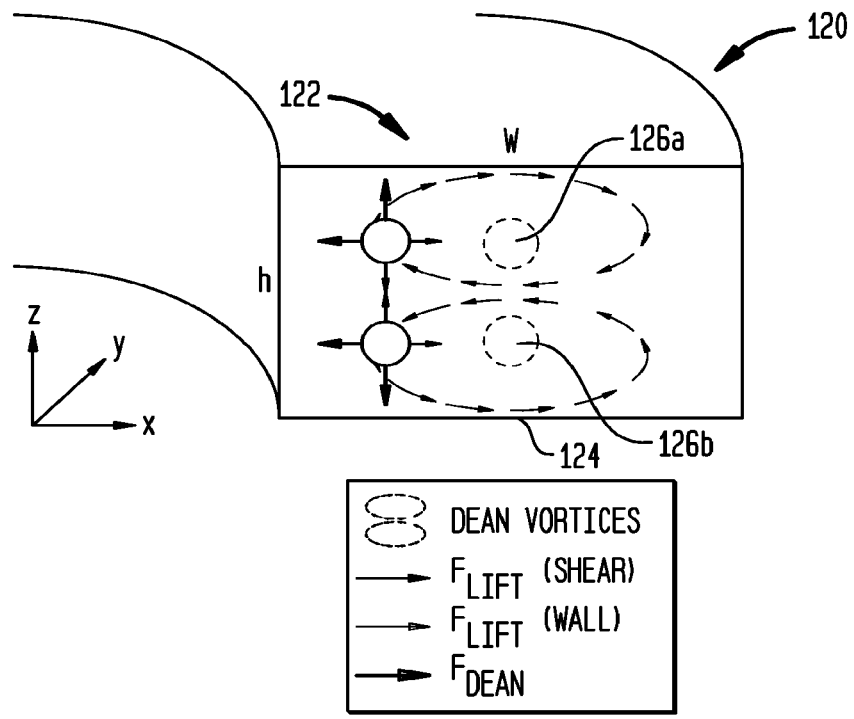
FIG. 12 is a cross-sectional view of one embodiment of an asymmetrically shaped, expanding spiral channel showing equilibrium positions therein for particle focusing.
Figure 13:
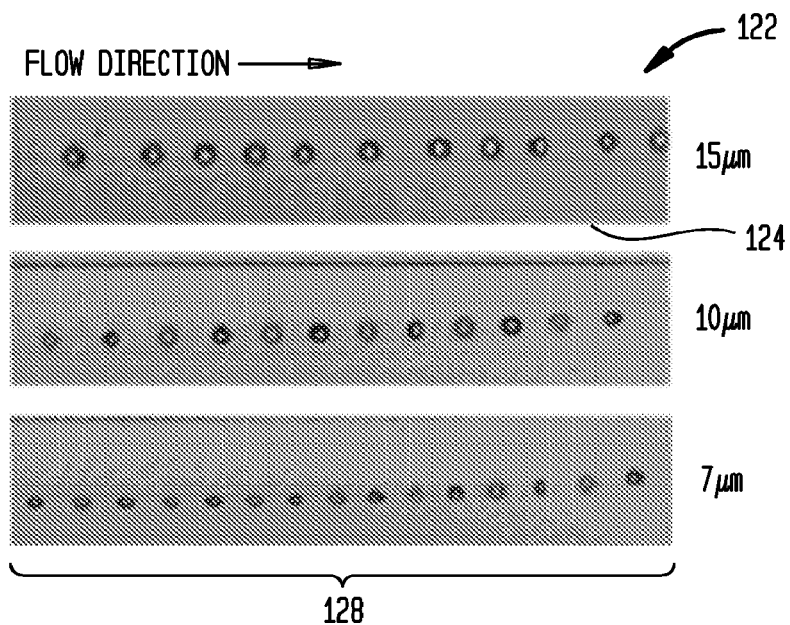
FIG. 13 is a side view of the channel of FIG. 12, illustrating particle ordering therein.

Another exemplary asymmetric geometry can include an expanding spiral shaped geometry as previously shown in FIG. 4C. Referring now to FIGS. 12 and 13, aspects of an exemplary spiral shaped channel 120 will now be discussed. As described above, in a system with inertial lift alone, shear-induced lift forces pushing the particles towards the walls can be balanced by the wall-induced inertia pushing particles away from the wall into an equilibrium position close to the walls. In one embodiment, two significant geometrical features result in equilibrium particle focusing for high-aspect ratio geometry and curvature. For high-aspect ratio geometry, the probability of finding a particle balanced by the inertial forces close to a roof 122 and bottom 124 along the channel 120 width is always greater than close to the inner of outer walls. Thus particles suspended within a sample will tend to focus towards two focusing positions 126*a*, 126*b*, as shown in FIG. 12. The curvature introduces Dean drag that will push the particles in different transversal directions depending on position. As illustrated previously in FIG. 6A, the velocity field shown in arrows illustrates the magnitude and direction of the effect to a particle. For example, a particle located in the center will be pushed towards the outer wall and recirculated through the outer edge roof or bottom until the particles reach the equilibrium position near the inner wall where the Dean forces are superimposed to the inertial forces from the inner walls, as shown in FIG. 12. Hence, in one embodiment, the main forces impacting the particle focusing in the channel height direction may be inertial lift forces, while the Dean forces have a strong influence on the lateral positioning of particles. A particle can remain focused as long as the Dean force trying to push the particle away from the inner wall is balanced by the inertia lift force from the inner wall trying to push the particle towards the inner wall. This results in particles focusing in single-stream lateral positions in two parallel symmetric streams along the height of the channel. In addition to focusing, particles are ordered in uniform spacing in the direction of the flow as shown in FIG. 13. High-speed camera experiments reveal that the ordered particles flow in the same stream line 128, either in the bottom 124 or roof 122, or in alternating particle trains. The behavior seems to be random, and the spacing between the ordered alternating particle trains is always shorter compared to the spacing in the same streamline for the particle concentrations used.

Figure 14:
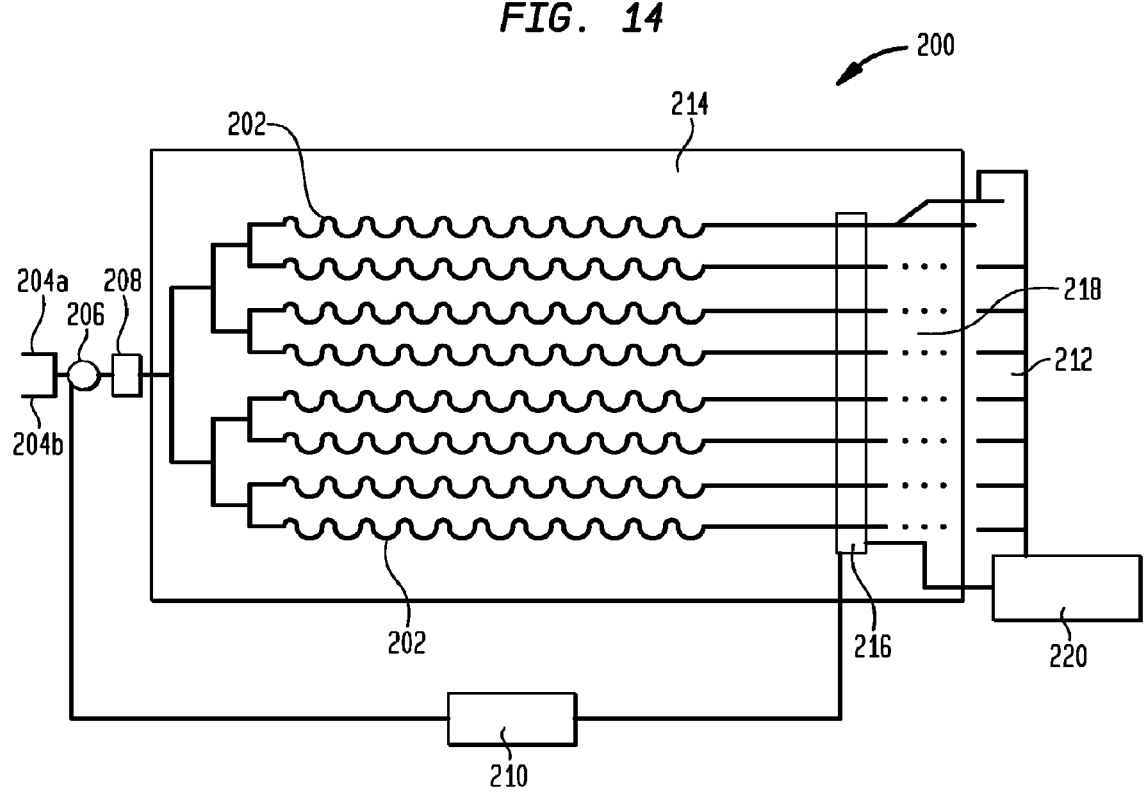
FIG. 14 is a representation of one embodiment of a system for the separation, ordering, and focusing of particles having asymmetrical channels.

Referring now to FIG. 14, any of the exemplary channels described above can be included in various system configurations as needed for any number of applications. In general, however, FIG. 14 illustrates one embodiment of such a system 200 having a plurality of channels 202 for the ordering and focusing of particles as described above. As shown, the system 200 can generally include an inlet 206 having one or more inlet channels 204a, 204b that can be configured for introducing a sample having particles suspended therein into the system 200 through a filter mechanism 208. A pumping mechanism 210 can also be included and can be associated with the inlet 206 and/or with an outlet 212 for introducing a sample into the system 200 under positive or negative pressure.

A microfabricated chip 214 can be provided and can have any number and configurations of any of the channels described above formed therein. FIG. 14 illustrates a plurality of the channels 202 formed in the microfabricated chip 214 that can be configured for receiving a sample introduced through the inlet 206 and filter 208. An analysis region 216 can be provided in proximity to an output channels 218 of the channels 202 to monitor, sort, count, image, or otherwise analyze the focused streams of particles. The output channels 218 can be provided to receive and/or collect one or more focused streams of particles per channel after the streams travel through the analytical region of the chip. One or more output channels 218 can also be provided for separating particles of a predetermined type away from a main stream of particles via a microfluidic valve. A controller 220, which can include any number of hardware, software, and analytical elements can be included to assist in pre-sample processing, pumping, flow rate regulation, valve operation, and any analysis to be performed on focused particles. After focusing, particles can be collected from the output channels into a reservoir or outlet 212 for initial or additional analysis elsewhere, or for disposal.

Referring in more detail now to the system 200 described above, one or more inlets can be provided for introducing samples and/or other substances into the channels within the system. An inlet can generally contain an inlet channel, a well or reservoir, an opening, and any other features which facilitates the entry of particles into the system. The opening in the inlet can be in a floor of the microfabricated chip, to permit entry of the sample into the device. The inlet can also contain a connector adapted to receive a suitable piece of tubing, such as liquid chromatography or HPLC tubing, through which a sample can be supplied from an external reservoir. The inlet is generally in fluid communication with the channels and is generally upstream therefrom. As noted above, a sample can be diluted or concentrated before entering the channels and a separate inlet can be provided for introducing such a diluent or concentrate to mix with the sample to achieve a desired particle to volume ratio. Additional inlets can be provided for other substances having labels or tags as will be described below, to facilitate mixing with the sample before introduction into the channels. Any number and combination of inlets can be provided. In the same way, any number of outlets can be provided for receiving and collecting the sample and focused streams of particles within the sample, as will be described in more detail below.

Various methods can be used for identifying ordered and focused particles of a predetermined type within the channels. Labels or tags for identifying or manipulating particles to be focused within the channels can be introduced into the sample before, during, and/or after introduction of the sample into the system. Labeling or tagging of particles is well known in the art for use, for example, in fluorescence-activated cell sorting (FACS) and magnetic-activated cell sorting (MACS), and any of the various methods of labeling can be used in the systems described herein. In general, any techniques or methods related to the identification and/or manipulation of particles based on their size, weight, density, electrical properties, magnetic properties, dielectric properties, deformable properties, fluorescent properties, surface characteristics, intraparticle characteristics such as interparticle spacing, and/or rotational characteristics such as rotational rate, rotational frequency, and variation in rotational rate over a cycle, can be used, to name a few. In other embodiments, characteristics of a particle can be changed so that the particle can be manipulated and/or identified based on its changed characteristic. For example, the size of a particle can be changed by adding a bead, particle, or other tag to it such that the particle will be shifted and focused into a particular stream, and perhaps a particular channel branch or outlet, based on its changed size. Exemplary labels can include, but are in no way limited to quantum dots, pentamers, antibodies, nano-beads, magnetic beads, molecules, antimers, affinity label beads, micro-beads, cell/cell signaling, etc. There is no limit to the kind or number of particle characteristics that can be identified or measured using known labeling techniques, provided only that the characteristic or characteristics of interest be sufficiently identifiable. Exemplary labeling methods and techniques are discussed in detail in U.S. Pat. No. 6,540,896 entitled, "Microfabricated Cell Sorter for Chemical and Biological Materials" filed May 21, 1999; U.S. Pat. No. 5,968,820 entitled, "Method for Magnetically Separating Cells into Fractionated Flow Streams" filed Feb. 26, 1997; and U.S. Pat. No. 6,767,706 entitled, "Integrated Active Flux Microfluidic Devices and Methods" filed Jun. 5, 2001; all of which are incorporated by reference in their entireties.

As noted above, particles can be labeled or tagged prior to introduction of the sample into the system. Alternatively or in addition, a secondary inlet can be included in the system to facilitate introduction of labels in parallel with introduction of the sample such that the labels and sample mix while entering the channels. In other embodiments, inlet ports can be included at various locations within the system along channel lengths such that mixing of labels and particles can occur within the channels before, during, and/or after focusing of the particles.

Various techniques exist for moving the sample through the channels described herein and in general, the system can include a pumping mechanism for introducing and moving the sample into and through the channels. The pumping mechanism can also regulate and control a flow rate within the channels as needed. A specific pumping mechanism can be provided in a positive pumping configuration, in a negative pumping configuration, or in some combination of both. In one embodiment, a sample can be introduced into the inlet and can be pulled into the system under negative pressure or vacuum using the negative pumping configuration. A negative pumping configuration can allow for processing of a complete volume of sample, without leaving any sample within the channels. Exemplary negative pumping mechanisms can include, but are not limited to, syringe pumps, peristaltic pumps, aspirators, and/or vacuum pumps. In other embodiments, a positive pumping configuration can also be employed. A sample can be introduced into the inlet and can be injected or pushed into the system under positive pressure. Exemplary positive pumping mechanisms can include, but are not limited to, syringe pumps, peristaltic pumps, pneumatic pumps, displacement pumps, and/or a column of fluid. Oscillations caused by some pumping mechanisms, such as a peristaltic pump, can optionally be damped to allow for proper focusing within the channels. Alternatively, the oscillations can be used to encourage mixing of particles and labels within the channels. As will be appreciated by those skilled in the art, any other pumps configured for pumping fluid can be used depending on the requirements of the system. A single pump can be used for all pumping requirements, including introduction of the sample, adjustment substances, and labels. Alternatively, independent pumping systems can be used to control introduction of independent samples, substances, and labels into the system. Generally, pumps can be interfaced with the system using hermetic seals, such as silicone gaskets, although any mechanism of interfacing the pumps with the system can be used as needed depending on specific configurations.

In another aspect of the system, flow rates within the channels can be regulated and controlled. This can include control of flow rate, impeding of flow, switching of flows between various input channels and output channels, and volumetric dosing. In an embodiment having a plurality of channels, the flow rate of samples can be controlled in unison or separately. In an embodiment in which the flow rate is controlled in unison, pressure supplied by the pumping mechanism can be adjusted as needed depending on the number of parallelizations of channels. Alternatively, variable and differential control of the flow rates in each channel can be achieved using various techniques known in the art including, for example, a multi-channel individually controllable syringe manifold. More particularly, the input channel distribution can be modified to decouple all parallel networks of channels. An output can collect the output from all channels via a single manifold connected to a suction. Alternatively or in addition, the output from each network can be collected separately for downstream processing. Flow rate can be controlled by the pumping mechanism, a valve system, and/or by a controller.

Any number and variety of microfluidic valves can also be included in the system to block or unblock the pressurized flow of particles through the channels. Valves can be positioned in or near any number of inlets and outlets, as well as in or near channels, channel branches, pumping mechanisms, and controllers. In one embodiment, a thin cantilever can be included within a branch point of the channels such that it may be displaced towards one or the other wall of a main channel, typically by electrostatic attraction, thus closing off or changing a pressure resistance within a selected branch channel. Alternatively or in addition, valves can be microfabricated in the form of electrostatically operated diaphragms, as are well known in the art. Mobile diaphragms and flexible membranes within a multi-layer structure can be used such that under pressure, flexing occurs to block or change resistance in or near inlets, outlets, channels, and/or channel branches, and can redirect flows into specific channel branches and/or outlets. Typical processes for including such microfabricated valves can include the use of, for example, selectively etched sacrificial layers in a multi-layer structure. In another embodiment, the microvalve can include one or more mobile diaphragms or flexible membranes formed in a layer above a channel branch, inlet, or outlet such that upon actuation, the membrane is expanded up to decrease resistance within a channel branch, inlet, or outlet, or expanded down into the channel to increase resistance within the same. In this way, flow of particles within the channels can be directed and controlled depending on predetermined parameters. Further details and discussion of such microfluidic diaphragms are disclosed in PCT Publication No. PCT/US2006/039441 entitled, "Devices and Methods for Cell Manipulation" filed Oct. 5, 2007 and incorporated herein by reference in its entirety. A person skilled in the art will appreciate that any microvalves and/or microfabricated valves known in the art can be used within and throughout the system as required.

In another aspect of the system, one or more microfluidic, size-based separation modules or filters can optionally be included to prevent clogging within the channels by preventing certain particle sizes or particle types from entering the channels and/or to facilitate collection of particles for downstream processing. Typically, particles larger than the largest channel dimension can be removed prior to injection into the channel to prevent clogging within the system. In one embodiment, a filtering process can be performed apart from the system to remove particles, including dust and debris, which are too large and/or too small from the sample that will ultimately be introduced into the channels. In another embodiment, one or more filters can be included somewhere within the system. For example, one or more filters can be positioned just after the inlet such that the sample is required to pass through the filters to enter the channels. One filter can be included to remove particles larger than a required size and another filter can be included to remove particles smaller than a required size. Filters can also optionally be included within a positive pumping mechanism so that the sample is filtered before entering the inlet. Alternatively or in addition, filters can be disposed within valve systems, within the channels, and/or near the output of the channels as needed in specific configurations of the system. In other embodiments, channel sizes can be sequentially reduced over a portion of the system to facilitate separation of larger particles from the substance.

Various types of microfluidic filters known in the art can be used to remove specific particle sizes or types from the sample. Structural filters can be used for filtration, including mesh filters, microfabricated frits, pillar structures, microposts, affinity columns, or flow restrictions within channels. In one embodiment, one or more mesh-style filters can be used to separate specific particles from the sample. A mesh-style filter can mechanically prevent particles of a certain size from traveling through specifically sized holes or gaps within the mesh. Additionally, the mesh can selectively allow passage of particles based on their size, shape, or deformability. Two or more mesh-style filters can be arranged in series or in parallel, for example, to remove particles of increasing or decreasing size successively. In another embodiment, microposts, such as those described in U.S. Publication No. 2007/0264675 entitled, "Microfluidic Device for Cell Separation and Uses Thereof" filed May 8, 2007 and incorporated herein by reference in its entirety, can be included in the output region of the chip. Microposts can be included in various positions on the chip as needed for filtration. In one embodiment, if tagged particles being analyzed and directed into a specified channel or reservoir are missed by another filter or analysis device, one or more microposts positioned downstream can act as a filter to direct these particles into an additional channel or collection reservoir to ensure a larger portion are collected. In other embodiments, diffusional filtration can be used in addition to or as an alternative to structurally based filters.

A variety of techniques can be employed to fabricate the chip having channels formed therein for the separation, ordering, and focusing of particles. The technique used can be selected based, in part, on the material chosen for forming the chip. Exemplary materials for fabricating a microfluidic chip can include glass, silicon, steel, nickel, poly(methylmethacrylate) (PMMA), polycarbonate, polystyrene, polyethylene, polyolefins, silicones (for example, poly(dimethylsiloxane)), and any and all combinations thereof. Methods for forming channels within these materials are also well known in the art, and can include soft lithography, photolithography (for example, stereolithography or x-ray photolithography), molding, embossing, silicon micromachining, wet or dry chemical etching, milling, diamond cutting, Lithographie Galvanoformung and Abformung (LIGA), and electroplating. For example, for glass, traditional silicon fabrication techniques of photolithography followed by wet (KOH) or dry etching (reactive ion etching with fluorine or other reactive gas) can be employed. Techniques such as laser micromachining can be adopted for plastic materials with high photon absorption efficiency. This technique is suitable for lower throughput fabrication because of the serial nature of the process.

For mass-produced plastic devices, thermoplastic injection molding, and compression molding can be used. Conventional thermoplastic injection molding used for mass-fabrication of compact discs can also be used to fabricate the microfluidic chips described herein. For example, channel features as well as other features required on the chip can be replicated on a glass master by conventional photolithography. The glass master is electroformed to yield a tough, thermal shock resistant, thermally conductive, hard mold. This mold can serve as the master template for injection molding or compression molding the features into a plastic device. Depending on the plastic material used to fabricate the chip and the required throughput of the finished system, compression molding can be chosen as a preferred method of fabrication. Compression molding, also known as hot embossing or relief imprinting, has the advantage of being compatible with high molecular weight polymers, which are excellent for small structures. For high aspect ratio structures, injection molding can be a preferred method of fabrication but is most suitable for low molecular weight structures.

A microfluidic chip such as those described herein can be fabricated in one or more pieces that are then assembled. In one embodiment, separate layers of the chip can contain channels for a single fluid. Layers of the chip can be bonded together by clamps, adhesives, heat, anodic bonding, or reactions between surface groups (wafer bonding). Alternatively, a chip having channels in more than one plane can be fabricated as a single piece, for example using stereolithography or other three-dimensional fabrication technique.

In one particular embodiment, the chip can be formed of PMMA. The features, including channels, can be transferred onto an electroformed mold using standard photolithography followed by electroplating. The mold can be used to hot emboss the features into the PMMA at a temperature near its glass transition temperature (105° C.) under pressure (5 to 20 tons). The mold can then be cooled to enable removal of the PMMA chip. A second piece used to seal the chip, composed of a similar or dissimilar material, can be bonded onto the first piece using vacuum-assisted thermal bonding. The vacuum prevents formation of air gaps in the bonding regions. As will be appreciated by those skilled in the art, the chip can be formed of any material or combination of materials as needed for specific pressure requirements within the channels, as well as specific channel geometries and size requirements.

As illustrated in FIG. 14 and as noted above, the system can optionally include a controller. The controller can include, be operatively connected to, and/or control various analytical equipment or analyzers disposed within the chip and/or around the chip to accommodate processing and analysis of focused particles as the particles enter the analysis region, as well as to control various flow rates, pumping systems, and/or valve systems. An analyzer can include any sample analyzing device known in the art, such as, for example, a microscope, a microarray, a cell counter, etc. An analyzer can further include one or more computers, databases, memory systems, and system outputs, for example, a computer screen or printer. In some embodiments, an analyzer can include a computer readable medium, for example, floppy diskettes, CD-ROMS, hard drives, flash memory, tape, or other digital storage medium, with a program code having a set of instructions for detection or analysis to be performed on the focused stream or streams of particles. In some embodiments, computer executable logic or program code of an analyzer can be loaded into and/or executed by a computer, or transmitted over some transmission medium, such as over electrical wiring or cabling, through fiber optics, or via electromagnetic radiation. When implemented on a general purpose microprocessor, the computer executable logic configures the microprocessor to create specific logic circuits. In one embodiment, the computer executable logic performs some or all of the tasks described herein including sample preparation, dilution, concentration, pumping, flow rate regulation, detection, and/or analysis. In some embodiments, the controller can be at a location remote from the chip, channels, pumping mechanism, and other components of the system. For example, the chip, channels, and other system components can be located in one room, building, city, or location and the controller can be located in another room, building, city, or location. The controller can be configured to communicate wirelessly with the components from a remote location to configure, control, program, and/or otherwise manage any and all aspects of the procedures and devices related to the focusing of particles and analysis of focused particles as described herein. The controller can communicate with the other components in a system of the invention using any wireless technology known in the art, including but not limited to, Bluetooth, the IEEE 802.11 standard, Wi-Fi, broadband wireless, and/or any wireless communication that can be accomplished using radio frequency communication, microwave communication, and infrared communication. The controller may utilize point-to-point communication, point-to-multipoint communication, broadcasting, cellular networks, and/or wireless networks. The controller may also utilize wired networks such as local area networks, wide area networks, and/or the Internet.

It is contemplated that the system described herein can be packaged together as a kit or singular unit for diagnostics and point-of-care applications. In other embodiments, some, any, and/or all components can be separate to work in individualized locations to maximize size and/or efficiency, for example in industrial applications. In one embodiment, a kit or singular unit for diagnostics and point-of-care applications can include a microfabricated chip having channels formed thereon, a pumping mechanism, valves, filters, controller, and any other components that may be required for a particular application. The components and channel configurations can vary as needed in a particular unit. In some embodiments, the unit can be in the form of an open system in which various components of the system, for example, the chip, can be replaced as needed by a user. In other systems, the unit can be in the form of a closed system in which no components can be replaced by the user. In any of the embodiments and configurations, any and all components of the system can be single use, disposable, time limited, reconditionable, and/or reusable.

Any and all components of the system can be reconditioned for reuse after at least one use. Reconditioning can include any combination of the steps of disassembly of the a system of the invention or system components, followed by cleaning and/or replacement of particular pieces, and subsequent reassembly. In particular, a system of the invention can be disassembled, and any number of the particular pieces or parts of the device can be selectively replaced or removed in any combination. Upon cleaning and/or replacement of particular parts, the device can be reassembled for subsequent use either at a reconditioning facility, or by a surgical or research team immediately prior to a procedure or test. Those skilled in the art will appreciate that reconditioning of a device can utilize a variety of techniques for disassembly, cleaning/replacement, and reassembly. Use of such techniques, and the resulting reconditioned device, are all within the scope of the present application.

The systems described herein can be used in a wide range of conventional enumerating, sorting, concentrating and ordering techniques. There is an ever increasing need in biological research, for example, for more accurate and efficient methods to manipulate and separate target particle and cell populations. Disciplines ranging from immunology and cancer medicine to stem cell biology are highly dependent on the identification of uncontaminated populations of particular particle and cell subsets for detailed characterization. Clinically, microbiologists routinely isolate bacterial cells and white blood cell subsets for diagnostic purposes. Tumor antigen-specific regulatory T cells can be discovered in the circulating blood of cancer patients, presenting a new potential target for immunotherapy of metastatic melanoma. Environmental sensing requires surveillance of water, food and beverage processing for specific bacterial cell contamination. Vaccine developers work largely with antigen-specific T lymphocytes, rare cells which may differ from one another by no more than a single amino acid in a peptide fragment presented on the cell surface. In these different applications a common problem is presented: the need to isolate, separate and characterize subpopulations of cells present within heterogeneous, complex fluids. During the processing of these samples, the target cell population must be handled with gentle care, preventing alteration of the cell's physiological state to allow for subsequent expression profiling and molecular studies. Moreover, the cells of interest may be present at extremely low frequencies-often less than 1 cell in 10,000,000 cells, for circulating tumor cells or disease-specific T lymphocytes, increasing the complexity of the challenge. As shown in FIG. 15C, the frequency of the target cell population in whole blood, for example, varies greatly depending on the application, illustrating the necessity for a dynamic sorting device that can process both small (10 μl) and large (10 ml) amounts of whole blood with equal specificity and efficiency without altering the integrity of the cells.

Applications for a sensitive, high throughput, point-of-care particle and blood cell manipulator are far reaching. In the area of prenatal diagnosis of genetic abnormalities, for example, fetal nucleated red blood cells are a promising candidate for non-invasive diagnosis. However, the concentration of nucleated red blood cells in maternal blood is very low (1 per $10^6$ cells), current cell sorting techniques are not suitable for analysis. In the field of cancer research, the ability to selectively isolate and characterize extremely rare (1 in $10^9$ cells) circulating tumor cells (CTCs) could transform patient diagnosis, prognosis and treatment. With increased throughput provided by systems of the invention described herein, the potential exists to isolate circulating tumor cells in very early stage cancer patients where the frequency of cells is proposed to be even lower. Fundamental to self/non-self recognition, a T cell contains a unique surface receptor that recognizes a specific peptide sequence, or antigen; although the exact diversity of T cells in the body is unknown, estimates suggest that there are at least $2.5 \times 10^7$ unique T cells in human blood. Isolating these cells becomes a significant challenge when their frequency in blood is quite low, thus requiring a large sample volume to be processed in order to isolate a statistically significant number of these cells. For example, in individuals latently infected with tuberculosis, the frequency of CD8+ T cells specific for a particular T8 antigen may be less than 1 in 200,000 peripheral blood mononuclear cells, which is the limit of sensitivity with existing sorting and ordering systems. The ability to measure even lower frequencies would be beneficial to vaccine development and diagnostics. Nonetheless, given 1 ml of whole blood, fewer than five specific antigen-specific T cells (ATGs) might be present, meaning that it might be necessary to process as much as 5-10 ml of whole blood samples in order to obtain an ATG population of a reasonable size, which conventional systems are incapable of doing in any time-sensitive manner, if at all.

The systems and methods described herein thus provide a manner in which rare cells can be sorted, separated, enumerated, and analyzed continuously and at high rates. Whether a particular cell is a rare cell can be viewed in at least two different ways. In a first manner of characterizing a cell as rare, the rare cell can be said to be any cell that does not naturally occur as a significant fraction of a given sample. For example, for human or mammalian blood, a rare cell may be any cell other than a subject's blood cell (such as a red blood cell and a white blood cell). In this view, cancer or other cells present in the blood would be considered rare cells. In addition, fetal cells (including fetal blood cells) present in a sample of the mother's blood should be considered rare cells. In a second manner of characterizing a cell as rare might take into account the frequency with which that cell appears in a sample or with respect to other cells. For example, a rare cell may be a cell that appears at a frequency of approximately 1 to 50 cells per ml of blood. Alternatively, rare cell frequency within a given population containing non-rare cells can include, but is not limited to, frequencies of less than about 1 cell in 100 cells; 1 cell in 1,000 cells; 1 cell in 10,000 cells; 1 cell in 100,000 cells; 1 cell in 1,000,000 cells; 1 cell in 10,000,000 cells; 1 cell in 100,000,000 cells; or 1 cell in 1,000,000,000 cells.

Figure 15A:
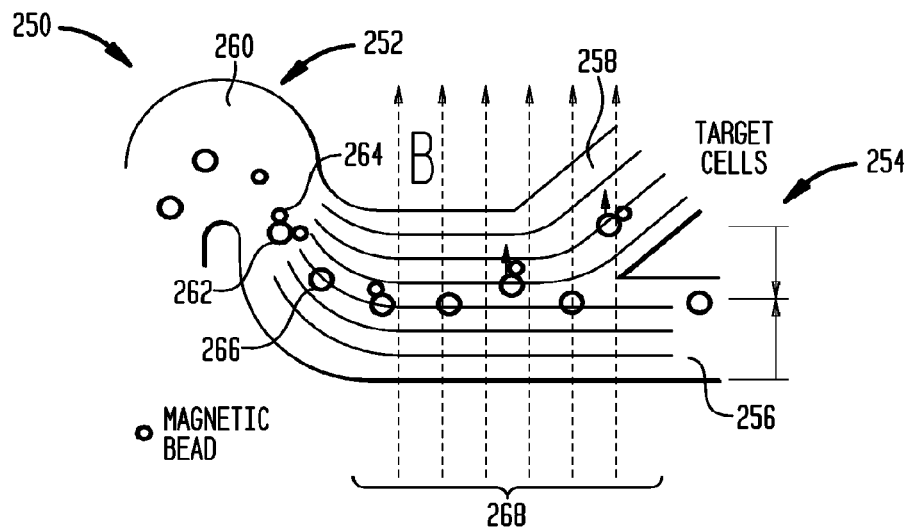
FIG. 15A is a representation of one exemplary system and method for passive particle separation using magnetically labeled particles for identification in focused streams.

Referring now to FIG. 15A, one embodiment of a particle sorting configuration for the systems described herein is provided. In particular, FIG. 15A illustrates a passive sorting mechanism in the form of a magnetic-activated particle sorting configuration 250. A microfabricated chip can generally be provided having one or more asymmetric channels 252 formed therein. An analysis region of the chip can also be provided in which an output region 254 of each main channel 252 can include a fork or channel branch point that transitions the main channel 252 into first and second output channels 258, 256. A sample 260 can be prepared for introduction into the system 250 and target particles 262 of a predetermined size can be directed into the asymmetrically curving channels 252 to be focused into a single, tightly localized stream.

Magnetic labels, tags, markers 264, or a reagent to render particles of interest magnetic, can be introduced into the system 250 and mixed with the sample 260 before its introduction into the channels 252 and/or after the particles 262 have been focused and before the particles 262 enter the analysis region. As will be appreciated by those skilled in the art, any and all conventional MACS methods and techniques can be used with the system 250 of the invention as noted above and as further described in connection with the illustrated embodiment. For example, the particles 262 can be cells incubated with magnetic markers 264 in the form of magnetic beads coated with antibodies against a particular surface antigen of the cell. This causes the cells expressing this antigen to attach to the magnetic beads. In other embodiments, certain cells, such as nucleated red blood cells, could be rendered magnetic by altering the oxidation state of the cytoplasmic Hemoglobin with a reducing agent. In addition, a cell can be sorted based on intrinsic magnetic properties. Cells having internalized ferrous containing particles, for example cells with saturated transferrin receptors, could be separated from other cells based on their higher magnetic moment. In still another example, macrophages with ingested red blood cells can be separated from other macrophages and white blood cells by virtue of the magnetic properties of the Hemoglobin in the ingested red blood cell. Regardless of the type of magnetic marker 264, the magnetic property used to identify a particle, or of where the magnetic markers 264 are introduced, however, the markers 264 will ultimately be attached to the target particles 262 of a predetermined type within the focused stream of particles as they enter the analysis region.

As shown in FIG. 15A, the channels 252 can be configured such that the focused stream of marked particles 262 and unmarked particles 266 leaving the asymmetrically shaped portion of the channels 252 will naturally flow into the second output channel 256. A magnetic biasing element, such as a magnetic field gradient and/or a magnetic field 268, can be applied across the analysis region 254 near the channel branch point such that magnetically marked particles 262 will be deflected a distance away from the focused stream in response to the magnetic field 268 and will enter the first channel output 258 instead of the second channel output 256. The tightly focused stream(s) of particles provided by any channel geometry, for example, straight, symmetric, and/or the asymmetric curvature of the channels 252 allows such a configuration as only a relatively small amount of deflection by the magnetic field 268 is required to direct the marked particles 262 into the first channel output 258. This allows systems of the invention to operate with lower noise, better accuracy, and with higher throughput as the smaller deflections required with focused particle streams allow for higher flow conditions. In one embodiment, separating cells with a weak magnetic moment is allowable because of the bare minimum deflection needed to deflect flow trajectory in a tightly focused stream. So directed, the marked and unmarked particles 262, 266 can be identified, sorted, counted, collected, and otherwise analyzed further as needed. A person skilled in the art will appreciate that any channel geometry can be used in this configuration, and any number of channels and channel branch points can be included to separate particle streams and perform sorting in parallel configurations.

Particle stream precision is essential for magnetic sorting applications of the sort described above, as increased precision of initial particle position leads to reduced false positives after magnetic deflection and increased throughput. The lowest inertial force necessary can be calculated and used to produce single ordered streams of particles with variation in center position <100 nm. Weaker inertial focusing equilibrium positions can facilitate magnetic deflection of labeled particles. This value can be measured by analyzing images from high-speed camera data and channel length can be adjusted as needed to compensate for lower inertial forces. In one embodiment, a design that initially produces strong equilibrium focusing forces and then changes gradually to the smaller magnitude forces by increasing the channel width gradually can reduce the effective channel length.

Figure 15B:
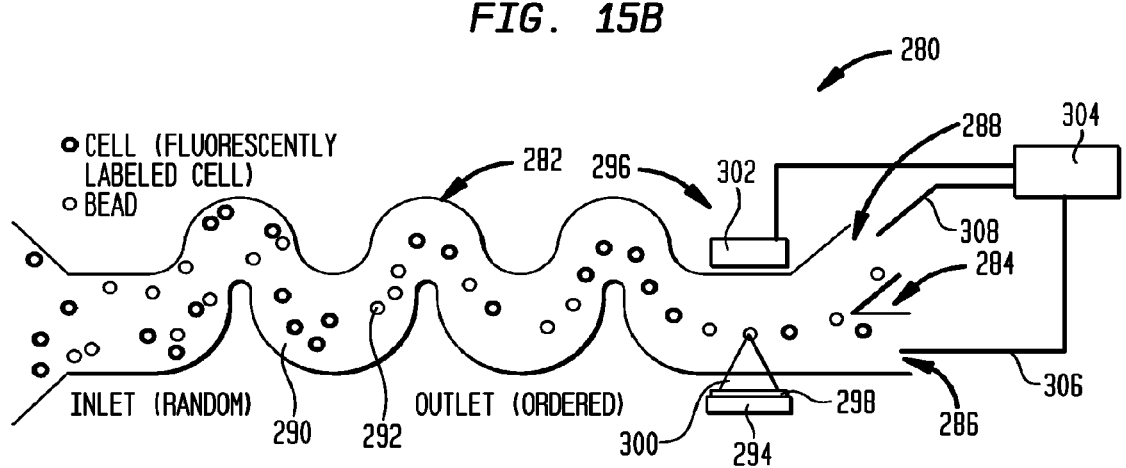
FIG. 15B is a representation of one exemplary system and method for active particle separation using fluorescence to identify particles of a predetermined type in focused streams.
Figure 15C:
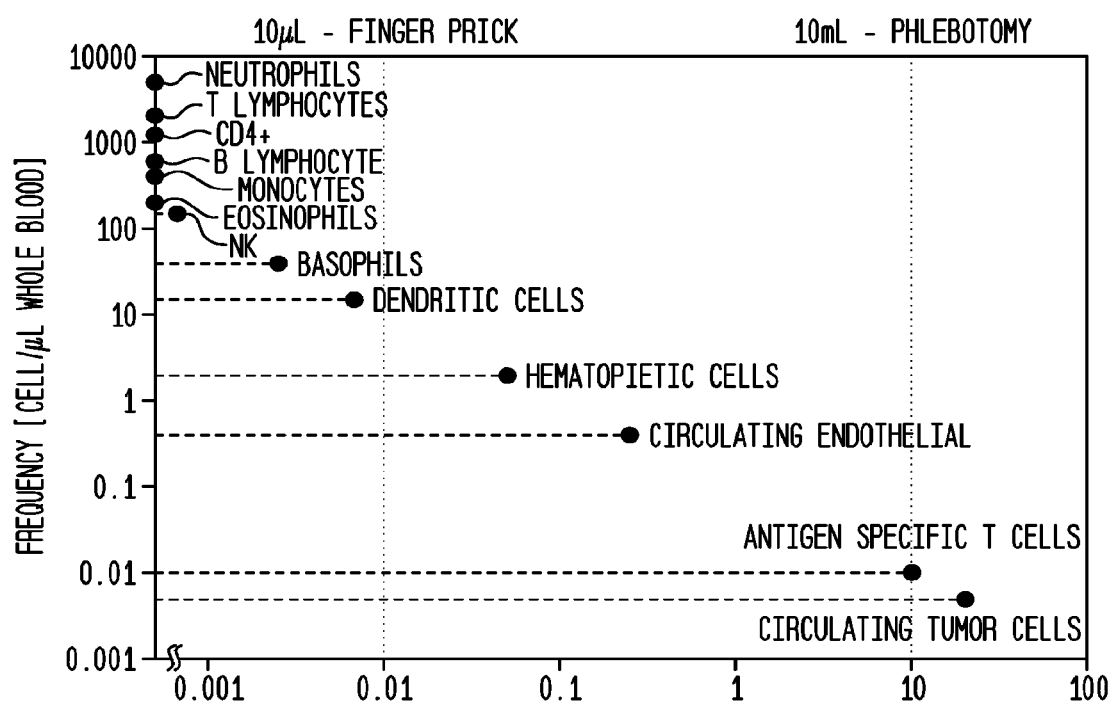
FIG. 15C is a graphical representation of the frequency of rare cell population within whole blood.

FIG. 15B illustrates another embodiment of a particle sorting configuration for the systems described herein. In general, an active sorting mechanism is provided in the form of a fluorescence-activated particle sorting configuration 280. Similar to FIG. 15A, a microfabricated chip can be provided having one or more asymmetric channels 282 formed therein. The chip can include an analysis or detection region 284 in proximity to an output region of each main channel 282. Each channel 282 can include a fork or channel branch point that transitions the main channel 282 into first and second output channels 288, 286.

A sample 290 can be prepared for introduction into the system 280 by tagging particles 292 of a predetermined type with an optically sensitive tag that is detectable in response to a light source 294, as is done in conventional FACS systems. In general, a tag will associate with a particle or with a characteristic of the particle, for example with a marker associated with the particle. The tag can be a dye, fluorescent, ultraviolet, or chemiluminescent agent, chromophore, and/or radio-label, any of which can be detected with or without a stimulatory event to enable fluorescence. In some embodiments, certain particles may be naturally optically detectable without requiring a tag and in other embodiments, a tagged particle may be optically detectable without the use of a light source to stimulate a scatter response. The optically sensitive tag can be prepared with the sample 290 before introduction into the system 280, or the tag can be introduced some time after the sample 290 is introduced into the channels 282 and before the particles 292 reach the detection region 284 of the chip. A person skilled in the art will appreciate that any and all conventional FACS methods and techniques can be used with the system of the invention as noted above and as further described in connection with the illustrated embodiment. Once the sample 290 is introduced into the asymmetric channels 282, whether or not particles have been optically tagged, particles of a predetermined size can be focused into a single, localized and ordered stream of particles which will naturally flow into the second output channel 286 upon reaching the branch point.

An optical assembly 296 can be positioned in proximity to the detection region 284 of the chip and can generally include the light source 294, filters 298, optics 300, and a detector 302 positioned around the channel output, a distance before the branch point, for detecting optically sensitive tagged particles 292. The light source 294 can illuminate each individual particle in the stream of focused and ordered particles as they pass through the detection region 284 of the channel 280. As the particle is illuminated, the detector 302 can detect light scattered by the particle 292 and/or the tag associated with the particle 292, thereby identifying the particle as a predetermined type. Based on certain preset parameters, the detector 302 can communicate a signal to a controller 304 as to the type of particle passing through the detection region 284.

As a predetermined type of particle 292 passes through the detection region 284 and approaches the branch point, a controller 304 can, at the appropriate time, activate a change in a flow resistance associated with the first and second output channels 288, 286 using, for example, any of the microfluidic valves of the type discussed above. In one embodiment, a valve membrane or diaphragm 306 can expand under positive pressure into the second output channel 286 at the branch point, thereby increasing the resistance against the sample flow to prevent a tagged particle 292 from flowing into the second output channel 286. In the same way and at the appropriate time, a valve membrane or diaphragm 308 can expand under negative pressure out of or away from the first output channel 288 at the branch point, thereby decreasing the fluid resistance through the first output channel 288 and allowing the particle 292 to flow into the first output channel 288.

In another embodiment, the detection system can also include a Fluorescence Polarization (FP) system. A change in polarization of a particle tagged with a dye, over free dye, can enable gating and sorting of desired particles. Using FP, the tagged particles can further be separated on size differences because tagged particles with different sizes will exhibit different polarization values and can be differentially separated into individual outlets. A detector measures the FP value and signals the controller, which in turn changes the channel resistance appropriately, as described above, to direct the particles to an appropriate outlet.

As with the magnetic system of FIG. 15A, the fluorescence system of FIG. 15B can provide significant advantages over conventional systems. Because of the sharp focusing of particles, only slight changes of direction are needed to determine the direction of a particular particle, allowing for higher throughput with less noise. In addition, longitudinal ordering of particles significantly reduces noise as the system can more reliably distinguish the discrete positions of individual particles along the length of the channel and flow resistance changes in output branches can be more easily time for accuracy. So divided, the tagged particles 292, as well as any untagged particles, can be identified, sorted, counted, collected, and otherwise analyzed further as needed. A person skilled in the art will appreciate that any channel geometry can be used in this configuration, and any number of channels and channel branch points can be included to separate particle streams and perform sorting in parallel configurations.

In other embodiments, existing particle enumeration systems, for example flow cytometry, FACS, and/or MACS, can include a system of the invention to provide more accurate particle enumeration. A tightly focused stream of particles that is longitudinally ordered provides for extreme accuracy in the counting of particles of a predetermined type. Particles within a focused stream are ordered such that each particle can pass a predetermined point within an analytical region of a chip individually to be counted and analyzed, eliminating error due to clumping of particles.

In one embodiment, a system of the invention can be used to concentrate particles of a predetermined type from a dilute sample. Particles within a sample that are rare or dilute can be introduced into channels of the system having any geometry as noted above. The particles can be sorted and focused continuously and at high rates to achieve a concentrated sample in which the particles of a predetermined type are present with much higher frequency in a final sample in comparison to the original sample. Branches from a single channel and/or from multiple channels on a chip can be included to remove small volumes of focused particles from the original, dilute sample flowing within the channel to a collection reservoir containing the concentrated sample. A concentrated sample such as this can provide easier analysis and manipulation of rare particles and/or of particles that originate in a dilute sample.

Any number of system configurations can be provided for various applications, including sorting and counting as described above. Other system configurations can be designed to achieve certain specific results and/or properties associated with particle focusing within the various channel geometries. In the examples below, certain properties associated with the systems described herein will now be discussed in more detail. While certain experimental conditions may be discussed in reference to certain properties or parameters, it is to be understood that the properties and parameters are widely applicable to any of the channel geometries. Thus, a system of the invention can be configured in various ways for identifying, sorting, counting, and to achieve any number of the properties and parameters discussed in the examples below.

Example 1

Figure 16A:
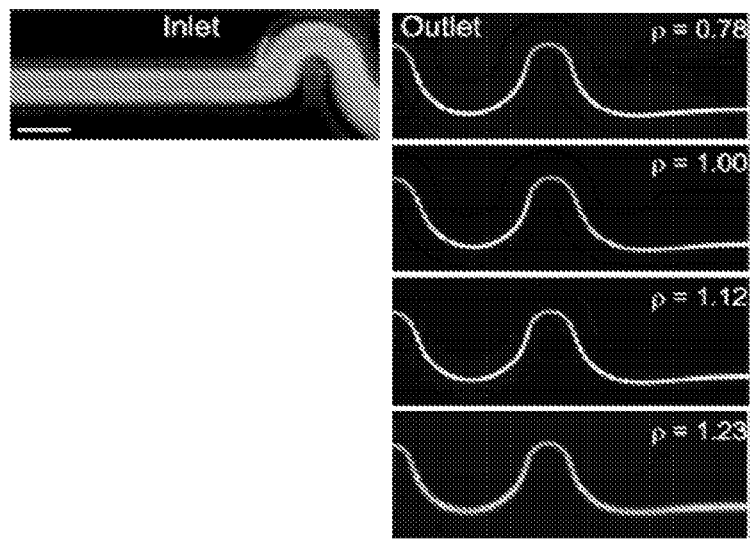
FIG. 16A is a side view illustrating focusing for various density particles.
Figure 16B:
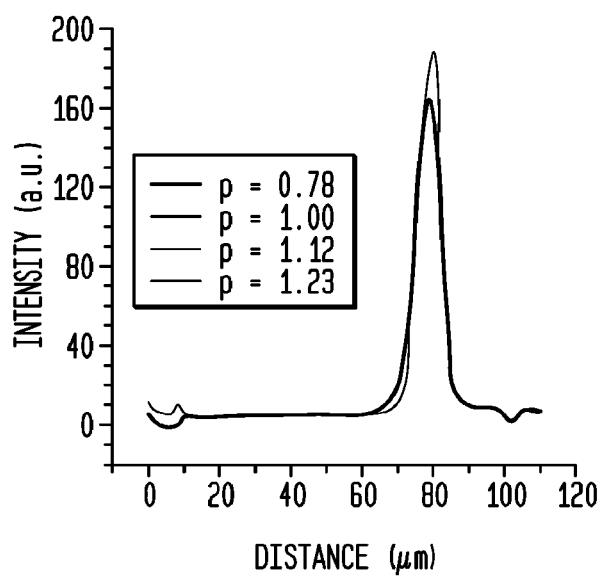
FIG. 16B is a graphical representation of data taken from FIG. 16A illustrating the independence of particle density.
Figure 16C:
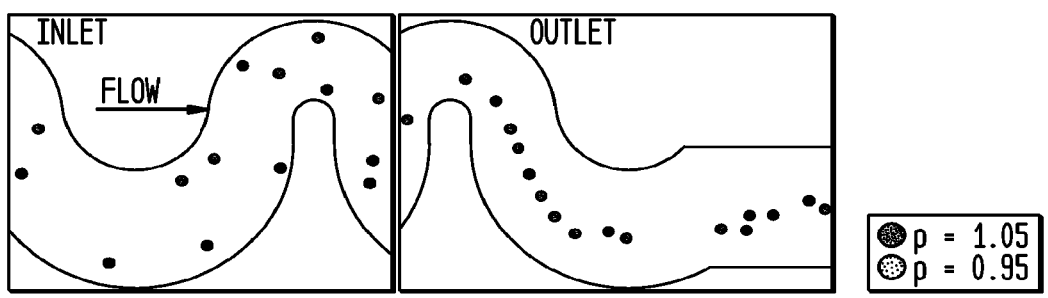
FIG. 16C is a side view of an inlet and an outlet of an exemplary system illustrating the independence of particle density.

Ordering and focusing of particles in the various channel geometries described herein is unaffected by relative particle density, as will be discussed in reference to FIGS. 16A-16C. When the density of the suspending solution is changed so that the suspended particles are either more or less dense than the solution (i.e., positive or negative buoyancy) focusing can be unperturbed and can remain at a consistent location, as illustrated in FIGS. 16A and 16B. For example, when particles both less dense (silicone oil, $\rho$=0.95 g/ml) and more dense (polystyrene, $\rho$=1.05 g/ml) than the suspending fluid ($\rho$=1.00 g/ml), are loaded simultaneously, both will focus to the same position, as shown in FIG. 16C. The independence of particle density for particle focusing is not consistent with a dominant centrifugal force acting directly on particles and suggests that Dean drag $F_D$ is the dominant effect leading to symmetry reduction.

In particular, as noted in detail above, effects present in curving channels include (i) an inertial (centrifugal) force on suspended particles ($F_{cfg}=\Delta m U_p^2/r$) and (ii) secondary rotational flows due to inertia of the fluid itself, Dean flow. For a constant geometry the average velocity of the Dean flow scales with the square of De. Two drag forces are considered that may act on suspended particles of radius, a, due to this secondary flow. Both viscous (Stokes) drag ($F_D=6\pi\mu a U_D$) and pressure drag [$F_p=(\frac{1}{2})\rho\pi U_D^2 C_d a^2$)] may be significant. Velocity conditions necessary for single focused streams allowed an order of magnitude calculation of the forces that may act in the system. For 10-μm particles in the range of channel velocities for successful focusing, $F_p$ was <5% the magnitude of $F_D$, indicating that viscous drag (1-10 nN) is still more significant because of the small particle sizes. However, as the channel velocity increases, pressure drag may play a more dominant role because it increases with the fourth power of $D_e$, while viscous drag increases with only the square of $D_e$. This contribution may be significant for particle motion in higher velocity regimes, where focusing to multiple streams occurs. In the same successful focusing regimes centrifugal forces on flowing particles are also less in magnitude than those due to viscous drag ($F_{cfg}$~0.1-0.4 nN).

Based on this preliminary analysis that neglects particle wakes and interactions with the flow field, it appears that the dominant force responsible for biasing particular stable positions is viscous drag due to the Dean flow. Additionally, particles with density less and greater than the suspending fluid would experience centrifugal forces in opposite directions (Δm is of opposite sign) and not lead to focusing to a single stream. This further suggests that Dean flow-induced viscous drag is the controlling force. An asymmetric channel may function as shown in FIG. 4. Here the viscous drag along the midline of the channel is larger, leading to directional bias, whereas particles already within the potential minimum, due to the superposed inertial lift forces, remain trapped. These particles cannot escape because of less viscous drag on the particle in the region where the two vortices split or rejoin.

Example 2

Figure 17A:
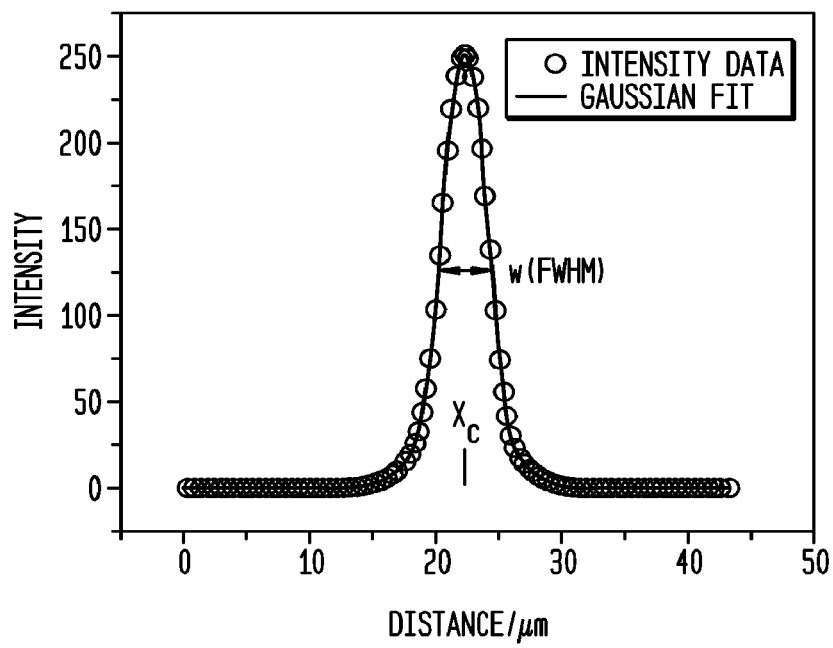
FIG. 17A is a graphical representation of the stability and precision of inertially focused particles showing intensity profiles fitted to a Gaussian.
Figure 17B:
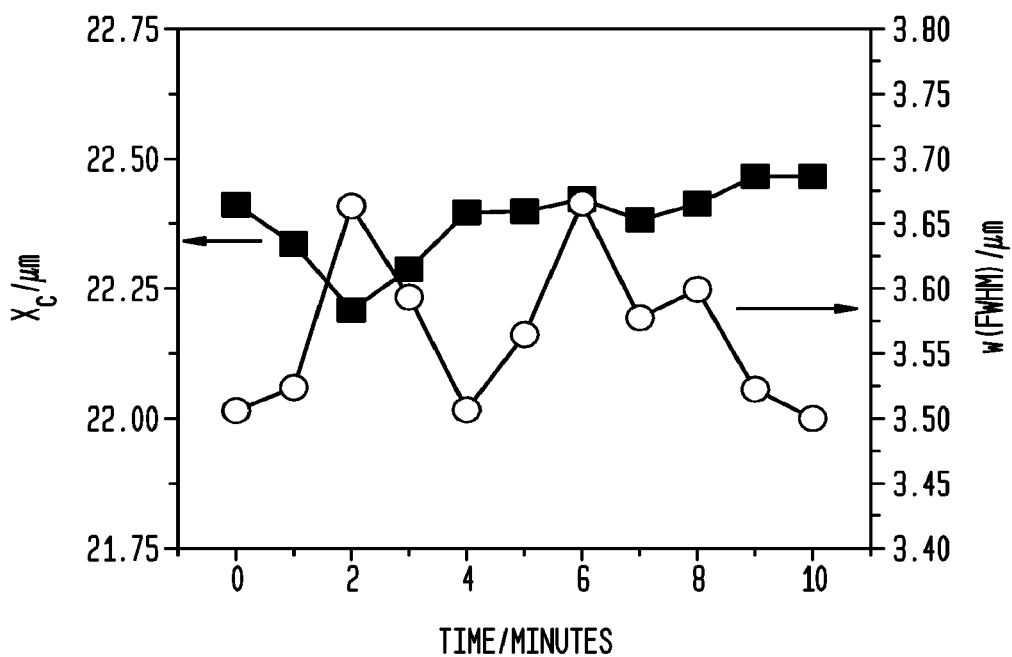
FIG. 17B is a graphical representation of data taken from FIG. 17A showing FWHM and center position of focused particles versus time.

Particles within the exemplary channel geometries described herein can be ordered and focused with extreme precision and with stability, as shown in FIGS. 17A and 17B. In particular, the stability of the focused streams of particles over time is assayed to demonstrate the utility of the phenomenon for focusing in flow cytometer and coulter counter systems. The stability and precision of inertially focused streams can be characterized by imaging a solution of 10-μm polystyrene particles over 10 minutes of continuous flow at $R_p$=0.24. In the example shown in FIGS. 17A and 17B, each image had an exposure time of 700 ms, sampling an average of 1,100 passing particles. In FIG. 17A, intensity profiles are obtained from each stream and a Gaussian fit is made to this profile. There are two parameters involved: the center position of the Gaussian fit and the full width at half maximum extracted and plotted for each time point. In FIG. 17B, these two parameters are plotted for each point on the same axis. The average full width at half maximum of the focused stream was 5% larger than the average particle full width at half maximum imaged on the same microscope system. The standard deviation of the center position of the focused stream was determined to be 80 nm in the y direction, and the focused stream's average width was only 1.05 times the average width of a single particle. Although other external forces, such as magnetic, optical, and dielectrophoretic, can also be used to bias a particular equilibrium positions within the rectangular flow field, an approach using hydrodynamic forces with a curved channel structure may be ideal. The additional forces increase with the flow rate, and only a minor geometric change is required to focus particles, with no additional mechanical or electrical parts.

Example 3

Figure 18A:
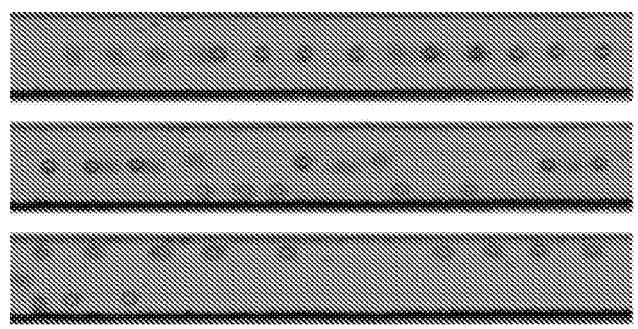
FIG. 18A is a side view of a channel of an exemplary focusing system illustrating the self-ordering of particles.
Figure 18B:
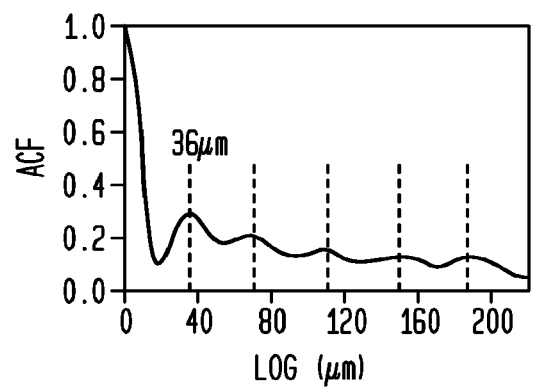
FIG. 18B is a graphical representation of the data taken from FIG. 18A.
Figure 18C:
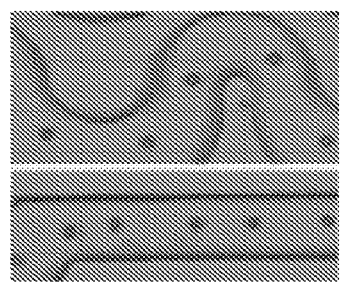
FIG. 18C is a side view of particle self-ordering within an asymmetric curving channel of an exemplary focusing system.
Figure 18D:
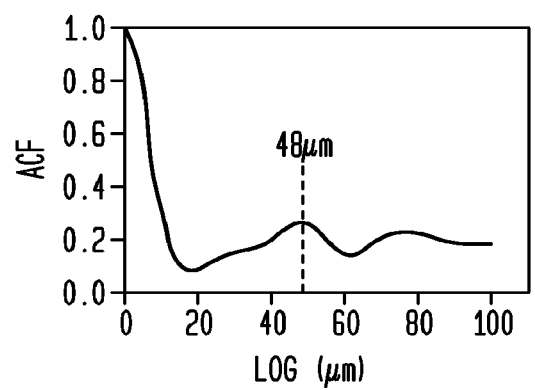
FIG. 18D is a graphical representation of data taken from FIG. 18C.

FIGS. 18A-18D illustrate that in addition to the focusing of particles across the transverse plane of the channel, self-ordering of particles in the longitudinal direction, along the flow lines can also occur. High-speed imaging (2-μs exposure) can be used to reveal characteristic long trains of particles (10-15 particles) with uniform spacing that alternate between the four stable lateral positions in rectangular channels, as shown in FIGS. 18A and 18B, or are concentrated in a single stream for asymmetric channels, as shown in FIGS. 18C and 18D. In particular, FIGS. 18A and 18C represent 10 μm diameter particles in a flow rate of $R_c$=120. As shown in FIG. 18A, trains of particles tend to alternate between positions instead of occupying several coincidentally. FIGS. 18B and 18D represent autocorrelation functions (ACF) that confirm particle ordering with an average distance of 36 μm in the straight channel and an average distance of 48 μm in the curved channel.

As illustrated by the above embodiment, particle-particle distances below a threshold are not favored, and self-ordering in a longitudinal direction results. A shorter preferred distance is observed at higher $R_c$ in rectangular channels than in asymmetric curved channels, as shown in FIGS. 18B and 18D. Ordered particle trains described herein are comparable to macroscale systems, where it has been postulated that preferred distances may arise from the interaction of secondary flows around rotating particles in a shear flow. In this case, the detached secondary flow itself may act as an object. For example, rigid particles (~0.5-mm diameter) in large (~1-cm diameter) cylindrical tubes will form long trains above $R_c$~450 with stable interparticle spacing decreasing with $R_p$. In the systems described herein, robust ordering occurs for a lower $R_c$~90.

Example 4

Figure 19A:
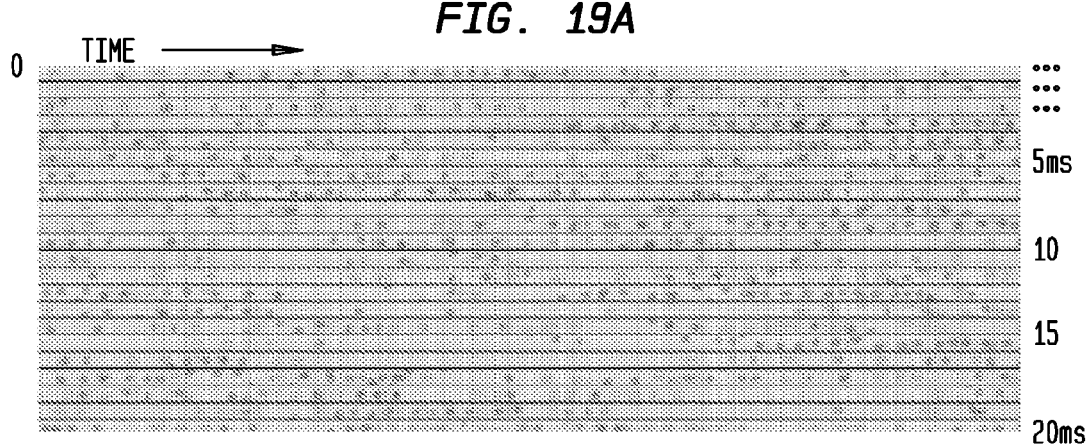
FIG. 19A is a side view showing self-ordering for cells in diluted whole blood within an exemplary focusing system.
Figure 19B:
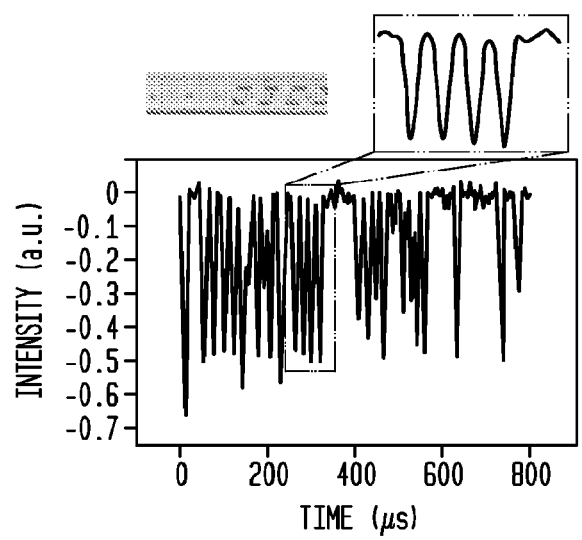
FIG. 19B is a graphical representation of a segment of a peak plot obtained from the date of FIG. 19A illustrating the in-focus particles.
Figure 19C:
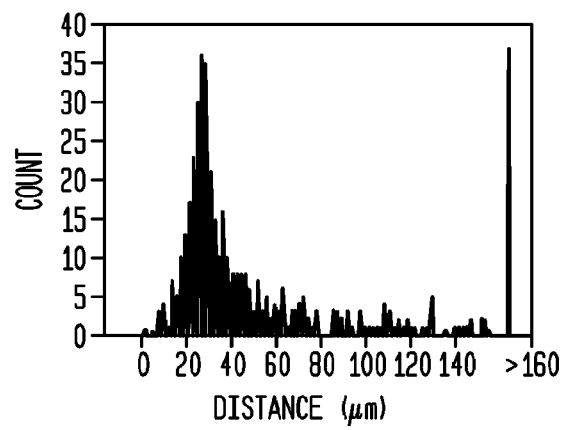
FIG. 19C is a graphical representation of a histogram of distances between particles in the system of FIG. 19A.

In another embodiment, additional particle ordering and alignment can be observed with reference to FIGS. 19A-20B. Self-ordering for cells in diluted (2% vol/vol) whole blood occurs as for particles in buffer solutions, as shown in FIG. 19A. Deformable particles such as cells may experience additional hydrodynamic forces in the applied flow field; however, from the experimental results whole blood, droplets, and cultured cells were found to behave as rigid particles in straight and curving microchannels. FIG. 19B illustrates a segment of a peak plot obtained from the image by data convolution with a kernel representing the in-focus particle. Intensity here represents the level of fit to an in-plane particle. Images at a rate of =15,000 cells per second were obtained in this system. Using a time series extracted from consecutive images, the particles flowing through the detection volume can be counted and analyzed as shown in FIG. 19C. A histogram of distances between particles is plotted demonstrating the limit on particle spacing that allows easy analysis (5% of particles are spaced closer than 16 μm apart).

Figure 20A:
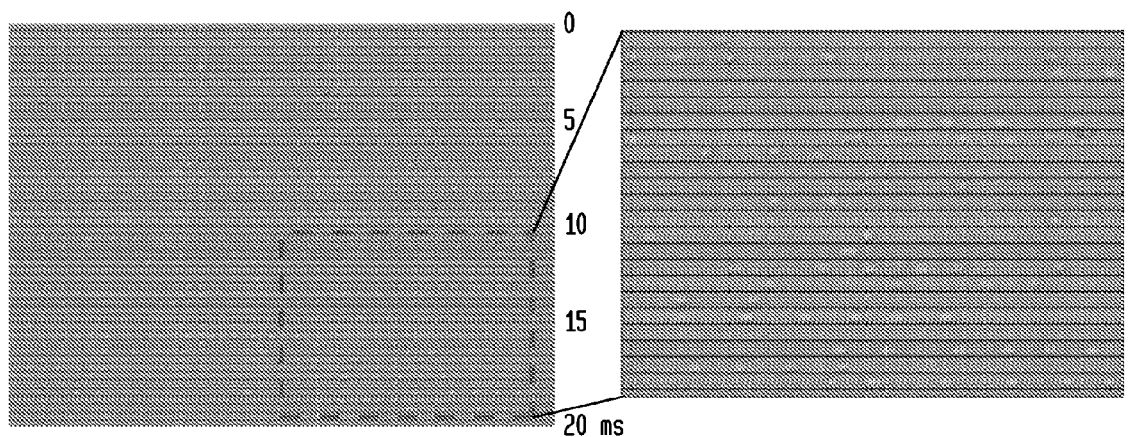
FIG. 20A is a side view representing a spatial mapping of the rotational, axial, and focal alignment of red blood cells is a channel of an exemplary focusing system.
Figure 20B:
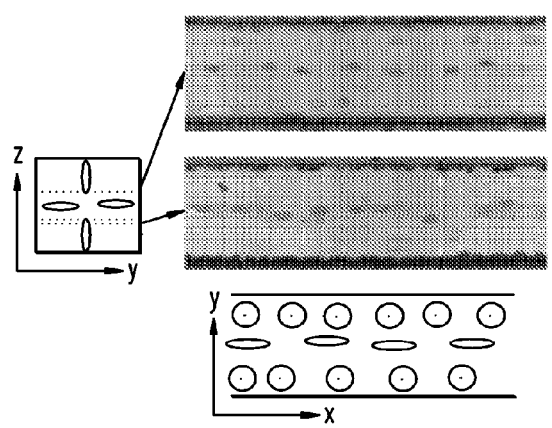
FIG. 20B is a side view and cross-sectional view of rotational alignment of discoid red blood cells within an exemplary focusing system.

A fourth dimension of axial rotational alignment in asymmetric particles can also occur within the channels described herein. FIG. 20A illustrates a spatial map of red blood cells flowing through the detector area over 20 ms. The rotational, axial, and focal alignment of the cells can be seen more clearly in magnification. Here, red blood cells are aligned with the disc face In the plane of the image. In particular, discoid red blood cells aligned rotationally such that the disk axis was parallel to the rectangular channel wall, as can be seen in most clearly in 20B.

Example 5

Figure 21:
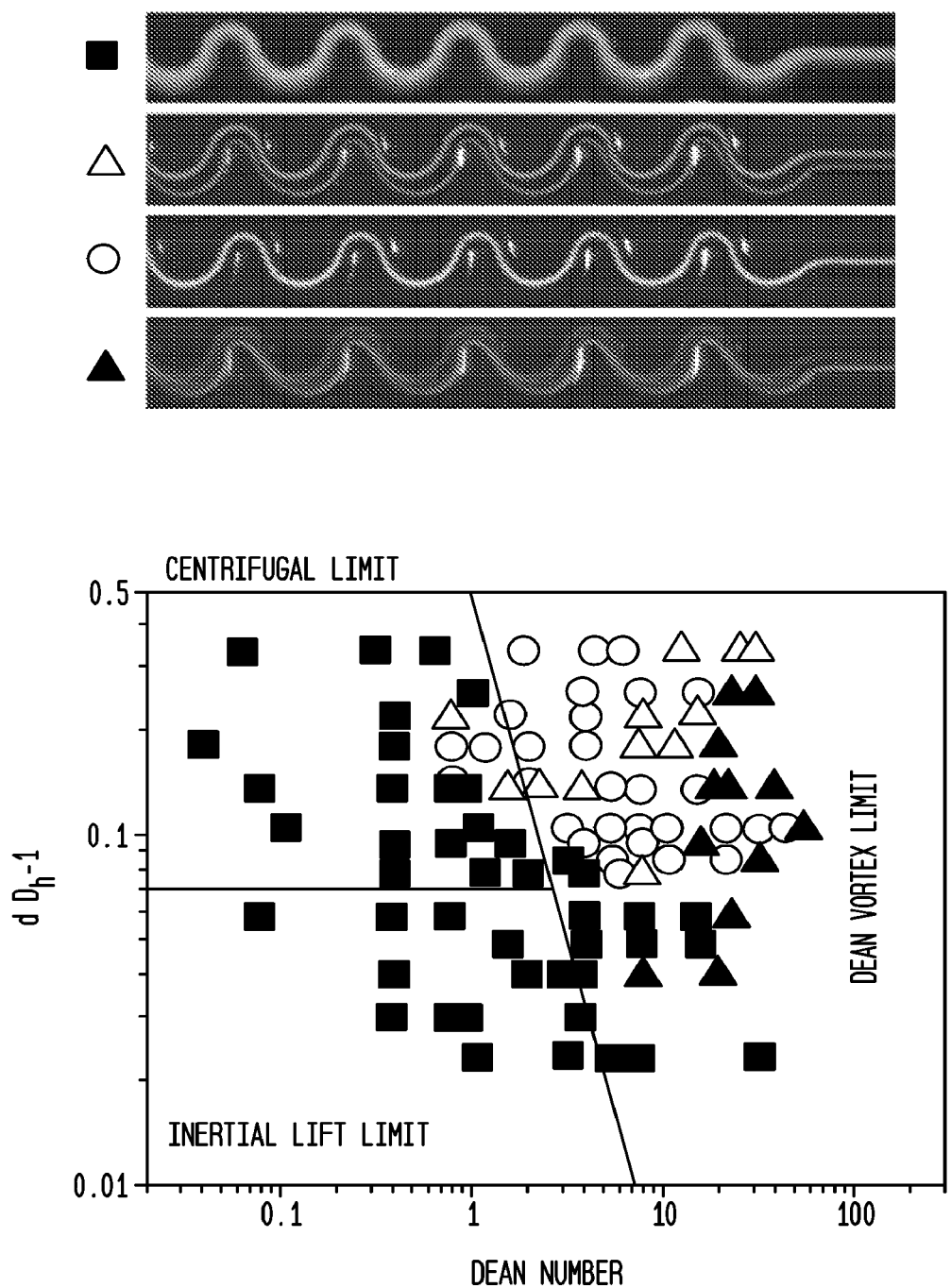
FIG. 21 is a graphical representation of focusing results for $a/D_h$ versus Dean number.

Referring now to FIGS. 21-22, various levels of focusing for cells and particles of different sizes are provided as applications in separation stem directly from the differential focusing of particles of different sizes. A range of particle diameters (2-17 μm) and channel sizes ($D_h$=10-87 μm) were tested over a range of $R_c$=0.075-225 for curving asymmetric channels. The focusing results were plotted as a function of $D_e$ and the ratio $a/D_h$, as shown in FIG. 21. In particular, as shown in the key above the plotted results of FIG. 21, no focusing corresponds to filled squares, focusing to two streams corresponds to open triangles, focusing to a single stream is represented by open circles, and more complex behavior is shown as filled triangles. Data for this graph was collected using various size particles (2-17 μm) as well as 4 different channel geometries.

The results shown in FIG. 21 apply universally for any diameter ratio and Dean number falling within a specific region independent of the specific geometry. For example a 2 μm particle in a 10 μm channel should focus to the same extent as a 200 nm particle in a 1 µm channel. In addition, the lateral distance traveled in a straight rectangular channel at constant $R_c$ can theoretically be shown to increase with $a/D_h$ cubed, yielding kinetic separations. In particular, FIG. 22 illustrates the dependence of particle focusing on $a/D_h$. Streak images at the outlet are shown 3 cm downstream of the inlet for a flow at $R_e=100$. The image is shown at the recombination of two branches to illustrate the uniformity of the flow profile from channel to channel. Focusing becomes more diffuse as $a/D_h$ decreases indicating a shallower potential well at the face in the y direction. This follows from the limiting case of an infinitely wide channel where no y force is present and focusing occurs only at the channel bottom and top. In fact, as the diameter ratio for particles in a square channel decreases, the channel starts to show characteristics of a circular channel with focusing in a modified annulus (note the high intensity at the edges for $a/D_h=0.04$). At a given distance focusing becomes more defined as $R_p$ increases following the dependence of $F_z$ on $R_p^2$.

For an asymmetric system, the additional effects due to Dean flow act along with inertial lift to shape the allowable range of particles and channel dimensions for successful focusing of particles into single streams. From the experimental data and theoretical calculations a large region for successful particle focusing can be defined where $a/D_h>0.07$. Below this value two effects scaling with $a/D_h$ may result in a loss of focusing: (i) inertial migration (scaling with $(a/D_h)^3$ is slower than what is required for complete focusing in the given length of the channel); or (ii) Dean drag becomes much larger than inertial lift for all values of $R_c$ as $a/D_h$ becomes small. Another limit is seen for $D_e>20$; above this level, drag from Dean vortices is larger than the inertial lift forces for most particle sizes and leads to particle mixing. Still, sufficient Dean flow is necessary to bias particular equilibrium points (a line of constant average Dean drag is drawn with the value $F_D=0.5$ nN). Last, a practical limit is seen for $a/D_h=0.5$, where particle obstruction of the channels may occur.

The data plotted in FIG. 21 appear similar to a phase diagram and are critical for determining the correct design conditions. In particular, a vertical movement on the diagram corresponds to changing particle size if channel geometries are held constant. To effect a separation, one must choose a region in the phase diagram (i.e., a specific geometry) where a small change in particle size leads to a change from a focused to an unfocused stream. Thus, one particle size is focused to a particular streamline and can be collected as an enriched fraction, whereas the other, smaller, particles are unfocused.

Example 6

Figure 23A:
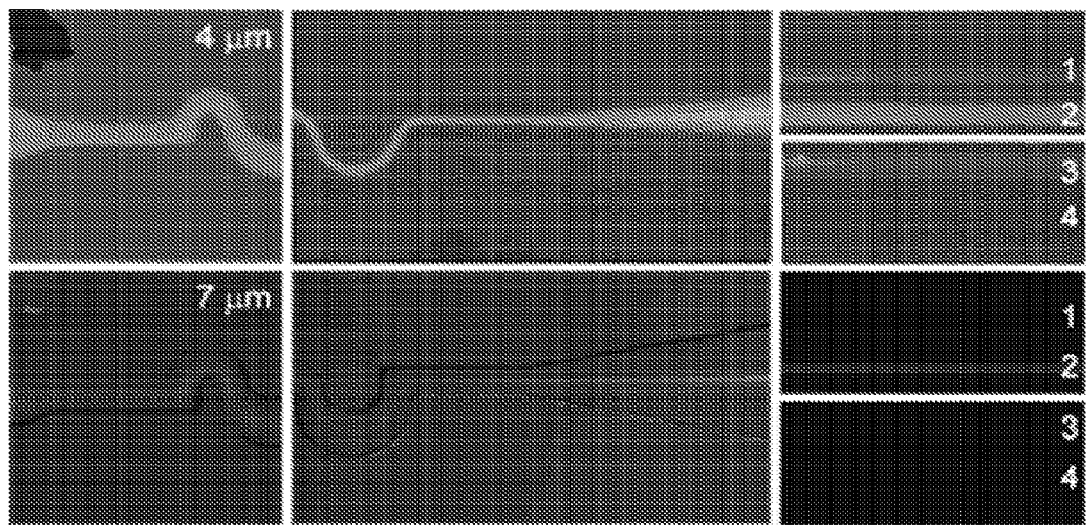
FIG. 23A is a side view of channels for focusing various size particles within an exemplary focusing system.
Figure 23B:
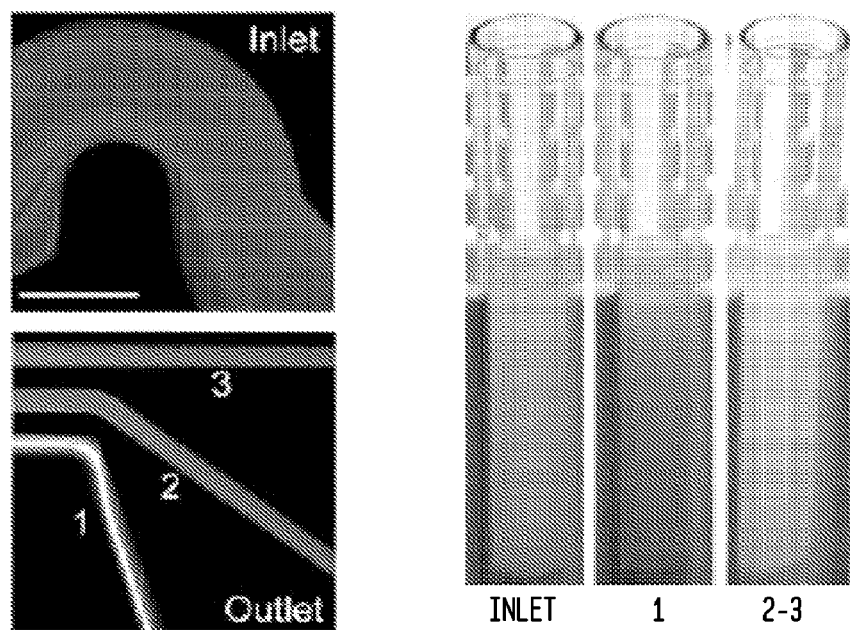
FIG. 23B is a side view and representation of a random distribution of particles at an inlet and the separation of particles at an outlet using an exemplary focusing system.

In other embodiments, high-throughput separations are possible with these systems because of the high $R_c$ at which they operate, an example of which is shown in FIGS. 23A-23C. For a flow rate of 1.5 ml·min$^{-1}$ of 1% particle solution a mass sorting rate of ~1 g·hr$^{-1}$ can be achieved for an unoptimized device that covers an area of 1.6 cm$^2$. Particles close in size (4 and 7 µm) can also be separated by tuning the asymmetric channel geometry, as shown in FIG. 23A, although with slightly less throughput. In these systems there are no externally applied forces other than the pressure to drive the flow, and therefore it is straightforward to cascade and parallelize these design elements, as shown in FIG. 23C, to enhance enrichment and throughputs to very high levels, or combine elements with different hydraulic diameters to separate across more than one size threshold. Ideally pure fractions can be collected through the use of multiple outlets as shown in FIG. 23A in which streak images show at the left, focusing is shown in the middle frame, and four collection channels are shown at the outlet demonstrating the feasibility of the separation in a channel 1 and 3. FIG. 23B further illustrates such a separation. The inlet is shown having a random distribution of particles therein. One type of particle can be focused and separated out from the rest of the sample and three different outlets 1, 2, and 3 can be provided as shown. The focused particles can be directed into outlet 1 and collected in a reservoir as shown, while the rest of the sample is collected in outlets 2 and 3. Typical of most microfluidic systems, a throughput of 30 mg·hr$^{-1}$ was described for deterministic displacement with a device area of 15 cm$^2$. In applications dealing with rare cell cytometry and purification or industrial filtration, however, increased throughput is essential.

Example 7

Figure 24:
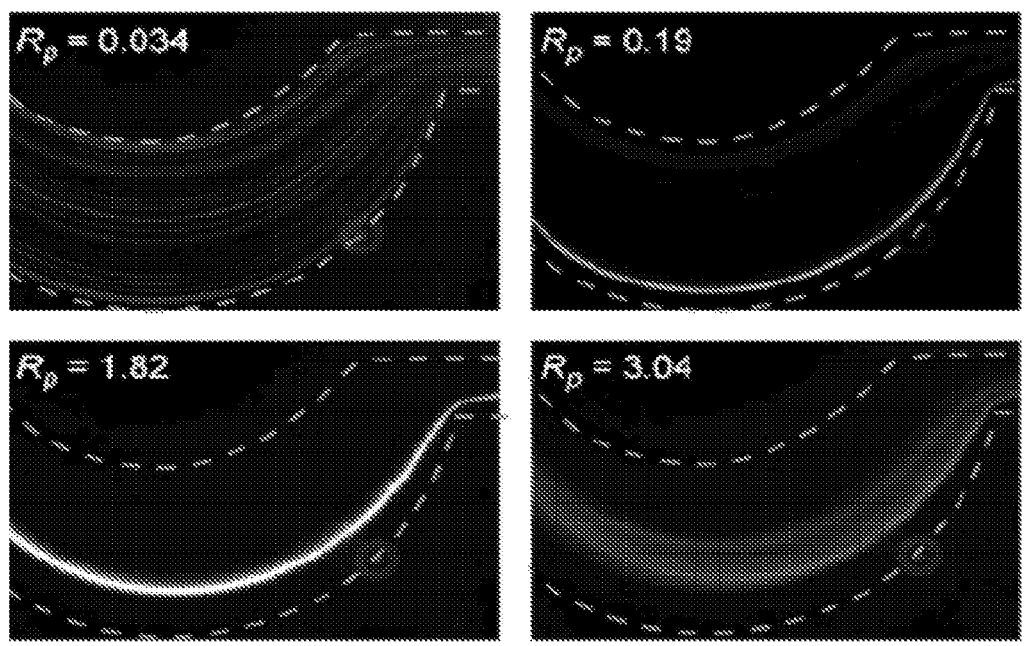
FIG. 24 is a side view illustrating particle separation behavior for various $R_p$ within an exemplary focusing system.

Referring to FIG. 24, rapid (1 mL/min) separation and filtration of rigid particles, emulsions, and blood components is also provided. In one embodiment, flow conditions in the system were tuned to achieve the best particle focusing with the highest possible flow rates. Streak images of 10 µm fluorescent beads are shown at various controlled flow rates in the system described herein. As shown in FIG. 24, for low channel Reynold's numbers, particles are seen to be distributed randomly throughout the channel width. As $R_p$ increases, there is a gradual change to one focused streakline near the outer edge of the larger width channel. For $R_p$ larger than ~2, the particle stream again becomes more diffuse. It is also observed that the position of the focused streakline moves out from the wall of the larger turn increasing particle Reynold's number. Using this data, an optimal flow rate of, for example, 0.9 mL/min ($R_p=1.53$) can be used to operate the systems described herein for exemplary separation applications.

Example 8

Figure 25:
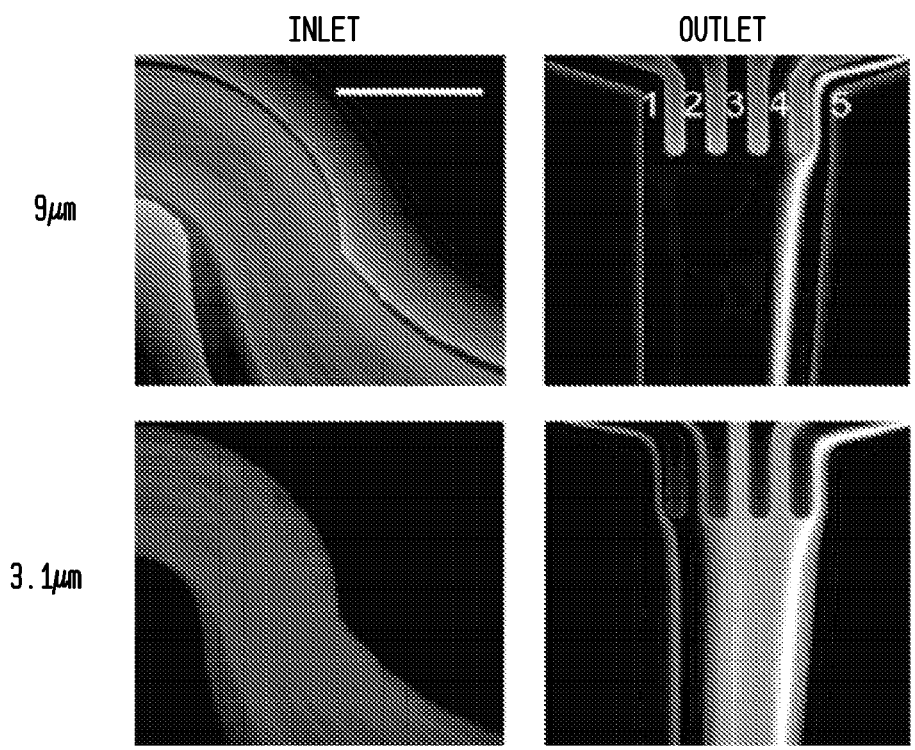
FIG. 25 includes top views of particle distribution at an inlet and particle separations at an outlet for various particle sizes within an exemplary focusing system.
Figure 26A:
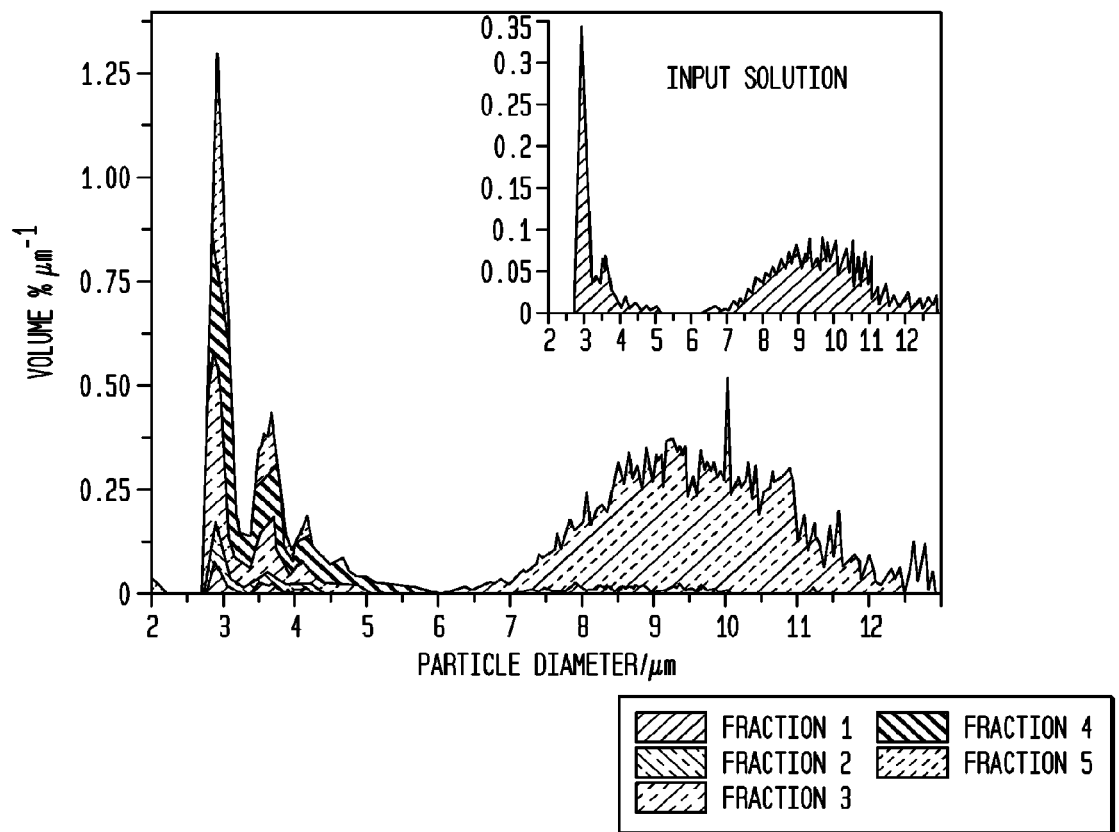
FIG. 26A is a graphical representation of particle diameter distributions for an input solution and various output fractions within an exemplary focusing system.

Referring now to FIGS. 25-27, a flow rate of 0.9 mL/min, 20 mL of a mixture of 9.0- and 3.1-µm diameter polystyrene beads can be introduced into the system. As shown in FIG. 25, fluorescent streak images reveal essentially uniformly distributed particle positions at the input for both particle sizes. At the outlet of the device, 9.0-µm-diameter particles can be observed in a focused streakline, while 3.1 µm particles remained unfocused. In one embodiment, five fractions were collected from the system and were labeled according to the scheme in FIG. 25. Particle diameter distributions were obtained by Coulter Counter for the input solution and various outlet fractions, a distribution of which is shown in FIG. 26A. The size distribution for 3.1 µm particles was narrow and contained a few extra peaks at 3.6 and 4.2 that correspond to two and three aggregated particles. For all output fractions, there were significant levels of 3.1 µm particles; however, the significant majority of the distribution of particles centered on 9-µm were collected from fraction 5.

Figure 26B:
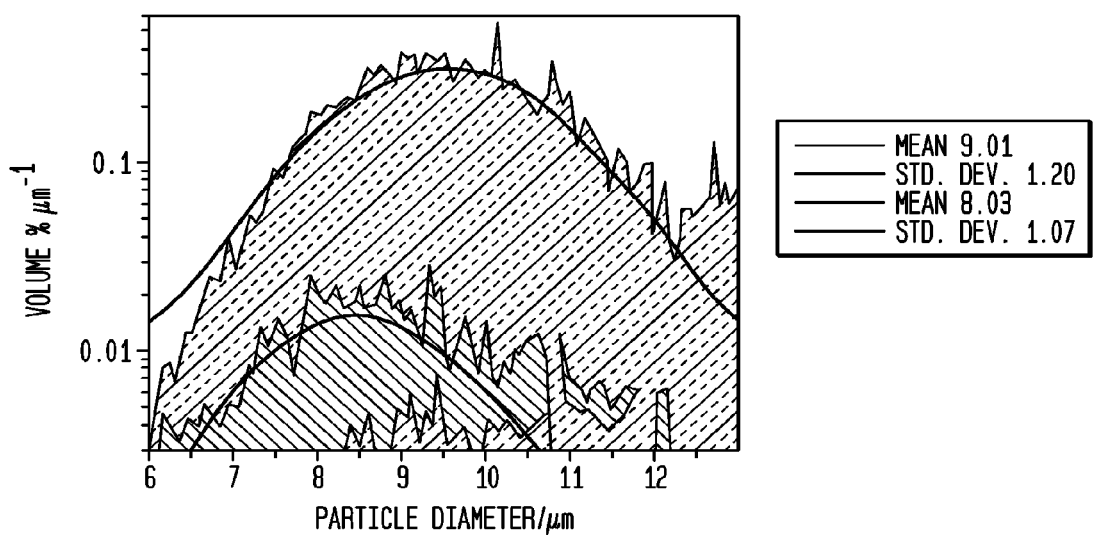
FIG. 26B is a graphical representation of one portion of the graphical representation of FIG. 26A illustrating the presence of larger particles.

Fraction 4 also contained some larger particles, as shown in FIG. 26B, where interestingly, the collected particles had a lower mean centered on 8-µm with a distribution that was 20% narrower than the initial distribution of large particles. The mean and standard deviation of the collected particles were determined by fitting the counts to a Gaussian distribution. The purity and yield for filtration of large particles from 3.1-µm particles is shown in FIG. 27, where percentages refer to absolute particle numbers. Purity is defined as the percentage of total particles in a fraction of the filtrate that were 3.1-μm in diameter, and yield is the percentage of total 3.1-μm particles recovered. As shown in FIG. 27, there are definite trade-offs between yield and purity, which can be useful for deciding collection strategies for particular applications.

Example 9

Another embodiment of the system can be described with reference to FIG. 28. Because large quantities of particles can be filtered in relatively short periods of time, separations like that shown in FIG. 25 can be easily cascaded in series to reach higher levels of enrichment if filtrate from the five outlets is merged into two pools. FIG. 28 presents data for a cascaded separation with two tiers. In one embodiment, filtration from fractions 1-4 were pooled and run through the system again, and the same was done with fraction 5. Key parameters that are reported at each tier are the absolute numbers of particles, the ratio between 3.1- and 9-μm particles (ratio 3/9) and the enrichment ratio (i.e., the tier X 3/9 ratio divided by tier 0 3/9 ratio). This sample consisted of pooling fractions 1-4 of the first pass, running this through the system, and collecting fractions 1-4 again. Notably, after two tiers of separation, ~56% of the initial 3.1-μm particles were collected in a sample, where the number of 9-μm particles was reduced by 3 orders of magnitude (i.e., 99.9% purification).

Example 10

Figure 29A:
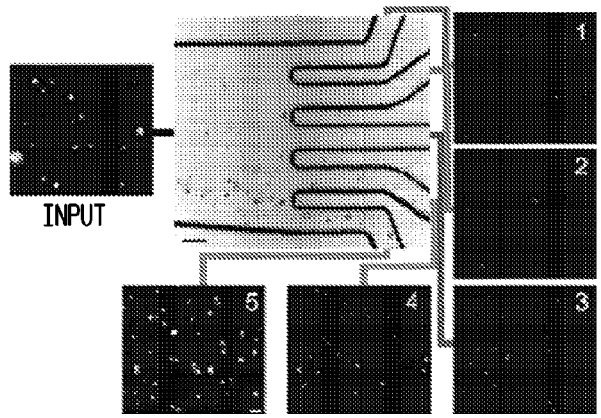
FIG. 29A is a representation of an exemplary focusing system for separating various sized deformable silicone oil droplets.

In this example, the behavior of deformable particles is illustrated. In particular, droplets of a fluid that is generally immiscible in solution are shown to behave much like other particles in their focusing behavior in channels. In embodiments shown in FIGS. 29A-29C, various sized silicone oil droplets that are not rigid can also be separated using the system described herein. A continuous distribution of silicone oil droplets ($\rho$=0.95 g/cm$^3$, $\mu$=10 cst) (ranging in size from <1 to 20-μm) can be introduced into the system at a flow rate of 0.9 mL/min, as shown in FIG. 29A. In particular, as shown, the input solution of droplets is well mixed. After passing through the separation channel, larger droplets are seen to focus while smaller droplets remain unfocused. The five collected fractions showed obvious differences in content of large droplets by phase contrast microscopy that corresponded with the video results of focusing streamlines shown in FIG. 29A. The fractions also showed particle size distributions, represented in FIG. 29B, that agreed well with the microscopy data. The continuous droplet size distributions for the collected fractions clearly show a size cutoff for separation with the exemplary geometry (3.7-μm by fitting the data from fraction 3 with a Boltzmann sigmoidal function to accurately determine the position of 50% depletion).

Figure 29B:
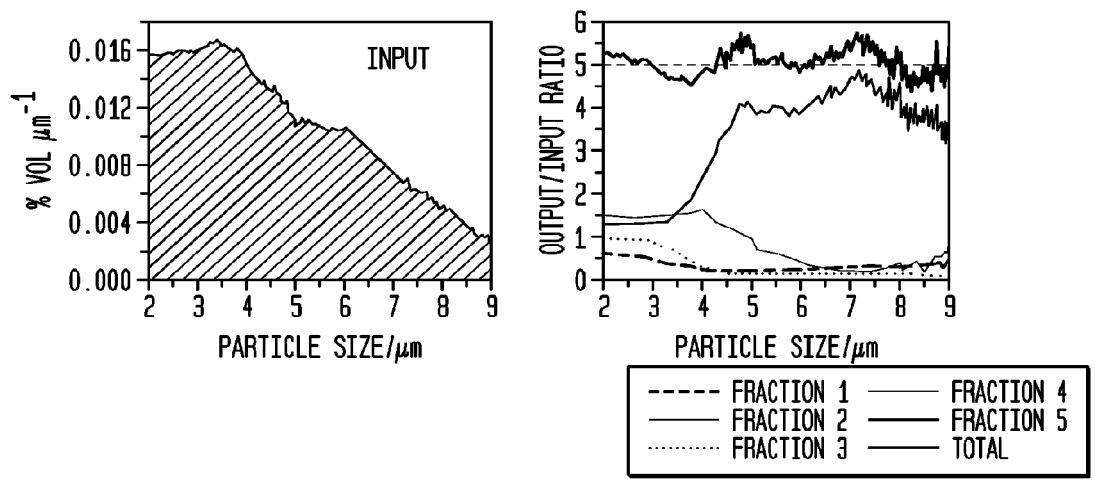
FIG. 29B is a graphical representation of particle size distributions for the system of FIG. 29A.
Figure 29C:
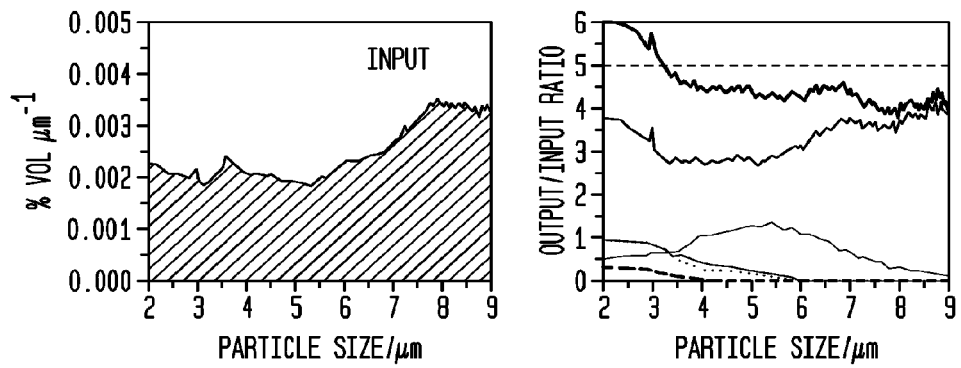
FIG. 29C is a graphical representation of particle size distribution for rigid particles flown in the system of FIG. 29A.

Following the distribution shown FIG. 29B, one can estimate that equal numbers of 4.5-μm particles could be filtered from 3-μm particles with a separation purity of >90% with 50% of the 3-μm particles being recovered. Interestingly, size cutoffs for rigid particles are similar to that of deformable particles. For example, rigid PDMS beads with a different distribution ranging from <2 to 40-μm were fractionated using the same system and flow settings, as shown in FIG. 29C. In this case, the size cutoff of fraction 3 was determined to be 4.0-μm slightly higher than for deformable particles. Another noticeable difference is the larger concentration of smaller particles in fraction 5 and the reduction in larger particles in fractions 1-3. Overall, the separation behavior for rigid and deformable particles appears remarkably similar, with the bulk of large particles collected in fraction 5 and to a lesser extent 4. In both cases, fraction 2 has the lowest concentration of particles over the entire size range.

Example 11

Figure 30:
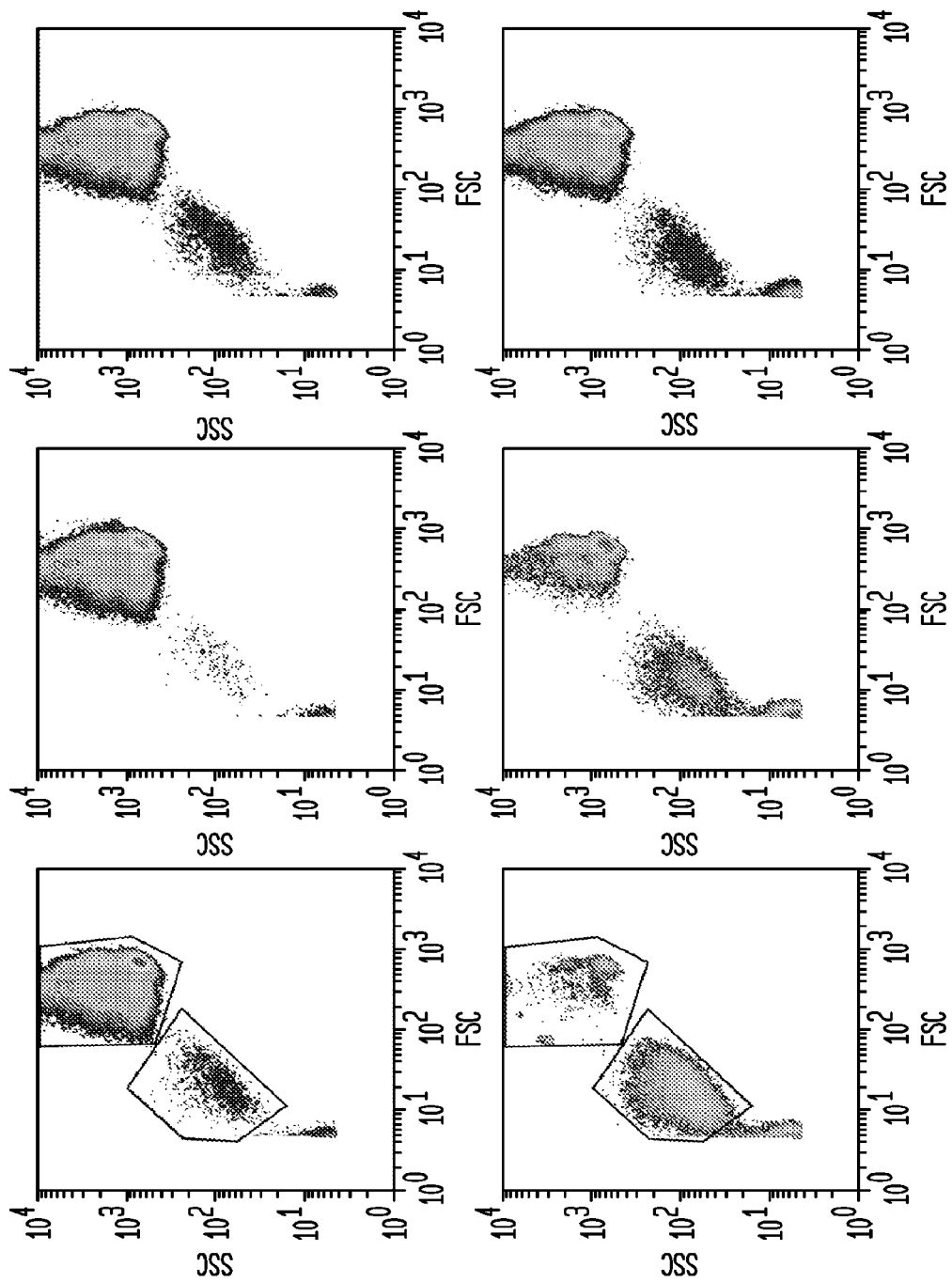
FIG. 30 is a graphical representation illustrating a size cutoff for the separation of platelets from other blood components.

The size cutoff for an the exemplary system described above is useful for separation of platelets (2-4 μm) from other blood components, as illustrated in reference to FIG. 30. In one embodiment, the separation of platelets from blood cells in diluted blood (2% whole blood in PBS) can be examined using a same flow rate of 0.9 mL/min. The cellular components of blood range in size from 7 to 15-μm for spherical leukocytes (WBCs), to 6-8-μm×2-μm for discoid RBCs, while platelets are between 2 and 4-μm in diameter. One microliter of blood contains ~5×10$^6$ RBCs, (2-5)×10$^5$ platelets, and (5-10)×10$^3$ WBCs$^2$. The original blood solution diluted to 2% was examined by flow cytometry, as shown in FIG. 30. The initial number ratio of platelets to other cellular components in blood was 0.04. After passing 10 mL of diluted blood (200-μL whole blood) through the system and collecting the five various fractions, enrichment or depletion of the platelet population was observed. In fraction 5, the amount of platelets was depleted compared to larger cells by a factor of 2, while in fraction 3 the relative amount of platelets was enriched by a factor of 100.

Example 12

The experimental data suggesting an optimal flow rate for focusing agree with theoretical predictions, despite theoretical assumptions of small $R_p$. At a low maximum channel velocity ($U_m$), lift is dominant; however, there is not enough distance in the channel for particles to reach equilibrium positions, as previously illustrated in FIG. 24 in the channel having the low particle Reynolds number $R_p$. As $U_m$ increases, the ratio of lift to drag forces ($R_D$ approaches 1; here a single equilibrium position is favored due to the superposition of Dean drag and inertial lift forces, shown in the two channels having middle Reynolds numbers $R_p$ in FIG. 24. As $U_m$ increases further, $R_f$ becomes less than 1 over the channel cross section and focusing is perturbed by Dean drag, as illustrated by the channel with a high $R_p$ in FIG. 24. These results suggest that theory for finite $R_p$ should have a dependence on increasing flow velocity similar to the small $R_p$ theory used.

Using the experimental data determining size cutoffs for focusing, a semi-empirical relationship to predict future geometries that would focus at given size cutoffs can be developed. For the particular conditions described herein, $R_f$~1 for a particle diameter of 4.0-μm, a hydraulic diameter of 90-μm and $R_c$=115. To determine a new geometry for a size cutoff $a_c$, the experimental parameters can be substituted into the following equation:

$$r_2 \frac{a_{c2}^3}{D_{h2}^4} = 3.2 \times 10^{-4}$$

Assuming that the radius of curvature is left constant in a new system, the new hydraulic diameter is a function of the desired cutoff:

$$D_{h2} = a_c^{3/4} m^{1/4}$$

This relation suggests that, for a cutoff of 8-μm, a $D_h$ of 150-μm is required for a channel height of ~95-μm if the width remains constant. This value can be acquired for the scaling of the balance of forces based on a single geometry; determining whether the value converges for separate geometries would provide further support for this approach. Overall, the semi-empirical approach provides the scaling for the ratio of lift to drag forces without providing the magnitude of the individual forces. The speed of focusing, based on the magnitude of lift forces, can be calculated from the fundamental equations.

Blood cells may be considered to fall on the continuum between rigid particles and deformable droplets; however, since droplets are measured to have a size cutoff similar to rigid particles (3.7 vs. 4.0-μm) the equations presented above are also applicable to cells. The lack of a disparity between deformable droplets and rigid particles suggests similar ratios of inertial lift to Dean drag forces with little additional contributions. The differences, including the relative reduction of smaller particles in fraction 5 of the sorted droplets and the reduced collection range in fraction 4, may be due to forces that are known to act on flexible particles due to deformation in the flow namely, deformation-induced lift forces that additionally act to push deformable particles toward the channel center. These differences, however, should be small in the inertial flows since inertial lift forces have been shown to dominate droplet behavior for small drops or when the viscosity ratio between droplet and suspending fluid is 1 or greater. For highly viscous droplets or cells, the droplet can be expected to behave almost as a rigid particle.

Example 13

Figure 31:
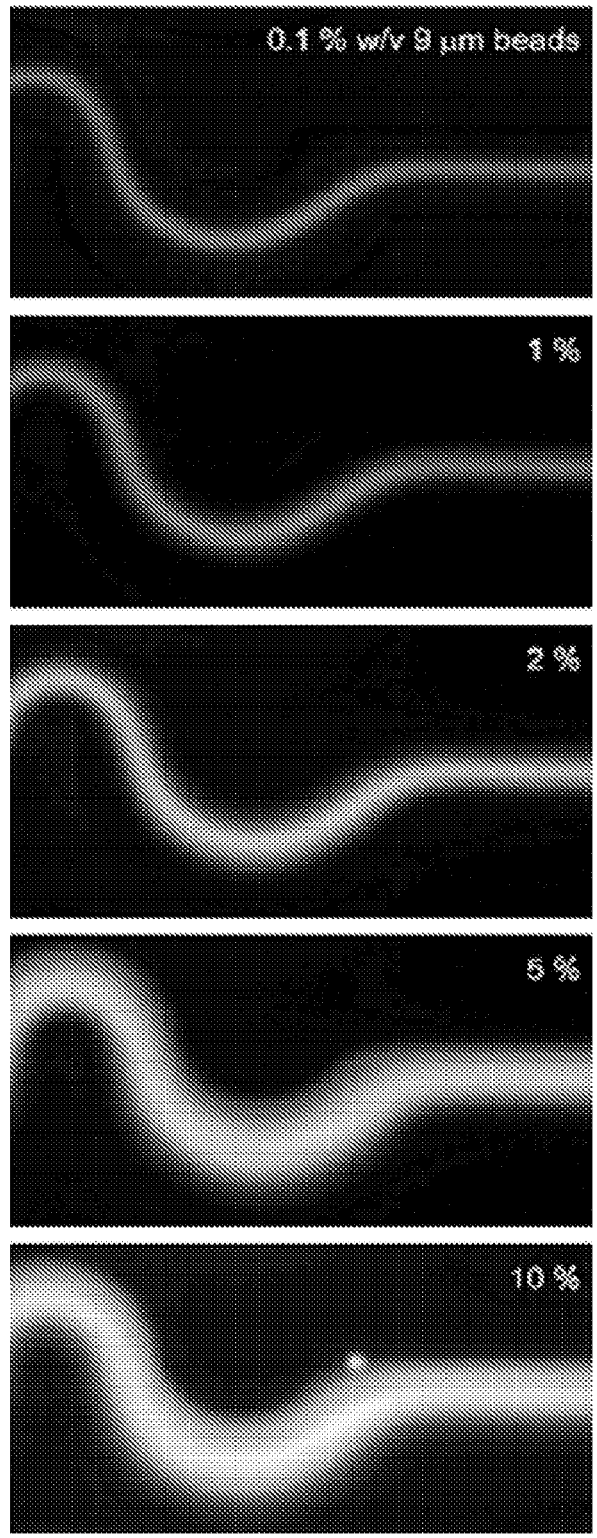
FIG. 31 is a side view of an exemplary channel illustrating focusing in solutions having different total volume fractions.

Referring to FIG. 31, inter-particle interactions can play a role in separations, leading to varied behavior for solutions with different total volume fractions. Because the system focuses particles to particular streamlines, one upper limit of particle concentration of ~5% can be calculated, in which all particles are in contact and aligned in a single file. However, even below this concentration, particle-particle effects can limit the degree of focusing. Particles randomly disturb the ideal parabolic flow of the fluid necessary for precise values of inertial lift and Dean drag, as can be seen in FIG. 31. In particular, FIG. 31 illustrated particle concentration effects on ordering. Fluorescent streak images are shown for increasingly concentrated solutions of 9-μm beads flowing through 50-μm focusing channels. Ideal focusing to a single stream is seen at 0.1% volume fraction of polystyrene beads. Focusing at 1% also remains relatively unperturbed. As concentrations increase further, the focusing is perturbed to a greater extent. A maximum concentration for which focusing could be possible into a single-file stream is ~4% for this geometry, but this calculation assumes particles are touching, and is not physical. Below this concentration focusing is still disturbed because beads change the ideal flow pattern in their vicinity as they traverse the channel.

Example 14

Referring back to FIG. 23C as well as to FIG. 30, cell viability can be maintained during inertial focusing. Because cells travel at high velocities (~0.5 m/s), it is important to evaluate cell viability and damage during this process. It should be noted that cells traveling at steady state with the fluid experience only small normal and shear stresses over their surfaces, while significant forces are briefly felt in the inlet and outlet regions where cells must be accelerated by the fluid. In the systems described herein, the channel width at the inlet can optionally be gradually tapered to minimize this effect. High cell viability is found by vital stain after passing through an exemplary system. Further evidence of little damage is seen in FIG. 30, where scatter plot width and position for blood before processing appears essentially unchanged after passing through the system. Cell debris and blebbing would produce a broader distribution of scatter.

No significant alterations in cell viability occur after they are passed through the inertial focusing systems described herein at high speeds. Even at average velocities of 0.5 m/s there was no discernable damage to cells (99.0% vs. 99.8% initial viability as measured by using a fluorescent live/dead assay). High cell viability and throughput are critical for applications such as flow cytometry. With inertial self-ordering, clear advantages emerge compared with hydrodynamic focusing used in current flow cytometers. These include (i) a single stream input, (ii) reduction of multiple cells in the interrogation spot because of longitudinal self-ordering, and (iii) angular orientation of nonspherical particles for uniform scatter profiles. Another powerful advantage of this focusing system is that throughput can be easily scaled by parallel channels, as noted above and as shown in FIG. 23C, because additional fluidic channels for the sheath fluid are not required. FIG. 23C demonstrates parallelization of particle alignment for high-throughput analysis. Sixteen parallel channels can be fed from an initially randomly distributed solution of 10-μm particles. A uniformly distributed input can be focused into 16 stable streams at the outlet.

Example 15

The relative separation performance of the system can also be considered herein. In particular, it is important to characterize the relative performance of the separation embodiments disclosed herein by determining several key figures of merit, which are applicable in different situations. In most cases it is difficult to compare between various techniques, since usually only a single figure of merit that best suits the application is reported. Here four quantifiable measures of performance for separation systems are proposed that would allow easy comparison from device to device: (1) throughput, (2) enrichment ratio, (3) yield, and (4) separation resolution. As trade-offs between the various measures are possible by changing the conditions of separation, these parameters should be reported together for each reported condition. The throughput of the system is defined as the amount of volume sorted in a given time period. The throughput ($Q_m$) can be given by $Q_m=Q_\Phi$, where Q is the volumetric flow rate, and $\Phi$ is the volume fraction of particles input. Additionally, for most systems increasing the device footprint (i.e. parallelization) increases the device throughput linearly. Therefore the throughput per unit area (mL hr$^{-1}$ cm$^{-2}$) is a useful measure. In one exemplary system, a throughput of 0.6 mL hr$^{-1}$ was achieved with a device area of 2.5 cm$^2$. Enrichment ratio is defined as the number of selected particles to unselected particles in the filtrate divided by the initial fraction of selected/unselected particles ($s_f/u_f s_i/u_i$). Thus, enrichment is dependent on depleting the unselected particles but also on maintaining high yields of the selected particles ($s_f/s_i$). In the systems described herein, enrichment ratios of 8-∞ corresponded to yields of 60%-5%, after a single pass. An enrichment ratio of ∞ corresponds to zero unselected particles present in the filtrate. The separation resolution is a measure of the size difference required for successful separation (a smaller number is better). It is defined as the size difference required for >90% depletion of the unselected particles, divided by the fractional yield of selected particles. Using FIG. 24B, in one embodiment, a single pass provides for 1 log enrichment in separation of particles with 3-μm resolution.

Example 16

Figure 32A:
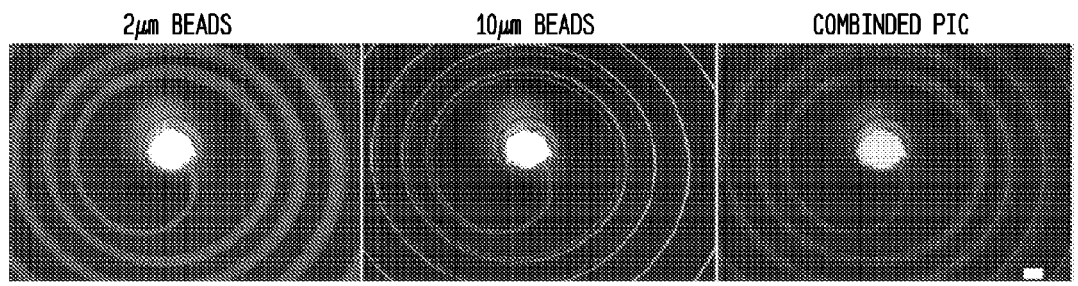
FIG. 32A is a top view of the focusing of particles within an expanding spiral channel of an exemplary focusing system.
Figure 32B:
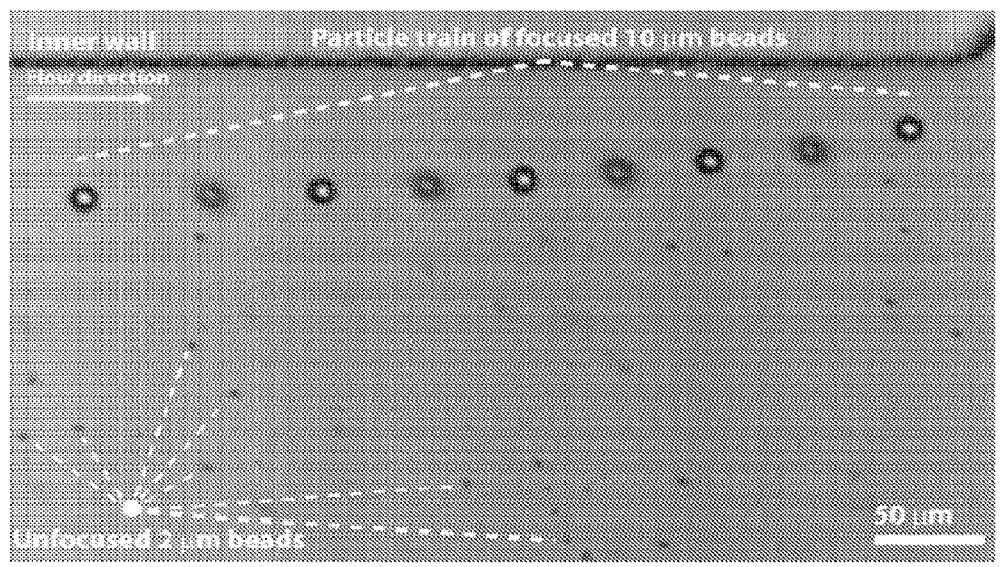
FIG. 32B is a side view of the longitudinal ordering of various particle sizes within the channel of FIG. 32A.

Referring now to FIGS. 32A-32B, in one embodiment, a system is provided for focusing particles above a certain size while smaller particles remain unfocused for a given geometry. To investigate the relationship between particle size and channel geometry, a mixture of 10-μm and 2-μm beads were flown at varying flow rates through a channel having an expanding spiral configuration. As can be seen in FIGS. 32A and 32B, the smaller 2-μm particles remain unfocused, while the 10-μm particles quickly focus and remain focused at different turns of the spiral. We tested different flow rates and the 2-μm particles remained unfocused irrespective of flow rate, supporting the theory of a optimal particle size to channel geometry below which no focusing can occur. High-speed camera result shown in FIG. 32B illustrate that the larger 10-μm particles are focused in a single stream very close to the inner wall, while the 2-μm particles are scattered all over the channel.

The larger 10-μm particles remain focused over a wide range of $R_c$ due to the dominant lift forces balancing the secondary Dean flow pushing the particles to the outer wall. The larger 10-μm particles are focused closer to the inner wall, enabling almost 100% recovery of the enriched 10-μm particles fraction. The focusing of particles is not limited to rigid particles, but also non-rigid biological material. Cells were also successfully focused to single streams, opening up opportunities for high throughput processing of biological components.

Example 17

Figure 33A:
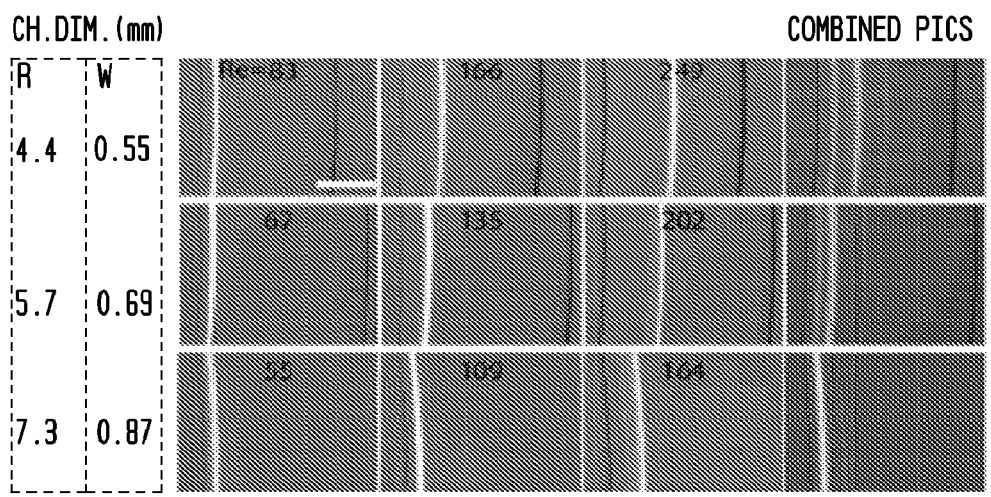
FIG. 33A is a representation of the lateral displacement of particles within an expanding spiral channel of an exemplary focusing system.
Figure 33B:
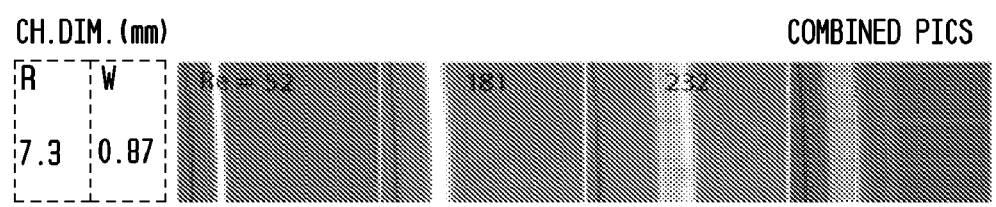
FIG. 33B is a further illustration of the lateral displacement of particles within the channel of FIG. 33A.
Figure 33C:
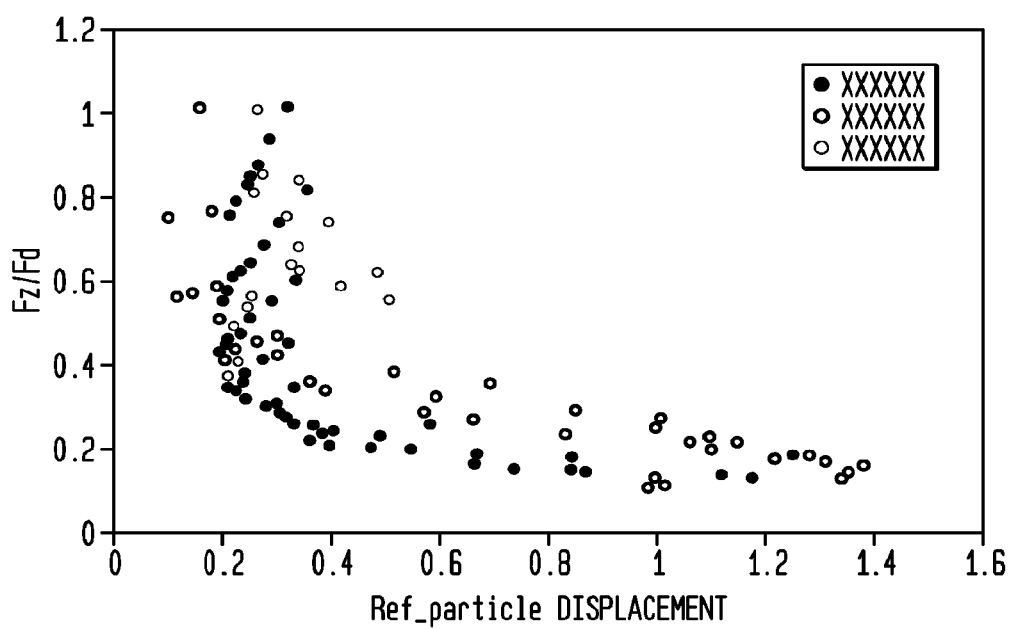
FIG. 33C is a graphical representation of the lateral displacement of particles for various $a/D_h$.

To test the effect of $R_c$ on the lateral positional displacement of focused particles within a spiral channel, 10-μm particles were flown at a large range of flow rates (0.1-5.5 mL/min) for given channel geometry and radius of curvature. As illustrated in FIGS. 33A-33C, particles remain focused over a wide range of $R_c$, and the focused particle trains are progressively displaced laterally away from the inner wall with increased $R_c$. These results support the theory and indicate the important role the secondary Dean flow plays in influencing the lateral displacement of single-stream focused particles over a wide range of $R_c$. As the $R_c$ is increased beyond a certain value for a given channel geometry and particle size, the Dean drag becomes more dominant than inertial lift and the single stream focused particles start to drift away from the inner wall to form multiple-stream band of focused particles, as shown in FIG. 33B. Further increase in $R_c$ leads to complex fluid behavior disrupting the band and mixing. This suggests there is an upper limit on $D_e$ above which particles start to mix due to dominant Dean flow. In addition to $D_e$, particle size to channel geometry ratio and radius curvature is a strong influence on particle behavior.

To investigate the relationship between various parameters affecting focusing of particles, different flow experiments with varying particle sizes and channel geometries were conducted. We tested a range of particle diameters (2-15-μm) and channel geometries ($D_h$ 55-183-μm and radius of curvature 1.4-9.5 mm) for $R_c$ values ranging from 4 to 700. FIG. 33C shows the results of lateral displacement of focused particles plotted as a function $R_f$ for the different conditions tested. The data is normalized and all calculations were based on n=−0.43. The results indicate that, although the magnitudes differ, the various parameters affect the balance of Drag forces and inertia lift in similar fashion, which is in good agreement with the theoretical prediction. High value on the y-axis indicate $F_z \gg F_{drag}$, resulting in smaller lateral displacement of the focused particles from the inner wall. This is accomplished by focusing a particular particle size at low $R_c$ or by increasing the radius of curvature for a given $R_c$. Increase in $R_c$ or decrease in radius of curvature result in lateral displacement away from the inner wall.

Figure 34A:
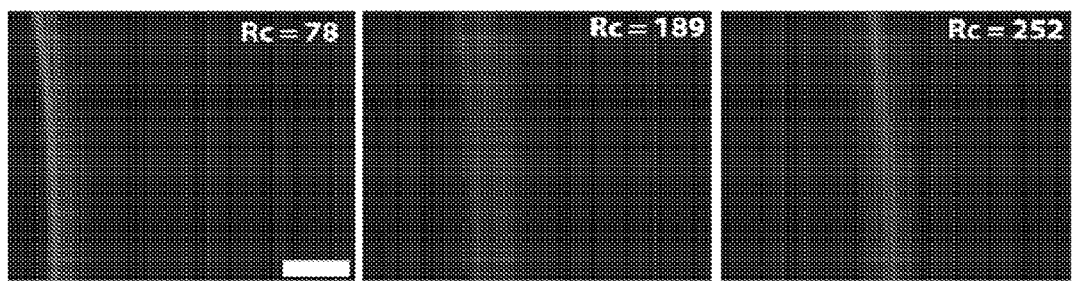
FIG. 34A is a representation of focusing within an expanding spiral channel of an exemplary focusing system for various $R_c$.
Figure 34B:
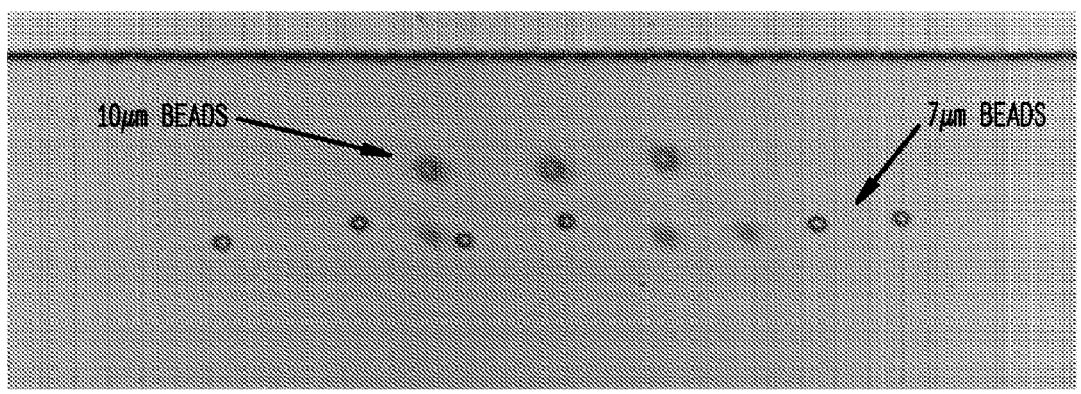
FIG. 34B is a side view illustrating longitudinal ordering of various particle sizes within the channel of FIG. 34A.

To investigate lateral displacement of focused particles in detail, different particle sizes were mixed and tested at various flow rates. At low flow rates, 10-μm and 7-μm particles are focused at the same streamline, indicative of inertia lift dominating over Dean drag, as shown in FIGS. 34A and 34B. As $R_c$ increases, both particle sizes are pushed away from the inner wall, in agreement with an increased contribution from Dean drag that is predicted, as discussed earlier. However, the smaller particles are affected more by the increase in $R_c$ in comparison to the larger particles and consequently drift away into a new equilibrium position further away from the inner wall. This new equilibrium position is independent of the presence of larger particles. Thus for a given channel geometry and $R_c$, the particles will always focus at a predicted equilibrium position.

Example 18

Figure 35A:
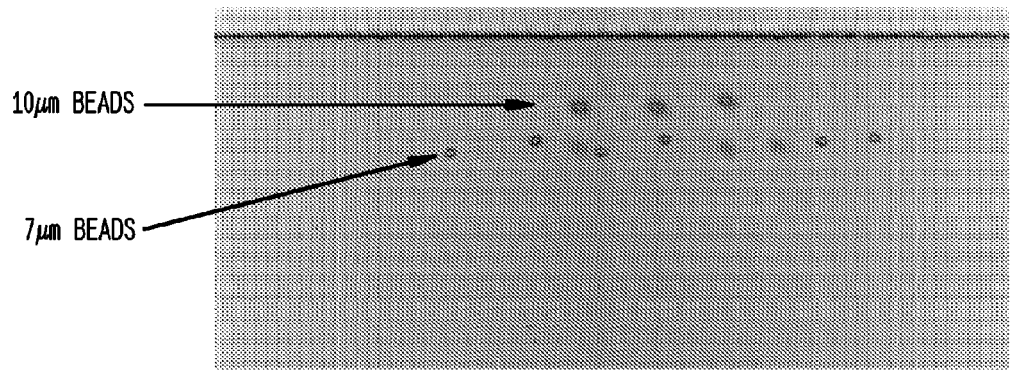
FIG. 35A is a side view of relative particle size and ordering within an expanding spiral channel of an exemplary focusing system.
Figure 35B:
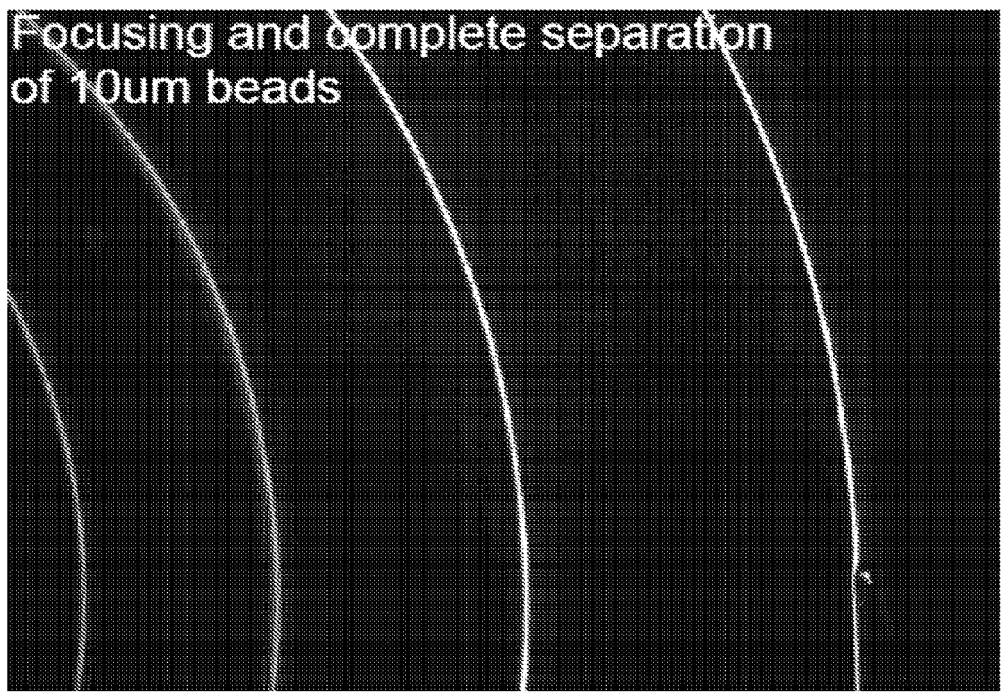
FIG. 35B is an illustration of the focusing of 10-µm particles within the channel of FIG. 35A.
Figure 35C:
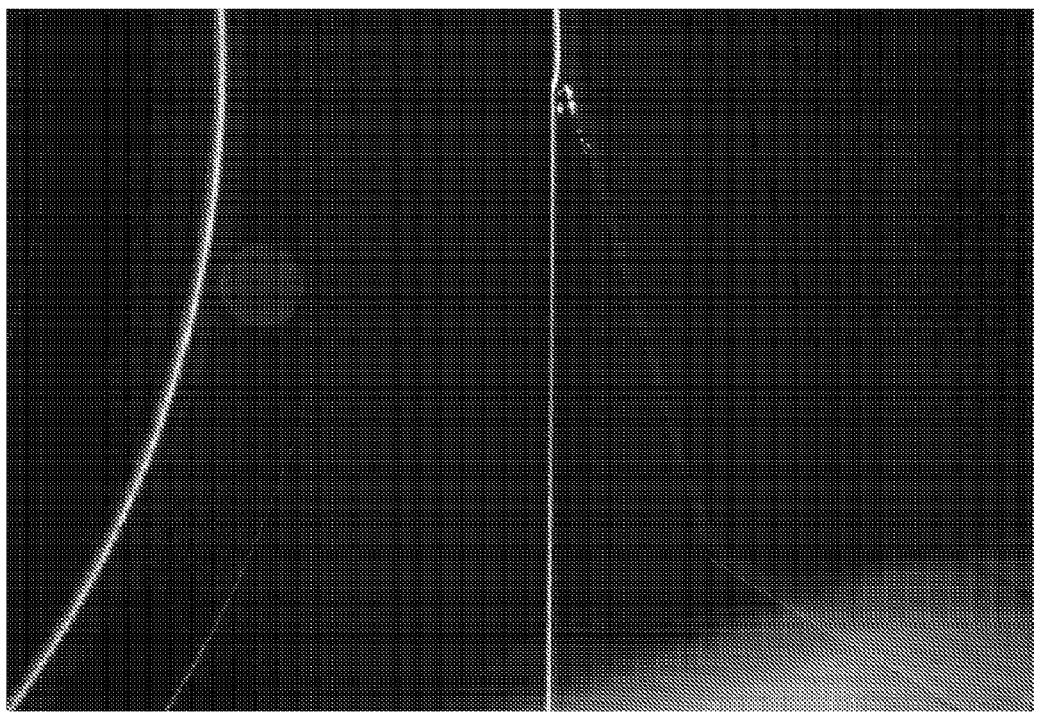
FIG. 35C is an illustration of the focusing of 10-µm particles within the channel of FIG. 35A.
Figure 35D:
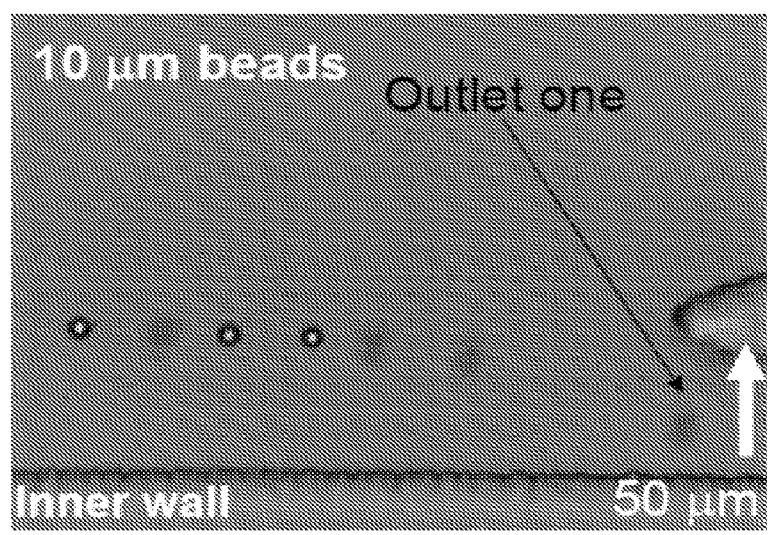
FIG. 35D is a side view of a 10-µm particle within the channel of FIG. 35A.
Figure 35E:
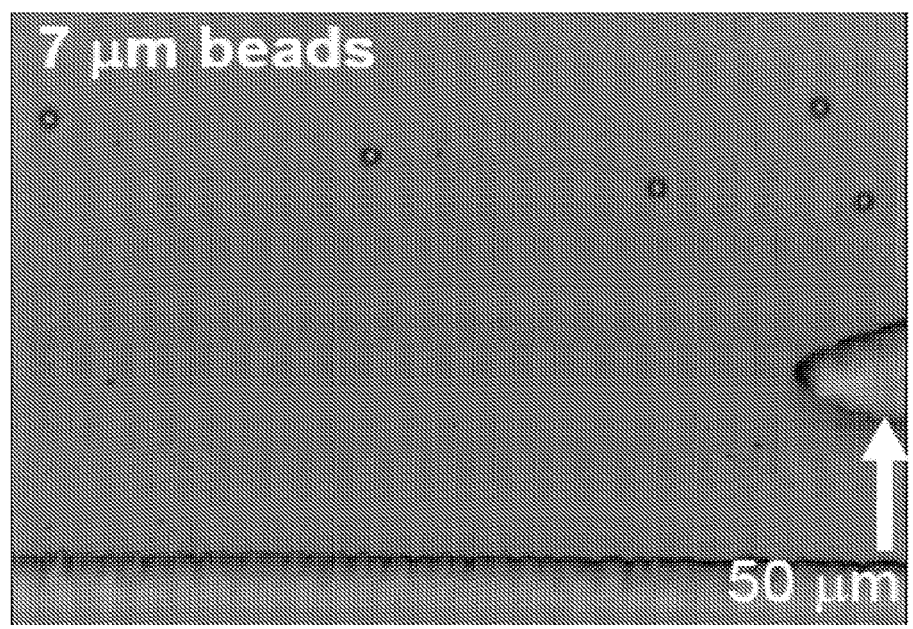
FIG. 35E is a side view of a 7-µm particle within the channel of FIG. 35A.
Figure 35F:
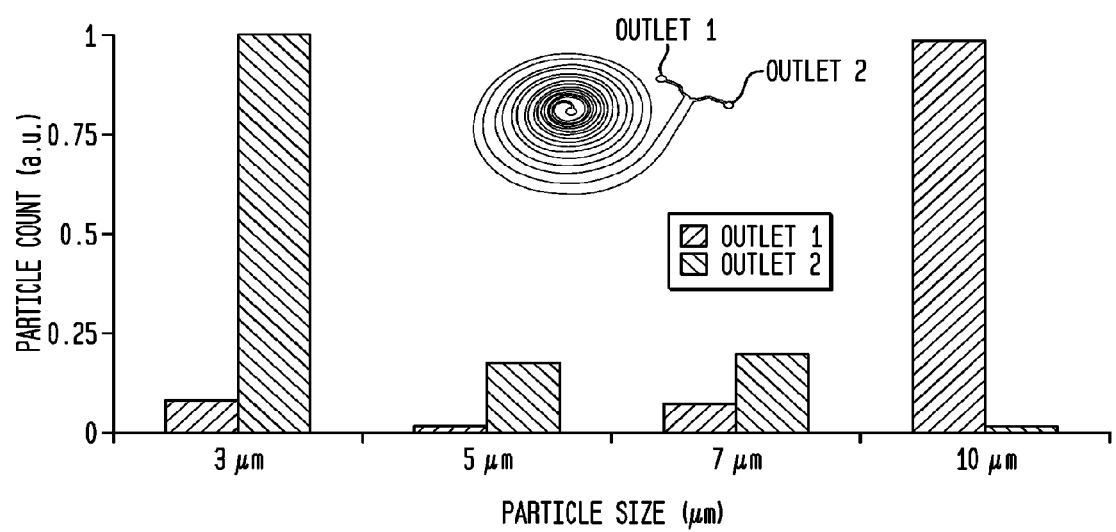
FIG. 35F is a graphical representation of particle count versus particle size within the channel of FIG. 35A.

Referring to FIGS. 35A-35F, separation applications based on differential equilibrium displacement within a spiral microfluidic device can be demonstrated. A cocktail mixture of particles (10, 7, 5 and 3-μm) were flown through a microfluidic spiral device with a channel depth of 50-μm with two outlets. One of the outlets was a channel of 50-μm wide and the other one was 950-μm. According to the theory and experimental findings, this specific dimension should allow the 10, 7 and 5-μm beads to focus while the 3-μm beads remain unfocused for any given $R_c$. As shown in FIGS. 32A-32F, increasing the flow rate pushes the 7 and 5-μm beads away from the inner wall, while the 10-μm beads are intact focused in a single streamline closest to the inlet and can be effectively separated. In this exemplary system, close to 100% separation of 10-μm beads is provided, as shown in FIG. 35F, at a flow rate of 3.5 ml/min.

Example 19

FIG. 36 illustrates utilizing inertial focusing for particle separation. An input solution of 0.1% w/v of mean diameter 3.87 μm (4) and 7.32 μm (7), uniformly distributed, was introduced into a single asymmetric device 100 (narrow)-160 (wide) μm in width, 50 μm tall, and 3 cm in length. At the outlet the channel was split into 5 exit channels with equivalent resistance and fractions were collected for a flow at Re ~8. Flow of a total of 1 mL of solution over 10 minutes allowed ample sample for analysis by coulter counter. Histograms of particle sizes are shown for each of these fractions (numbers 1-5 and indicated in the image). The volumetric ratio between 4 (3-5 μm) and 7 (6-8.5 μm) micrometer particles is shown above each histogram. Notably in fraction 2 the larger particles are enhanced two-fold while in fraction 5 the larger particles are depleted ~200 times.

Example 20

Figure 37:
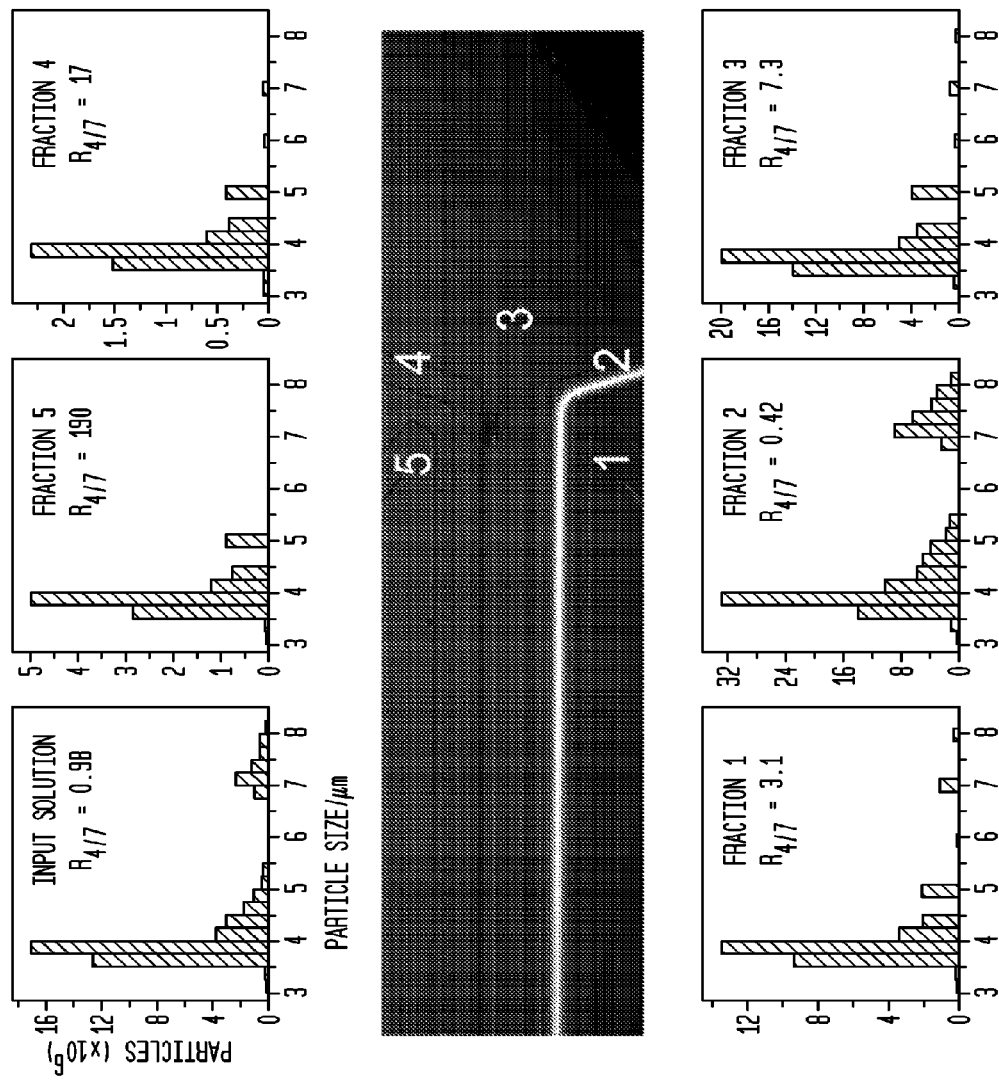
FIG. 37 is a representation of focusing behavior in symmetric curving channels within an exemplary focusing system.

FIG. 37 illustrates focusing behavior in symmetric curving channels. As $R_e$ number increases from 0.5 to 5 a transition to two focused streams is observed. As $R_e$ is increased further stable but more complex behavior is observed. Scale bar is 50 µm.

Example 21

Figure 38:
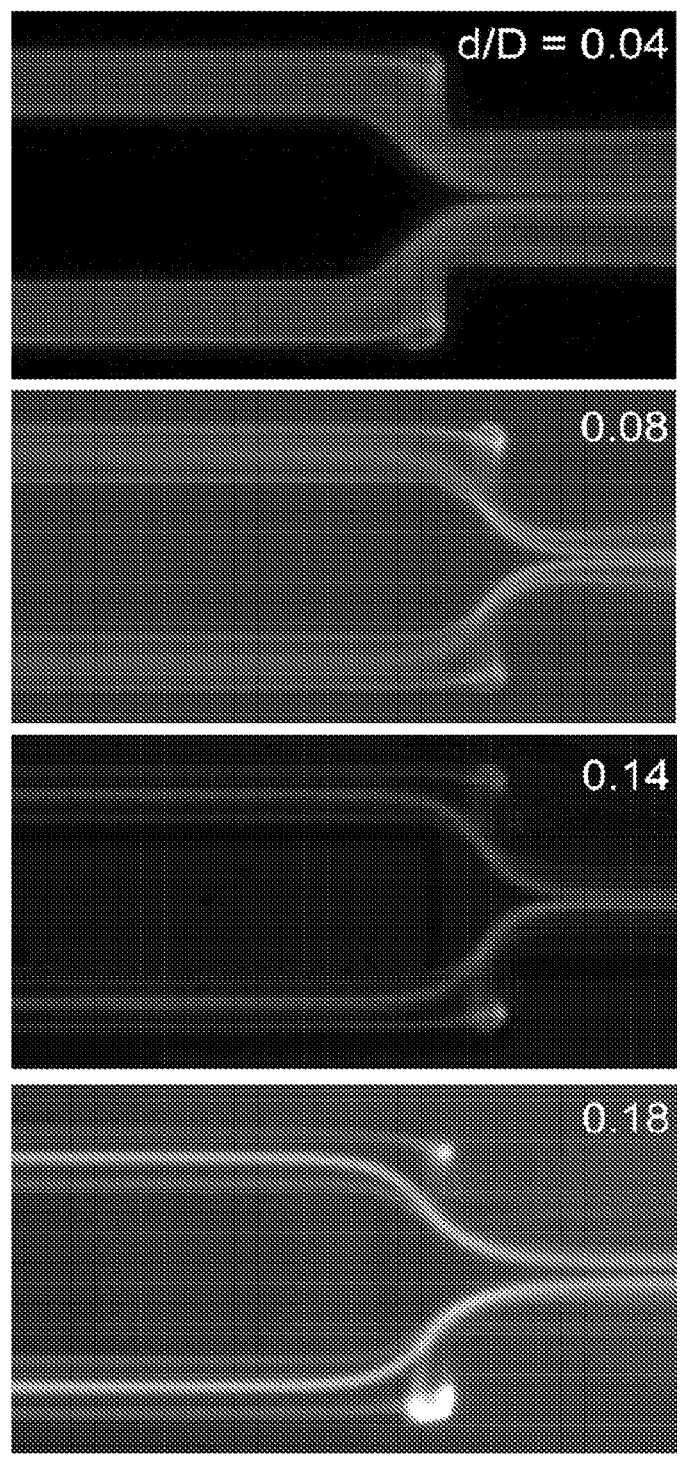
FIG. 38 is a top view of an exemplary channel representing the dependence of particle focusing on $a/D_h$.

FIG. 38 illustrates the dependence of particle focusing on $a/D_h$. Streak images at the outlet are shown 3 cm downstream of the inlet for a flow at Re=100. The image is shown at the recombination of two branches to illustrate the uniformity of the flow profile from channel to channel.

Example 22

FIG. 39 illustrates focusing behavior for channels of 35 µm to 65 µm width. The average radius of curvature for the small dimension is 32.5 µm. Focusing to a single stream is observed $\sim R_e$ of 5 while focusing to two streams is observed at higher $R_e$ and at lower Re number. The particle diameter is 10 µm. Scale bar is 50 µm.

Example 23

FIG. 40 illustrates focusing behavior for channels of 50 µm to 80 µm width. The average radius of curvature for the small dimension is 40 µm. Focusing to a single stream is observed $\sim R_e$ of 2.5 while focusing to two streams is observed at higher $R_e$. Above $R_e$=25 more complex but stable behavior is observed. The particle diameter is 10 µm. Scale bar is 50 µm.

Example 24

FIG. 41 illustrates focusing behavior for channels of 100 µm to 160 µm width. The average radius of curvature for the small dimension is 80 µm. Focusing to a single stream is observed $\sim R_e$ of 12 while more complex but stable behavior is observed for higher $R_e$. The particle diameter is 10 µm. Scale bar is 100 µm.

Example 25

FIG. 42 illustrates focusing behavior for channels of 350 µm to 650 µm width. The average radius of curvature for the small dimension is 325 µm. Focusing to a single stream is observed $\sim R_e$ of 90 while more complex but stable behavior is observed for higher $R_e$. The particle diameter is 10 µm. Scale bar is 100 µm.

Example 26

Figure 43:
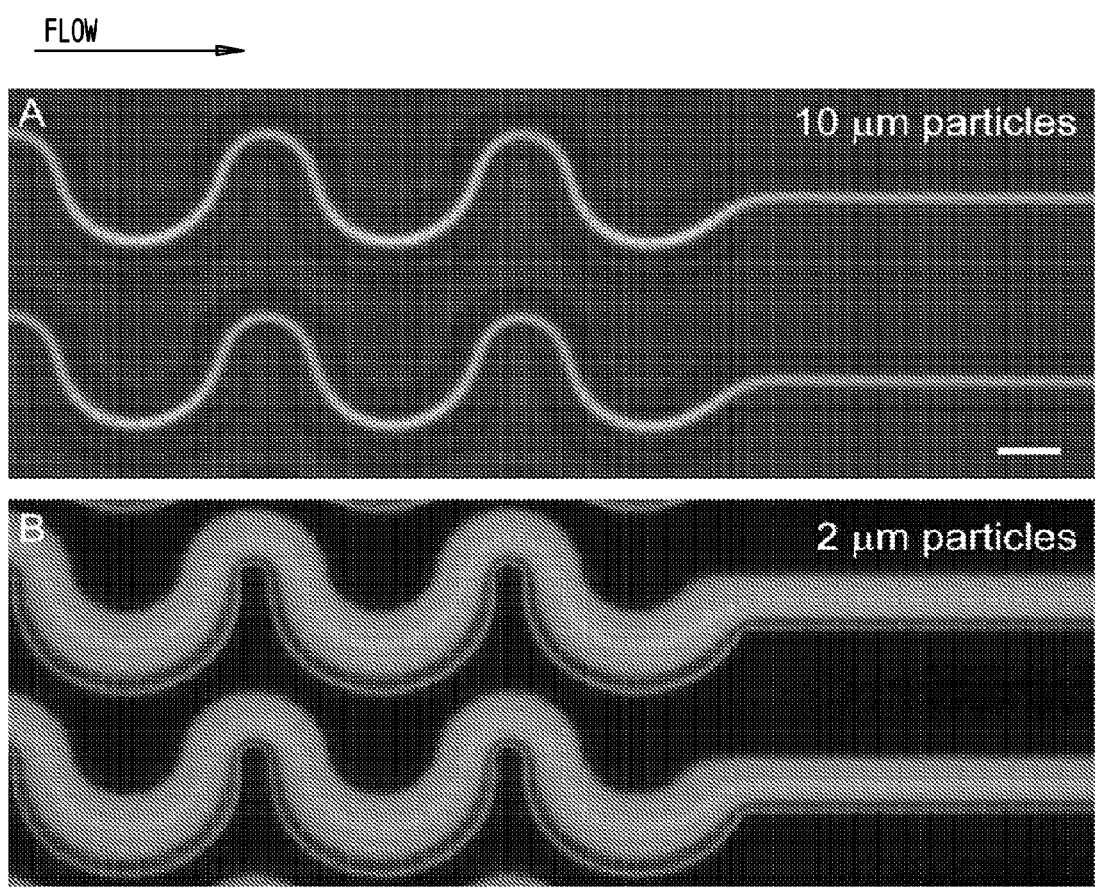
FIG. 43 is a side view illustrating $R_e$ dependent focusing for separation within an exemplary focusing system.

FIG. 43 illustrates particle dependent focusing for separation. A uniform mixture 10 µm and 2 µm particles was input at the inlet and fluorescent streak images were observed at the outlet for (A) the green fluorescent 10 µm particles and (B) the red fluorescent 2 µm particles. The flow is at a $R_e$ of 5. There is a distinct separation across streamlines for the different size particles with no externally applied forces. The scale bar is 50 µm.

Example 27

FIG. 44 illustrates focusing of blood cells in the same manner as rigid particles. Five percent whole blood diluted in PBS is run through rectangular channels of 50 µm width. At the outlet, 3 cm downstream, streak images of cells are observed in phase contrast. These appear as dark streams in the gray channel. The channel edges are also dark. As in the case with rigid particles 3 streaks are observed which correspond to four focus points on the rectangular channel faces.

Example 28

Figure 45A:
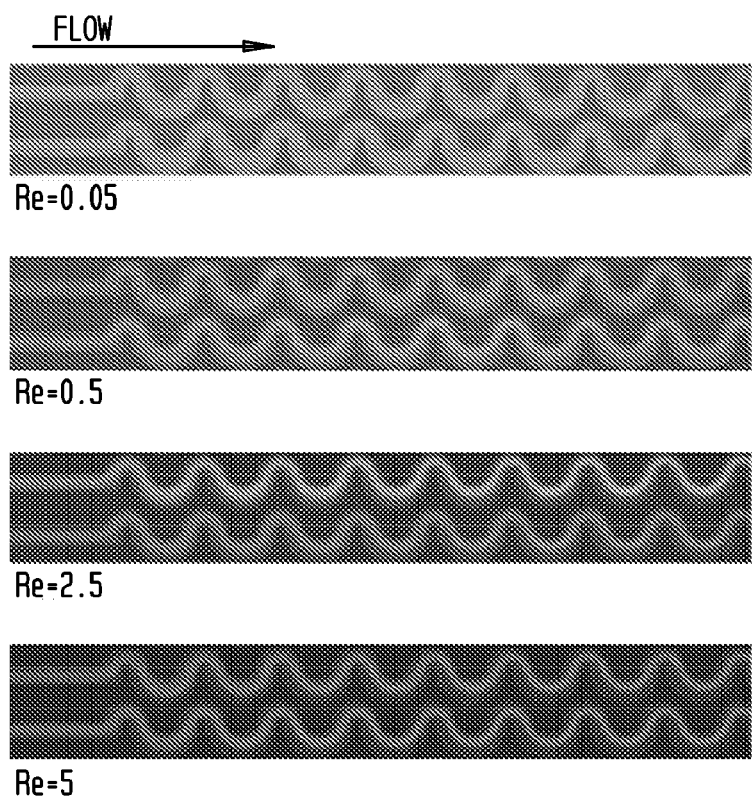
FIG. 45A is a side view of streak images of cells focusing for various $R_e$.
Figure 45B:
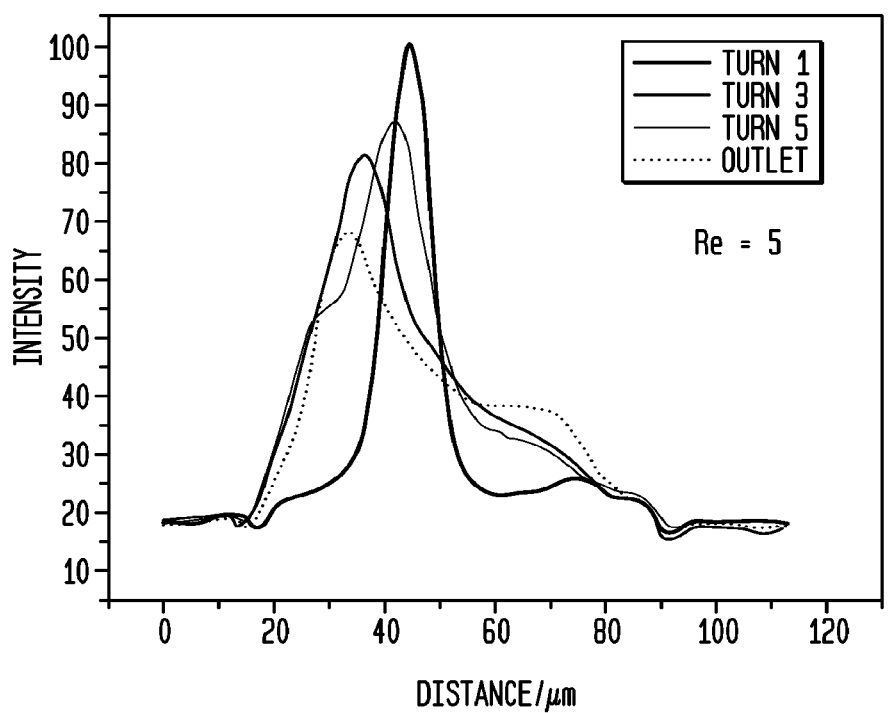
FIG. 45B is a representation of intensity cross-sections of cultured cells at various turns within an asymmetric channel.

FIGS. 45A and 45B illustrate focusing of cultured cell lines. As with particles, deformable cells are focused to single streams. FIG. 43A shows streak images of cells focusing for various $R_e$ numbers are shown. The inlet of each focusing area is shown on the left. Focusing to a single lane starts to occur for $R_e\sim2$ after 3 cm of travel. In FIG. 43B, intensity cross sections at various turns and at the outlet are shown. Note that at the outlet the width of the focused stream is comparable to the diameter of a single cell (~15 µm).

Experimental Conditions and Apparatus

While many experimental conditions can be used to create and utilize the exemplary systems described herein, some conditions used to achieve the results discussed above are presented below.

Materials

Fluorescent polystyrene microparticles (density ~1.05 g/ml) were either purchased from Bangs Laboratories (Fishers, Ind.) or Duke Scientific (Fremont, Calif.). For 4 (3.87) µm and 7 (7.32) µm particles the Bangs Labs product codes were FS05F/7772 and FS06F/6316 respectively. For 2 (2.0) µm, 9 µm, 10 (9.9) µm and 17 µm the Duke Scientific product numbers were R0200, 36-3, G1000 and 35-4. Particles were mixed to desired weight fractions by dilution in Phosphate buffered saline (PBS) and stabilized by addition of 0.1% Tween 20. Particles were mixed to desired weight fractions by dilution in PBS and stabilized by addition of 0.1% Tween 20. In the various described experiments particle wt/vol % varied between 0.1% and 1%. Silicone oil droplets were formed from 10% wt/vol DC 200 (10 centistokes, Dow Corning) stabilized with 2% wt/vol polyethylene glycol monooleate (molecular weight 860, SigmaAldrich). The mixture was shaken vigorously and allowed to settle for 20 min. Solution was taken from the bottom 1 cm of the vial to ensure a size range of droplets <20-µm. Solutions of different densities were prepared from ethanol (ρ=0.78 g/ml) or concentrated $CaCl_2$ solutions (ρ=1.12 and 1.23 g/ml); viscosities of these solutions varied from 1 to 3 centipoise.

Cells (H1650 lung cancer cell line) were cultured in RPMI 1640 media with 10% FBS and trypsinized and resuspended in PBS prior to use. Whole blood was collected from a healthy volunteer in EDTA coated vacutainer tubes by a trained phlebotomist. Blood was diluted in PBS to 1-5% for experiments. Cells were dyed using either calcein AM (5 µM), a cytoplasmic dye, or Hoescht 33342 (1 µM), which is a cell permeable DNA dye.

Microfabrication

Exemplary devices described herein were fabricated using standard soft lithography techniques. Briefly, SU-8 2035 was spun at 2250 rpm for 30 seconds to create a 50 µm thick layer on a 10 cm silicon wafer. Thickness was measured using a microscope with a metered focus and varied between 42-56 µm across a wafer. The pattern was photolithographically defined in this layer using a mylar mask printed at 40,000 dpi (See Supplementary AutoCAD files). After development PDMS was poured onto the SU-8 master at a 10 to 1 ratio of base to crosslinker, degassed in a vacuum chamber, and cured at 65 degree C. overnight. The devices were then cut from the mold; ports were punched with a sharpened flat tip needle, and then bonded to glass slides or cover glass using oxygen plasma. After plasma treatment and placement onto the glass substrate the devices were maintained at 70 degree C. on a hotplate for 15 minutes to increase bonding.

Dimensionless Numbers

For a straight rectangular channel the Re, a ratio between the inertial and viscous forces can be easily defined as $\rho U D_h/\mu$ where $\rho$ is the density of the fluid, U is the mean velocity, and $D_h$, the hydraulic diameter, is defined as $2ab/(a+b)$. With a and b being the width and height of the channel. However, for curving channels and asymmetric curving channels taking only a rectangular cross-section and considering the $R_e$ for this will overestimate the inertial effects. In order to define a correct $R_e$ for these geometries fluid dynamic simulations were conducted of the geometry using COMSOL Multiphysics. A $R_e$ was determined from the balance of inertial to viscous forces for node points within the middle of the stream. This method yielded the analytical $R_e$ for straight rectangular channels as well. In the case of the asymmetric channels the $R_e$ differs in the small or large curving turn and for simplicity a single $R_e$ was used corresponding to the small turn throughout this work. As an example an average velocity of 42 cm/sec corresponds to a $R_e$ of 5 in a 50 μm×50 μm small curving channel of radius of curvature, r=40 μm, while $R_e$=20 for a straight rectangular channel. Dean numbers were also calculated using these simulated $R_e$.

Particle Localization

The bias and accuracy of localization based on fitting to a functional form will depend on the pixel size (i.e. the level of sampling) and the signal to noise of the system (S/N). S/N is defined as, $S/N=(I_o-I_b)/\sigma_o$, that is the average intensity of the background subtracted from the average intensity of the object and divided by the standard deviation or noise over the object. This is the highest noise region due to shot noise being proportional to the square root of the number of photoelectrons. For the system, with highly dyed fluorescent microspheres the S/N was determined to be 60 by taking the standard deviation of intensity levels of a single stream over distance. This is in contrast to systems imaging single molecules which have typical S/N of 4-10. For the signal to noise ratio and a pixel sampling size of 330 nm, a predicted accuracy of localization of ~3 nm is expected. This result allows confidence in localization measurements that are larger than this value by around an order of magnitude.

Image Analysis

For flow cytometry applications and to determine autocorrelation functions for flowing streams of particles Matlab (The Mathworks Inc.) was used to conduct image analysis of sequences of images. First, for each movie a kernel image was selected that was representative of an in focus particle. This kernel was then convolved with the image to form an intensity map with peaks at particle positions. A defined section of this intensity map that corresponded to the distance a particle traveled in a given frame was converted to a time series of intensity and appended onto an array with time series from previous frames. This process was repeated for each frame until a full time series was assembled of particle flow through the detection area. The temporal signal was used to determine an autocorrelation function to analyze the favored distances between particles and length of trains. It should be noted that convolution will necessarily increase the apparent width of a given particle, but was conducted to obtain single peaks at particle positions from the multiple intensity peak raw data.

Experimental Setup

As described herein, experiments to determine the distribution of particle positions within the channels were performed using time lapse fluorescence microscopy. Solutions were introduced into a syringe and connected by PEEK tubing to the PDMS devices. In one embodiment, the system included a filter region to remove any large debris, curving separation microchannels, and five collection outlets, as shown in FIG. 33. In other embodiments, the system included multiple inlets and a single collection outlet. Outlets of PEEK tubing were also connected to the outlet ports of the device and routed into a waste container or collection tubes. Flow was driven by a syringe pump (Harvard Apparatus PHD 2000). In one embodiment, curving channels having a width of 350-μm on the small radius of curvature turn and a width of 650-μm on the large radius of curvature turn were used. The average radius of curvature on the narrow and wide turns is 325 and 890-μm, respectively. This geometry results in an asymmetric system with a Dean drag ($F_D$) that is ~8 times larger in the small radius turn than in the large turn. In the illustrated embodiment, the entirety of the separation channel is composed of 31 units consisting of one small and one large turn, wound into three straight segments (10-11 units each) to reduce the device footprint.

PDMS devices were mounted onto the stage of an inverted fluorescent microscope (Nikon TE2000-U). Fluorescent streak images were obtained with a cooled CCD camera (Spot RT, Diagnostic Instruments) using exposure times from 500-5000 ms, depending on particle concentration and flow rate. Images were collected in the Spot software and further analysis was conducted using ImageJ.

Confocal imaging was conducted in the same manner as inverted fluorescent imaging except devices were bonded to coverglass slides to allow objective access. A 40× objective was used with a pinhole diameter of 1.05 airy disks. The z-y plane was scanned 8 successive times with a residence time of 0.3 ms at each scan point to obtain the images.

High-speed camera imaging was conducted in the same manner as inverted fluorescent imaging except white light in kohler illumination with the object plane was utilized. All neutral density filters were removed and the highest power on the lamp allowed imaging with 2 μs exposures using a Phantom v4.2 camera (Vision Research, New Jersey, USA). For flow cytometry applications, images were collected at an interval of 10 μs using a collection window that was 32×32 pixels. For larger single images and movies intervals from 20-70 μs were used.

After separating particle solutions into fractions, individual fractions were analyzed using a Coulter counter (Beckman Coulter Z2). The coulter aperture size was 100 μm and gain and current were set to observe particles in the size range of 3-9 μm. Collected samples were diluted between 400 and 800 times to allow sufficient dilution for successful counting.

Blood cells were analyzed using a flow cytometer (Becton Dickinson FACSCalibur). Forward and side scatter were observed over a log scale to differentiate between platelets and other blood components. Detector voltages were turned to obtain the correct gain to observe both the scatter of the larger and smaller particles. Samples were generally diluted 100 times for measurements. 25,000-100,000 counts were observed for each sample.

Emulsions

Silicone oil in water emulsions were generated by mixing of these two immiscible phases with emulsifier present in the aqueous (continuous) phase for stabilization from coalescence of the resulting oil droplets. Silicone oil with dynamic viscosity of 9.35 cP and density of 0.935 g/cm³ was employed as the disperse phase (Dow Corning, Midland, Mich.; 200 fluid 10 cst), while the continuous phase was composed of de-ionized water containing 2% w/v poly(ethylene glycol) monooleate (Sigma-Aldrich, St. Louis, Mo.; $M_n$~860) to stabilize the emulsion. After vigorous mixing of 5% v/v silicone oil with the aqueous phase, samples free of droplets larger than around 20-μm in diameter were obtained via sedimentation for subsequent experimentation. Specifically, emulsion was extracted 1 cm from the bottom of evenly mixed emulsion that had been allowed to stand for 20 minutes so that large droplets completely evacuated the lower 2 cm of emulsion, as deduced from stokes drag on a buoyant spherical particle (v=$D^2$ ($\rho_{aqu}-\rho_{oil}$)g/(18 $\eta_{aqu}$)~(3.55×$10^4$ $m^{-2}s^{-1}$) $D^2$).

PDMS Beads

PDMS (Polydimethylsiloxane) beads with a wide range in diameter were made in a fashion quite similar to silicone emulsions. PDMS was mixed with the standard 10:1 ratio of resin to crosslinker (Dow Corning; Sylgard 184), but prior to curing, degassed resin-crosslinker mixture was added to the same 2% w/v poly(ethylene glycol) monooleate aqueous solution at 10% w/v PDMS. After vortex-mixing until the desired size range was achieved, the tube of uncured PDMS emulsion was placed in a water bath at 70-90° C. for at least three hours to allow hardening of the liquid droplets into solid beads of PDMS. Beads larger than about 20-μm were removed from extracted solutions of beads prior to experiment via filtration through a duplicate filter of a device as in FIG. 33.

In general, the embodiments disclosed herein present a nonintuitive phenomena associated with particles moving in a laminar flow that yields different levels of ordering within microchannel systems. Ranges of parameters are disclosed for utilization of the phenomena and key principles and forces that may responsible for the ordering are also suggested. There are many advantages associated with the system of the invention including rapid continuous processing of samples without the need for filters or mechanical or electrical parts, high throughput applications, low noise results, and an independence in focusing for particle shape and density. Inertial focusing of the systems and methods described herein is ideal for particle sorting applications because of the precision of particle positioning into a single stream and the controlled longitudinal spacing between particles. Precise control of particle streamlines (i.e. small standard deviation of particle position) allows sorting with small induced changes in particle position. A slight induced movement of a particle away from the equilibrium streamline will yield a large difference over the background standard deviation of particle position and can allow the target particle to be extracted at a bifurcation in the channel without high levels of false positives and at high speeds. Additionally, the single file nature of the ordering and the regular longitudinal spacing insures that a deflected particle would not interact significantly with other particles in the flow. The particular geometries presented can be used in any number of applications to direct interactions of particles in inertial flows, and the system of the invention is applicable on a microscale as well as on a macroscale. It is appreciated that any and all channel geometries, system embodiments, and experimental parameters described herein can be combined in a multitude of ways to achieve specific results in various applications.

Applications of the system of the invention are widely diverse and will be useful in a wide range of industries, both commercial and academic. For example, in the biomedical field, applications of the system can be used in conventional techniques such as FACS, MACS, impedance-based particle counting, blood filtration, rare cell identification and filtration, hetero/hemogenous cell signaling, among many others. For example, the properties of the particle motion induced by inertial focusing are ideally suited to cell separation and enumeration technologies. The extreme alignment and discrete spacing of each cell can be exploited to enumerate the cells individually as they flow through a microfluidic channel at high speeds by, for example, labeling cells with fluorescent tags or magnetic particles. The systems and methods described herein have many advantages over current rare-cell separation and enumeration techniques. Immunomagnetic techniques—where cells of interest are tagged with antibody coated magnetic beads—are often employed, however, cell losses occur in the processing of these samples because of its complexity and manual handling steps. A further advantage of the systems and methods is the ability to perform the cell ordering and separation at the point of care without the need for bulky equipment that is only suitable for the laboratory setting. Particle focusing techniques such as those described here can be combined with established immunomagnetic labeling and microelectronics technology to design and construct an cell separation microchip, for example, capable of handling whole blood samples that will not suffer from the problems of the current technologies. Microelectronic components can be integrated into microfluidic devices and therefore combine fluid flow and electronic manipulation or detection in a single device. The systems and methods described herein will create opportunities for the rapid screening of patients for a number of diseases and allow clinicians to follow the treatment progress of their patients.

In other applications, for example in industry, possible applications of the systems and methods of the invention can include use in the development of cosmetics, lubricants, pigments, environmental monitoring for particulates, natural oil extraction, particle synthesis, and polymer bead manufacturing, among many others. In research, the system of the invention can be used in tissue engineering, drug control release mechanism studies, cell signaling studies, protein crystallization, virus/bacteria capture, nucleic acid purification, and chemistry specific extractions among many others. In the field of agriculture, the system of the invention can find application in the development of multi-phase fertilizer emulsions, multi-phase pesticide emulsions, flow cytometry, as well as in hematology analysis. The possible applications for the systems and methods of the invention are varied and broad across all research, industrial, and commercial applications.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for focusing particles suspended within a moving fluid, the method comprising:

providing a substrate including at least one channel having an inlet, an outlet, a plurality of sides, wherein the relative geometry of the sides defines an aspect ratio, and a channel hydraulic diameter ($D_h$);

flowing a fluid having a substantially constant kinematic viscosity (v) that includes suspended particles, each having a particle diameter (a), through the at least one channel; and driving the fluid that includes the suspended particles through the at least one channel at a maximum channel velocity ($U_m$) resulting in a laminar fluid flow and a particle Reynolds Number ($R_p$) of greater than or equal to 0.2, wherein the particle Reynolds number is defined as, $R_p = U_m a^2 / v D_n$, and resulting in forming one or more localized stream lines in the fluid;

wherein each localized stream line defines a width that is substantially equal to or greater than a size of the focused particles, and the particles suspended in the fluid are focused into the one or more localized stream lines, wherein the number and relative cross-sectional position of the one or more localized stream lines are uniquely defined by the aspect ratio and the particle Reynolds number.

2. The method of claim 1, wherein the aspect ratio is defined by a width and a height of the at least one channel, and wherein when the aspect ratio is substantially 1 to 1, the particles suspended in the fluid are focused into four localized stream lines.

3. The method of claim 1, wherein the aspect ratio is defined by a width and a height of the at least one channel, and wherein when the aspect ratio is substantially 2 to 1, the particles suspended in the fluid are focused into two localized stream lines.

4. The method of claim 1, wherein the at least one channel is a straight channel dimensioned and configured such that the particles suspended in the fluid are focused into each of at least two localized stream lines formed in the straight channel.

5. The method of claim 1, wherein the at least one channel is a curved channel dimensioned and configured such that the particles suspended in the fluid are focused into a single localized stream line formed in the curved channel.

6. The method of claim 5, wherein the curved channel is symmetric and sigmoidal.

7. The method of claim 5, wherein the curved channel is asymmetric and sigmoidal.

8. The method of claim 5, wherein a radius of curvature of the curved channel varies.

9. The method of claim 1, wherein a ratio of the particle diameter to the at least one channel hydraulic diameter is greater than or equal to about 0.07 and less than or equal to about 0.5.

10. The method of claim 1, wherein the width defined by each localized stream line is about five times the particle diameter.

11. The method of claim 1, further comprising:
flowing the fluid through at least first and second outlet branches at an outlet portion of the at least one channel;
wherein at least one of the first and second outlet branches is located to receive the particles that are focused into a localized stream line.

12. The method of claim 1, wherein the particles have a particle diameter in a range of 0.01 μm to 40 μm.

13. The method of claim 1, further comprising driving the fluid that includes the suspended particles through the at least one channel such that the focused particles are spaced approximately evenly longitudinally within a localized stream line.

14. The method of claim 1, wherein the aspect ratio is defined by a width and a height of the at least one channel, and wherein the aspect ratio varies along the at least one channel from about 1 at the inlet to about 2 at the outlet.

15. The method of claim 1, further comprising detecting particles focused in a localized stream line.

16. The method of claim 1, further comprising tagging selected particles with one or more tags.

17. The method of claim 16, wherein the tag comprises a magnetic bead coupled to one or more antibodies that specifically bind to the selected particles.

* * * * *

UNITED STATES PATENT AND TRADEMARK OFFICE
CERTIFICATE OF CORRECTION

PATENT NO.      : 8,807,879 B2
APPLICATION NO. : 13/619309
DATED           : August 19, 2014
INVENTOR(S)     : Mehmet Toner et al.

It is certified that error appears in the above-identified patent and that said Letters Patent is hereby corrected as shown below:

In the Specification

Column 1, Line 10:

Delete "claims" and Insert -- which claims --

In the Claims

Column 52, Claim 1, Line 65:

Delete " $R_p = \dfrac{U_m a^2}{\nu D n}$ , " and Insert -- $R_p = \dfrac{U_m a^2}{\nu D_h}$ , --

Signed and Sealed this
Twenty-fifth Day of November, 2014

Michelle K. Lee
*Deputy Director of the United States Patent and Trademark Office*